(12) United States Patent
Eidam et al.

(10) Patent No.: US 7,723,350 B2
(45) Date of Patent: May 25, 2010

(54) SPIROINDOLINES AS MODULATORS OF CHEMOKINE RECEPTORS

(75) Inventors: Hilary Schenck Eidam, King of Prussia, PA (US); Pamela A. Haile, King of Prussia, PA (US); Terry Vincent Hughes, King of Prussia, PA (US); Clark A. Sehon, King of Prussia, PA (US)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

(21) Appl. No.: 12/142,899

(22) Filed: Jun. 20, 2008

(65) Prior Publication Data

US 2008/0318990 A1  Dec. 25, 2008

(51) Int. Cl.
*A61K 31/438* (2006.01)
*C07D 471/10* (2006.01)

(52) U.S. Cl. .................................. 514/278; 546/17
(58) Field of Classification Search ............... 514/278; 546/17, 18; 548/409
See application file for complete search history.

(56) References Cited

U.S. PATENT DOCUMENTS

| 5,962,462 A | 10/1999 | Mills et al. ............ 514/278 |
| 2006/0069123 A1 | 3/2006 | Xia et al. ................ 514/316 |

FOREIGN PATENT DOCUMENTS

| WO | WO 2005/063745 | 7/2005 |
| WO | WO 2006/130416 | 12/2006 |
| WO | WO2009/023754 | 2/2009 |
| WO | WO2009/049113 | 4/2009 |
| WO | WO2009/061881 | 5/2009 |

OTHER PUBLICATIONS

Mirzadegan, et al. "Identification of the Binding Site for a Novel Class of CCR2b Chemokine Receptor Antagonists," *J. Biol. Chem.*, 2000, vol. 275(33), pp. 25562-25571.

Freund, et al. "A Convenient Synthetic Route to Spiro [indole-3,4'-piperidin]-2-ones," *Helvetica Chimica Acta*, 2000, vol. 83, pp. 1247-1255.

*Primary Examiner*—Bernard Dentz
*Assistant Examiner*—David E Gallis
(74) *Attorney, Agent, or Firm*—Reid S. Willis; John Lemanowicz

(57) ABSTRACT

The present invention relates to a compound of the following formula:

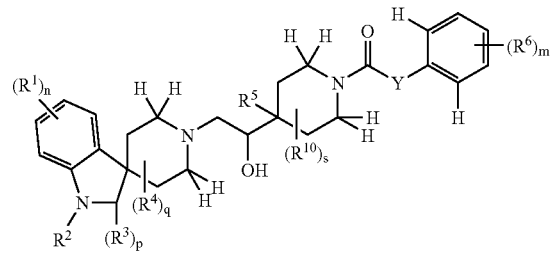

where $R^1$-$R^6$, $R^{10}$, Y, n, m, p, and q are as defined herein. Compounds and compositions of the present invention are useful for the treatment of diseases associated with the overexpression of CCR2.

5 Claims, No Drawings

SPIROINDOLINES AS MODULATORS OF CHEMOKINE RECEPTORS

BACKGROUND OF THE INVENTION

The present invention relates to a class of spiroindolines that are modulators of chemokine receptors, particularly as CCR2 antagonists and their methods of use.

CCR2 is a chemokine receptor that is expressed on a cell surface of monocyctes and some other blood leukocytes. CCR2 binds to the monocyte chemotactic protein MCP-1, and other CC chemokines, which are produced at sites of inflammation and infection. Recruitment of monocytes to inflammatory sites by MCP-1/CCR2 interactions has been implicated in driving the pathogenesis of a number of diseases including multiple inflammatory disorders including rheumatoid arthritis, atherosclerosis, multiple sclerosis, bronchiolitis obliterans syndrome, asthma, allergic rhinitis, eczema, atopic dermatitis, kidney disease, alveolitis, nephritis, liver cirrhosis, congestive heart failure, viral meningitis, cerebral infarction, neuropathy, Kawasaki disease, Alzheimer's disease, stroke, acute nerve injury, HIV infection, AIDS, autoimmune diseases, cancer, sepsis, retinosis, inflammatory bowel disease, transplant arteriosclerosis, idiopathic pulmonary fibrosis, psoriasis, HIV-associated dementia, lupus, erthematosis, hepatitis, pancreatitis, Crohn's disease, endometriosis, metabolic syndrome, and diabetes.

Accordingly, it would be an advance in the art to discover a class of compounds that bind to CCR2, thereby preventing or minimizing the formation of the undesirable MCP1-mediated recruitment of monocytes to inflammatory sites.

SUMMARY OF THE INVENTION

In a first aspect of the invention, there is provided a compound of the following formula I:

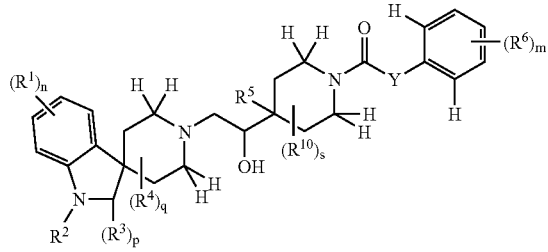

or a pharmaceutically acceptable salt thereof or an enantiomer thereof;
where each $R^1$ is independently halo, $CF_3$, $C_1$-$C_4$-alkyl, $C_1$-$C_4$-alkoxy, $OCF_3$, CN, $C_1$-$C_6$-alkyl-C(O)—NH—, $C_1$-$C_6$-alkyl-NH—C(O)—, —$CH_2$—N($R^7$)$_2$, —$CH_2$—O—$R^8$, $C_1$-$C_4$—S(O)$_r$—, COOH, or heteroaryl;
$R^2$ is H, $C_1$-$C_4$-alkyl, —$CH_2$C(O)O$R^9$, or $CH_2$C(O)N($R^9$)$_2$;
each $R^3$ is independently $C_1$-$C_6$-alkyl or hydroxy-$C_1$-$C_6$-alkyl;
each $R^4$ is independently OH, F, Cl, CN, $C_1$-$C_4$-alkyl, hydroxy-$C_1$-$C_4$-alkyl, or $C_1$-$C_4$-alkoxy;
Y is —NH— or

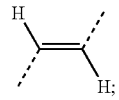

$R^5$ is H, OH, F, Cl, CN, $CF_3$, $C_1$-$C_6$-alkyl, hydroxy-$C_1$-$C_6$-alkyl, or $C_1$-$C_6$-alkoxy;
each $R^6$ is independently halo, $CF_3$, $C_1$-$C_4$-alkyl, $C_1$-$C_4$-alkoxy, $OCF_3$, benzyloxy, or CN;
each $R^7$ is independently H, $C_1$-$C_4$-alkyl, or, together with the nitrogen atom to which they are attached, form a 5- or 6-membered heterocycloalkyl group;
$R^8$ is H, $C_1$-$C_6$-alkyl, benzyl, or phenyl;
each $R^9$ is independently H, $C_1$-$C_6$-alkyl, or benzyl;
each $R^{10}$ is independently OH, F, Cl, CN, $C_1$-$C_4$-alkyl, hydroxy-$C_1$-$C_4$-alkyl, or $C_1$-$C_4$-alkoxy;
n is 0, 1, or 2;
m is 0, 1, 2, or 3;
p is 0, 1, or 2;
q is 0, 1, or 2;
r is 0, 1, or 2; and
s is 0, 1, or 2.

DETAILED DESCRIPTION OF THE INVENTION

In a first aspect, the present invention relates to a compound of formula I:

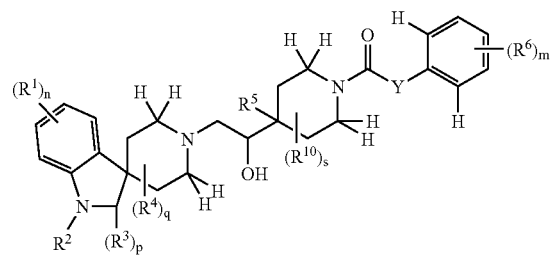

or a pharmaceutically acceptable salt thereof or an enantiomer thereof, wherein $R^1$-$R^6$, n, m, p, q, and s are as previously defined.

In another aspect, the present invention is a compound which is represented by the following formula:

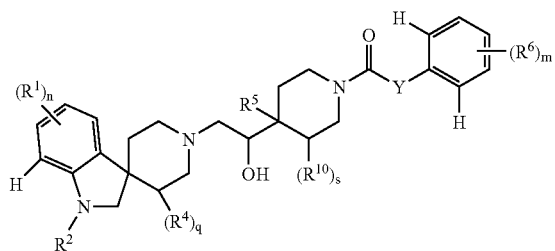

or a pharmaceutically acceptable salt thereof or an enantiomer thereof, wherein
each $R^1$ is independently Cl, F, Br, $CF_3$, CN, $CH_3$, $OCF_3$, $C_1$-$C_4$—S(O)$_r$—, or methoxy;

each $R^6$ is independently F, Cl, Br, $CF_3$, $CH_3$, benzyloxy, or $OCH_3$;

m is 1 or 2;

n is 0, 1, or 2;

q is 0 or 1; and s is 0 or 1.

In another aspect, the present invention is a compound which is represented by the following formula:

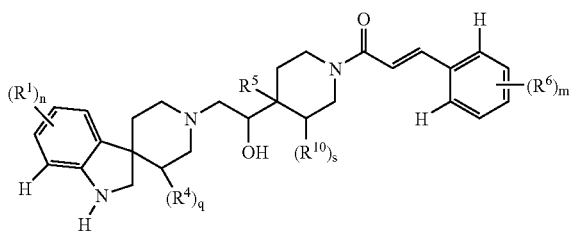

or a pharmaceutically acceptable salt thereof or an enantiomer thereof, wherein $R^4$ is $CH_3$ or OH; and $R^5$ is H or OH.

In another aspect, the present invention is a compound represented by the following formula:

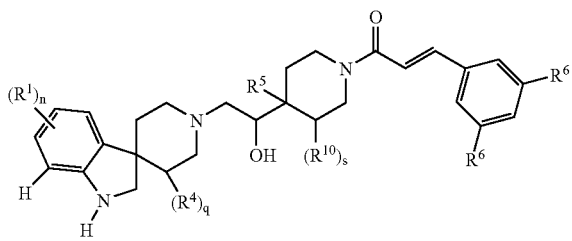

or a pharmaceutically acceptable salt thereof or an enantiomer thereof, where each $R^1$ is independently $CH_3$, F, Cl, or CN;

each $R^6$ is independently F or Cl;

$R^{10}$ is $CH_3$ or OH; and n is 0, 1, or 2.

In another aspect, the present invention is a compound represented by the following formula:

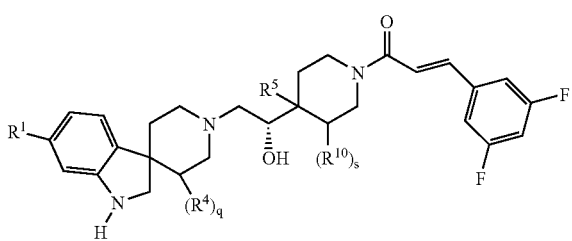

or a pharmaceutically acceptable salt thereof, wherein $R^1$ is Cl, $CH_3$, or CN.

In another aspect, the present invention is a compound represented by the following formula:

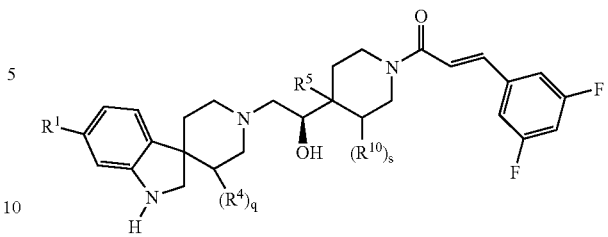

or a pharmaceutically acceptable salt thereof, wherein $R^1$ is Cl, $CH_3$, or CN.

In another aspect, the present invention is a compound which is 2-(6-chloro-1,2-dihydro-1'H-spiro[indole-3,4'-piperidin]-1'-yl)-1-{1-[(2E)-3-(3,5-difluorophenyl)-2-propenoyl]-4-piperidinyl}ethanol; 1'-((2R)-2-{1-[(2E)-3-(3,5-difluorophenyl)-2-propenoyl]-4-hydroxy-4-piperidinyl}-2-hydroxyethyl)-1,2-dihydrospiro[indole-3,4'-piperidine]-6-carbonitrile; 1'-((2S)-2-{1-[(2E)-3-(3,5-difluorophenyl)-2-propenoyl]-4-piperidinyl}-2-hydroxyethyl)-1,2-dihydrospiro[indole-3,4'-piperidine]-6-carbonitrile; 6-chloro-1'-(2-{1-[(2E)-3-(3,5-difluorophenyl)-2-propenoyl]-4-hydroxy-4-piperidinyl}-2-hydroxyethyl)-1,2-dihydrospiro[indole-3,4'-piperidin]-3'-ol; 6-chloro-1'-(2-{1-[(2E)-3-(3,5-difluorophenyl)-2-propenoyl]-4-piperidinyl}-2-hydroxyethyl)-1,2-dihydrospiro[indole-3,4'-piperidin]-3'-ol; 1-[(2E)-3-(3,5-difluorophenyl)-2-propenoyl]-4-{2-[(3R,3'R)-3',6-dimethyl-1,2-dihydro-1'H-spiro[indole-3,4'-piperidin]-1'-yl]-1-hydroxyethyl}-4-piperidinol; or 1-{1-[(2E)-3-(3,5-difluorophenyl)-2-propenoyl]-4-piperidinyl}-2-(3'-methyl-1,2-dihydro-1'H-spiro[indole-3,4'-piperidin]-1'-yl)ethanol; or a pharmaceutically acceptable salt thereof or an enantiomer thereof.

In another aspect, the present invention is (1S)-2-(6-chloro-1,2-dihydro-1'H-spiro[indole-3,4'-piperidin]-1'-yl)-1-{1-[(2E)-3-(3,5-difluorophenyl)-2-propenoyl]-4-piperidinyl}ethanol.

In another aspect, the present invention is a benzoate salt of (1S)-2-(6-chloro-1,2-dihydro-1'H-spiro[indole-3,4'-piperidin]-1'-yl)-1-{1-[(2E)-3-(3,5-difluorophenyl)-2-propenoyl]-4-piperidinyl}ethanol.

As used herein, $C_1$-$C_6$-alkyl and $C_1$-$C_4$-alkyl refer to straight or branched hydrocarbon chains containing the specified number of carbon atoms. Examples include methyl, ethyl, n-propyl, n-butyl, isobutyl, isopropyl, t-butyl, and 1,1-dimethylpropyl.

Examples of $C_1$-$C_4$-alkoxy include methoxy, ethoxy, n-propoxy, prop-2-oxy, n-butoxy, but-2-oxy, 2-methylprop-1-oxy, and 2-methylprop-2-oxy.

Examples of hydroxy-$C_1$-$C_6$-alkyl include hydroxymethyl, 2-hydroxyethyl, 1-hydroxyethyl, 3-hydroxypropyl, 2-hydroxypropyl, and 1-hydroxypropyl.

The $R^7$ groups, together with the nitrogen atom to which they are attached, may form a 5- or 6-membered heterocycloalkyl group, examples of which include pyrrolidinyl, morpholino, thiomorpholino, dihydropyridazinyl, piperidinyl, and piperazinyl groups.

As used herein, heteroaryl refers to a 5- or 6-membered aromatic group that contains one or more heteroatoms selected from N, S, and O. Examples of heteroaryl groups include pyridinyl, furyl, thienyl, imidazolyl, pyrrolyl, pyrazolyl, oxazolyl, isoxazolyl, thiazolyl, isothiazolyl, triazolyl, tetrazolyl, and pyrimidinyl groups.

As used herein, "halo" refers to fluoro, chloro, or bromo.

As used herein, the term "a compound" or "the compound" refers to one or more compounds of the present invention. Compounds may exist in crystalline or non-crystalline form, or as a mixture thereof. The skilled artisan will appreciate that pharmaceutically acceptable solvates may be formed for crystalline compounds wherein solvent molecules are incorporated into the crystalline lattice during crystallization. Solvates may involve non-aqueous solvents such as ethanol, isopropanol, DMSO, acetic acid, ethanolamine, and ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The present invention includes all such solvates and forms.

The present invention includes compounds as well as their pharmaceutically acceptable salts. Accordingly, the word "or" in the context of "a compound or a pharmaceutically acceptable salt thereof" is understood to refer to either a compound or a pharmaceutically acceptable salt thereof (alternative), or a compound and a pharmaceutically acceptable salt thereof (in combination).

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication. The skilled artisan will appreciate that pharmaceutically acceptable salts of compounds according to formula (I) may be prepared. These pharmaceutically acceptable salts may be prepared in situ during the final isolation and purification of the compound, or by separately reacting the purified compound in its free acid or free base form with a suitable base or acid, respectively.

Compounds of the present invention can form pharmaceutically acceptable salts by reaction with a suitable acid or base. Suitable acids include inorganic and organic acids; examples of suitable inorganic acids include hydrochloric, hydrobromic, phosphoric, metaphosphoric, nitric, and sulfuric acids; examples of suitable organic acids include tartaric, acetic, trifluoroacetic, citric, malic, lactic, fumaric, benzoic, formic, propionic, glycolic, gluconic, maleic, succinic, methanesulfonic, ethanesulfonic, stearic, benzenesulfonic, bromobenzenesulfonic, and p-toluenesulfonic acids. Suitable bases include, for example, hydroxides, carbonates, hydrides, and alkoxides including NaOH, KOH, $Na_2CO_3$, $K_2CO_3$, NaH, and potassium-t-butoxide.

Compounds of the present invention may exist in stereoisomeric forms. More particularly, compounds of the present invention contain a hydroxyethylene linker between piperidinyl groups that may be prepared as a racemic mixture or as individual enantiomers. The enantiomers may be resolved using a suitable agent such as (S,S)—Co(Salen) or (R,R)—Co(Salen). Accordingly, the individual stereoisomers and mixtures thereof are included within the scope of the present invention.

In a further aspect, the invention provides a method of treating a disease comprising administering the compound of the present invention or a pharmaceutically acceptable salt thereof to a patient in need thereof, wherein the disease is atherosclerosis, inflammatory pain, influenza, metabolic syndrome, multiple sclerosis, asthma, kidney disease, congestive heart failure, Alzheimer's disease, stroke, Crohn's disease, inflammatory bowel disease, endometriosis, or diabetes.

While it is possible that a compound of the present invention may be administered as the pure chemical, it is generally preferable to present the active ingredient as a pharmaceutical formulation. Accordingly, in a further aspect, the invention provides a pharmaceutical composition comprising a compound of formula (I) or a pharmaceutically acceptable salt thereof together with one or more pharmaceutically acceptable carriers or diluents. The carrier(s), diluent(s) and/or excipient(s) must be acceptable in the sense of being compatible with the other ingredients of the formulation and not deleterious to the patient.

Compounds of the present invention may be administered in conventional dosage forms prepared by combining a compound of the invention with standard pharmaceutical carriers, diluents, or excipients according to conventional procedures well known in the art. These procedures may involve mixing, granulating and compressing, or dissolving the ingredients as appropriate to the desired preparation.

The compositions may be in the form of tablets, capsules, powders, granules, lozenges, creams, or liquid preparations, such as oral or sterile parenteral solutions or suspensions.

Tablets and capsules for oral administration may contain conventional excipients including binding agents, fillers, lubricants, disintegrants, and wetting agents such as those well known in the art. The tablets may be coated according to methods well known in the art.

Affinity for CCR2 Receptor

Compounds of the present invention have been found to exhibit affinity for chemokine receptors, in particular the CCR2 receptor. Such affinity is typically calculated from the $IC_{50}$ as the concentration of a compound necessary to inhibit 50% of the stimulated response from the receptor in an appropriate assay, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In the context of the present invention pKi (corresponding to the antilogarithm of Ki) is used instead of Ki.

CCR-2 [$^{35}$S] GTPgS SPA Binding Assay

Membrane Preparation

CHO cells expressing the human CCR-2 receptor were grown in DMEM F12 media supplemented with 10% foetal calf serum, 2 mM L-glutamine, G418 at 37° C. in a 5% $CO_2$ atmosphere. Confluent cells were harvested using Hanks buffered salt solution (HBSS, $Ca^{2+}$, $Mg^{2+}$ free) containing 0.6 mM EDTA. The resulting cell suspension was centrifuged at 300 g at 4° C. for 10 min, cell pellet resuspended in 100 mL HBSS+EDTA and respun at 300 g for 5 min. The resulting cell pellet was resuspended in 50 mM HEPES containing 100 mM leupeptin, 25 µg/mL bacitracin, 1 mM EDTA, 1 mM PMSF and 2 µM pepstain A, at pH 7.4. The suspension was homogenised using an ice cold blender and centrifuged at 500 g for 20 min. The supernatant was withdrawn and spun at 48000 g for 30 min. This cell pellet was resuspended in the above buffer minus the pepstatin A and PMSF and stored in aliquots at −70° C.

Assay

For the assay, membranes were thawed and re-suspended in assay buffer (20 mM HEPES, 10 mM $MgCl_2$, 100 mM NaCl, pH 7.4, containing 1 mg/mL saponin, 10 mM GDP) to give a final concentration of 5 μg/well. The membranes were pre-coupled with LEADseeker SPA beads (0.25 mg/well) for 30 min at room temperature while mixing. Assay plates containing 0.5 μL of various test compounds (30 μM-30 pM) in 100% DMSO as 11 point, four fold dilutions across a 384 well plate were used in the assay which have been prepared on a Biomek FX. The plate also contained 16 wells of DMSO and 16 wells of a high concentration of a standard antagonist to produce high and low controls in the experiment. To this 15 μL of bead and membrane mix were added with, 15 μL [$^{35}$S] GTPgS (0.2 nM final assay concentration) and 15 μL of an EC$_{80}$ (40 nM) of MCP-1. This concentration of MCP-1 had been pre-determined from agonist curves run against this receptor. All additions were made using a multidrop. Plates were then sealed and centrifuged for 5 min at 300 rpm before they were left to incubate at room temperature for 3 hours. After this time they were read on a Viewlux imaging system. For data handling the high and low controls wells were used to normalize the data, which was then fitted using a 4 parameter kit in Excel.

The assay described above has an effective lower limit of detection of pKi ~10 and is believed to have an effective upper limit of detection of in the region of 5.0-5.5. Using this assay, all of the exemplified compounds exhibited a pKi of ≧6.

Schemes

The following schemes illustrate how compounds of the present invention can be prepared. The specific solvents and reaction conditions referred to are also illustrative and are not intended to be limiting. Compounds not described are either commercially available or are readily prepared by one skilled in the art using available starting materials.

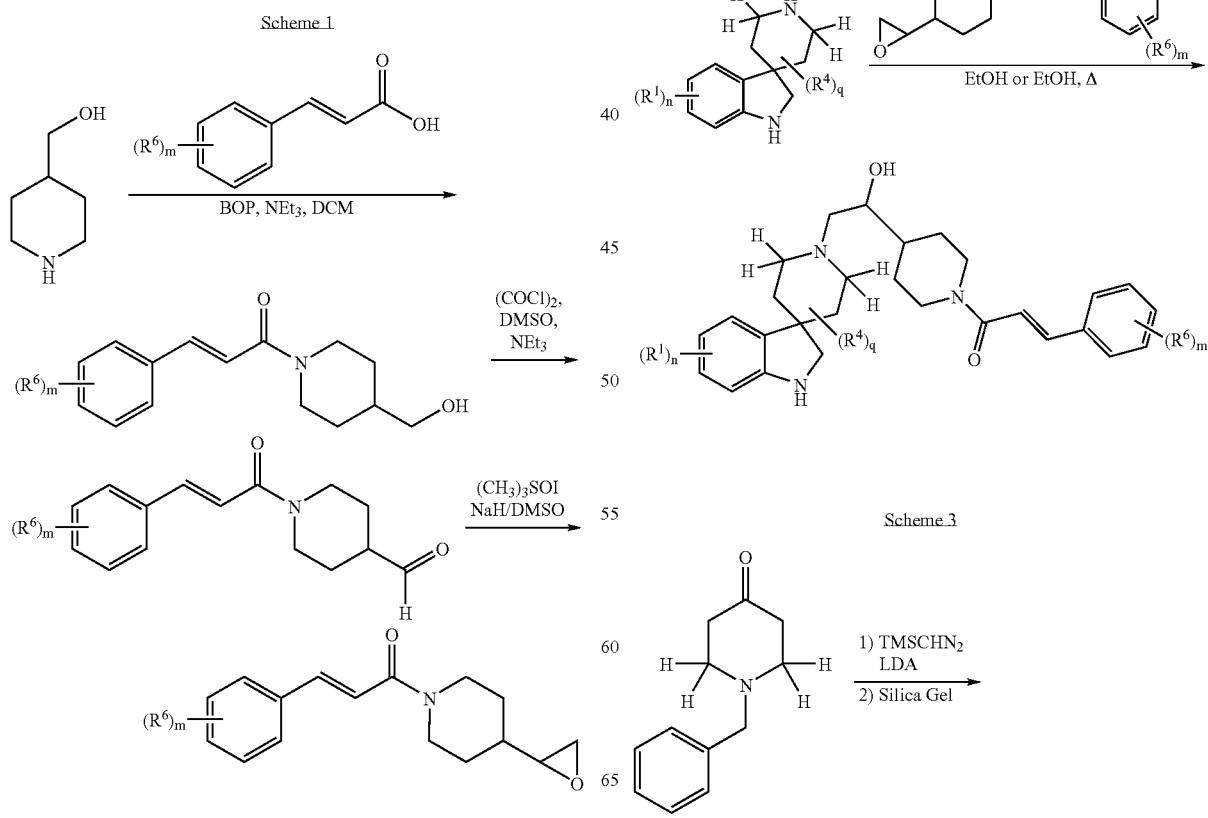

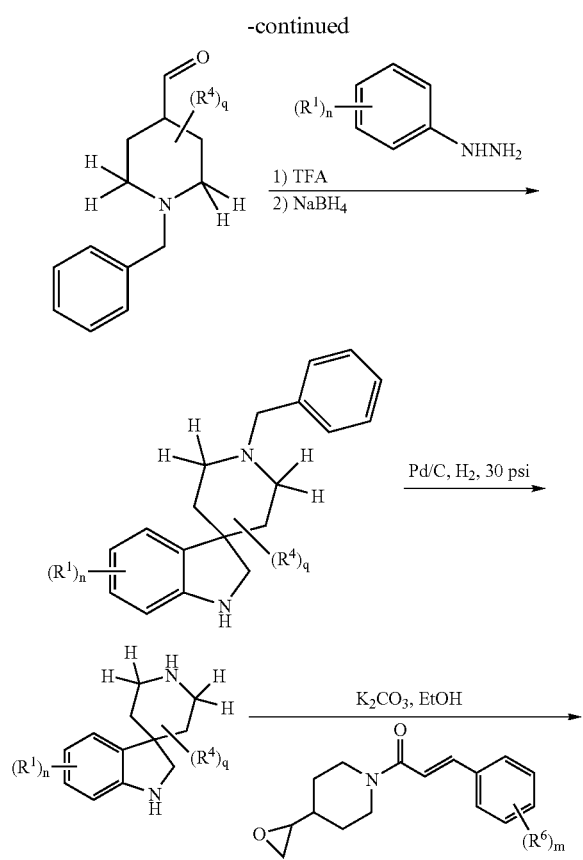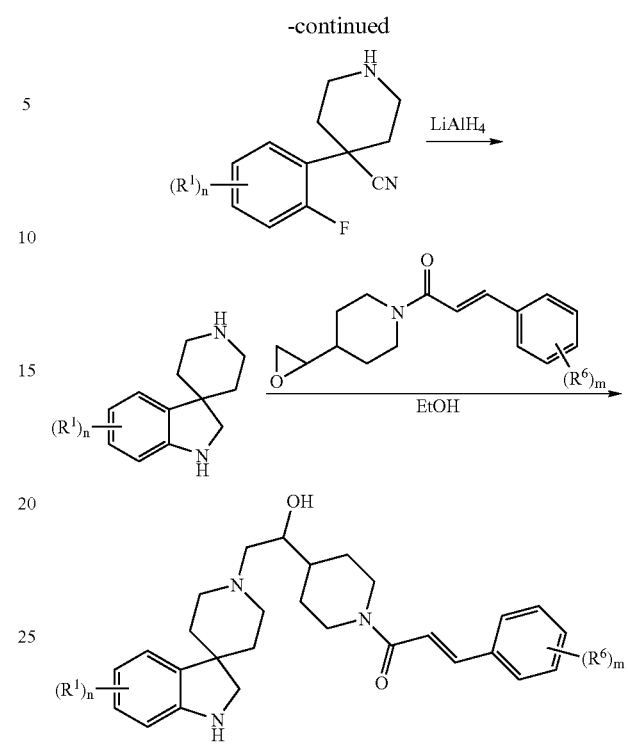
Scheme 4
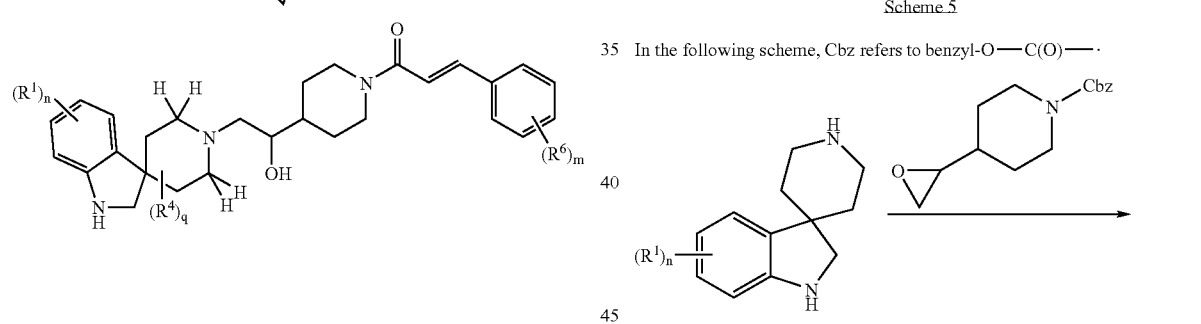
Scheme 5
In the following scheme, Cbz refers to benzyl-O—C(O)—.
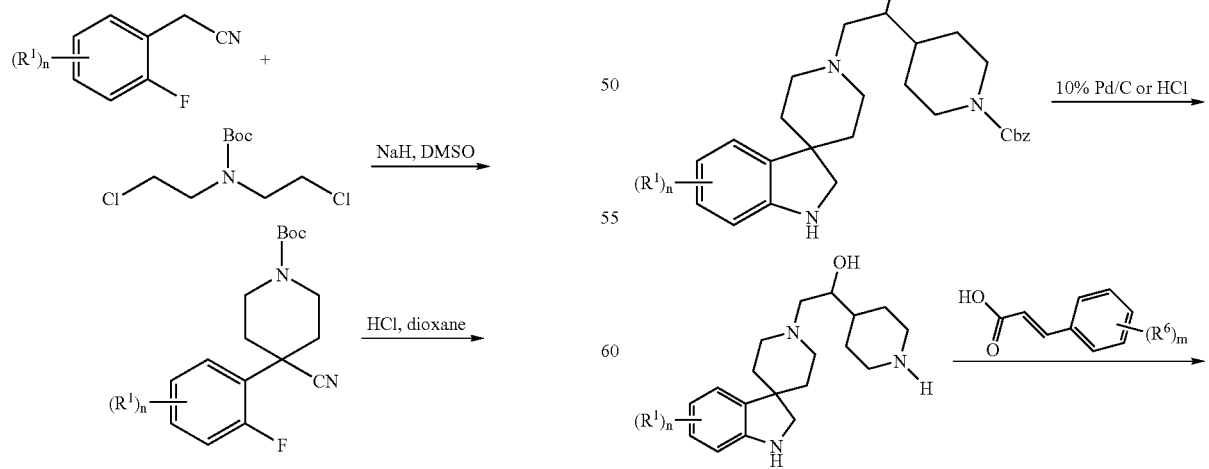

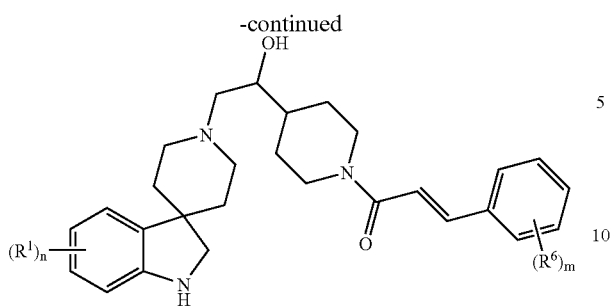
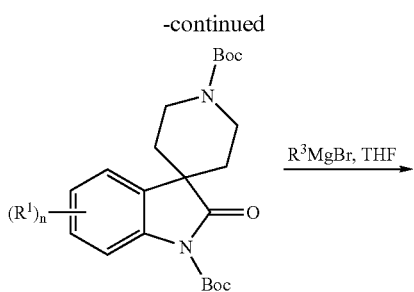
Scheme 6
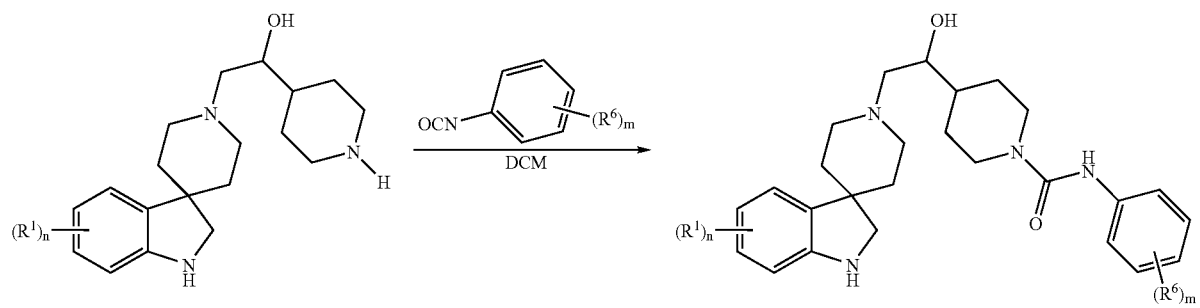
Scheme 7
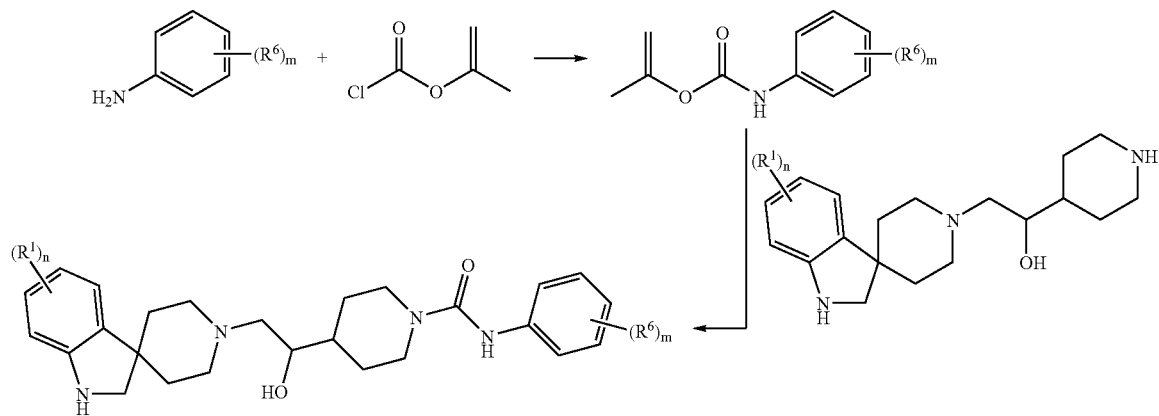
Scheme 8
In the following scheme, DMAP refers to 4-dimethylaminopyridine.
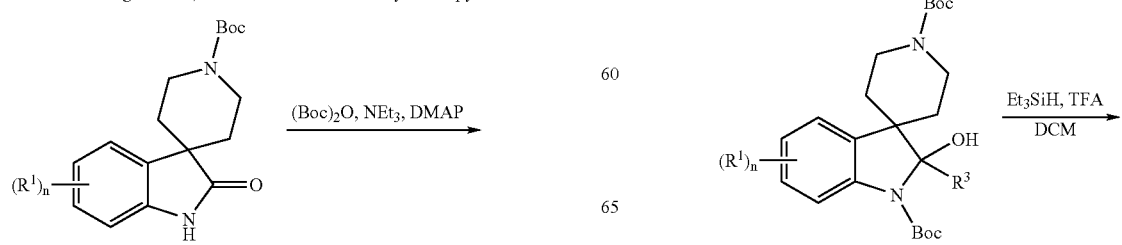

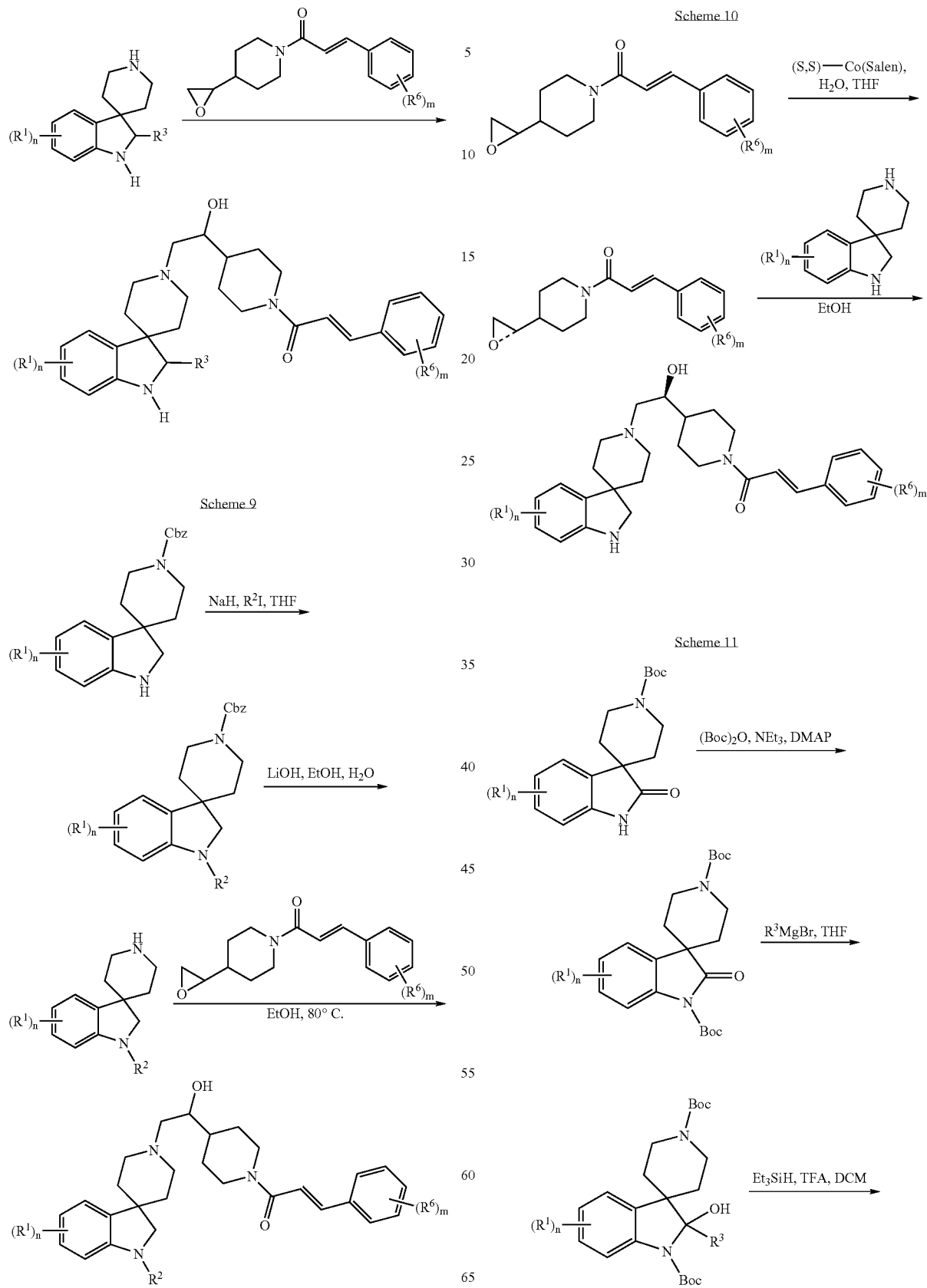

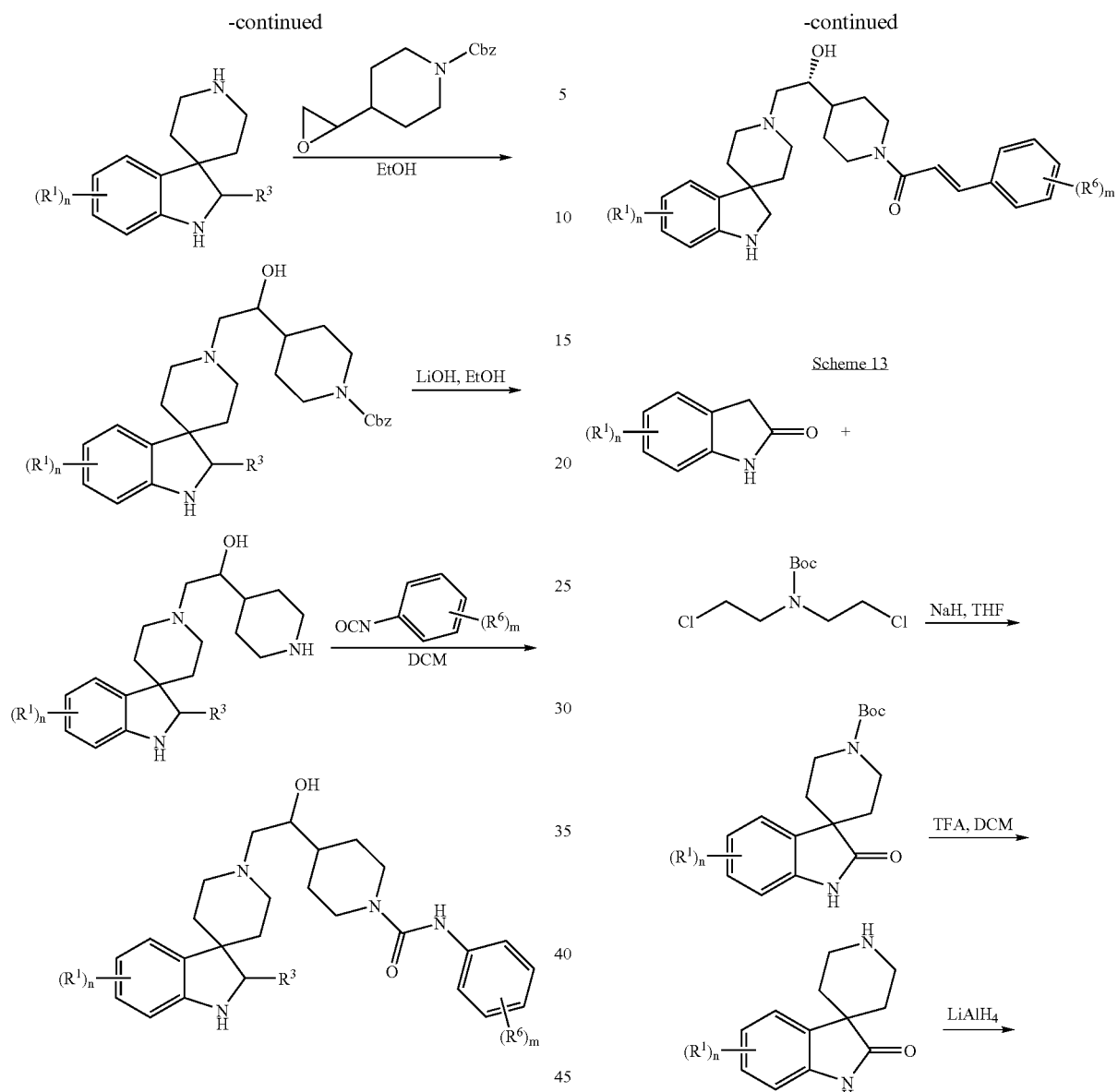
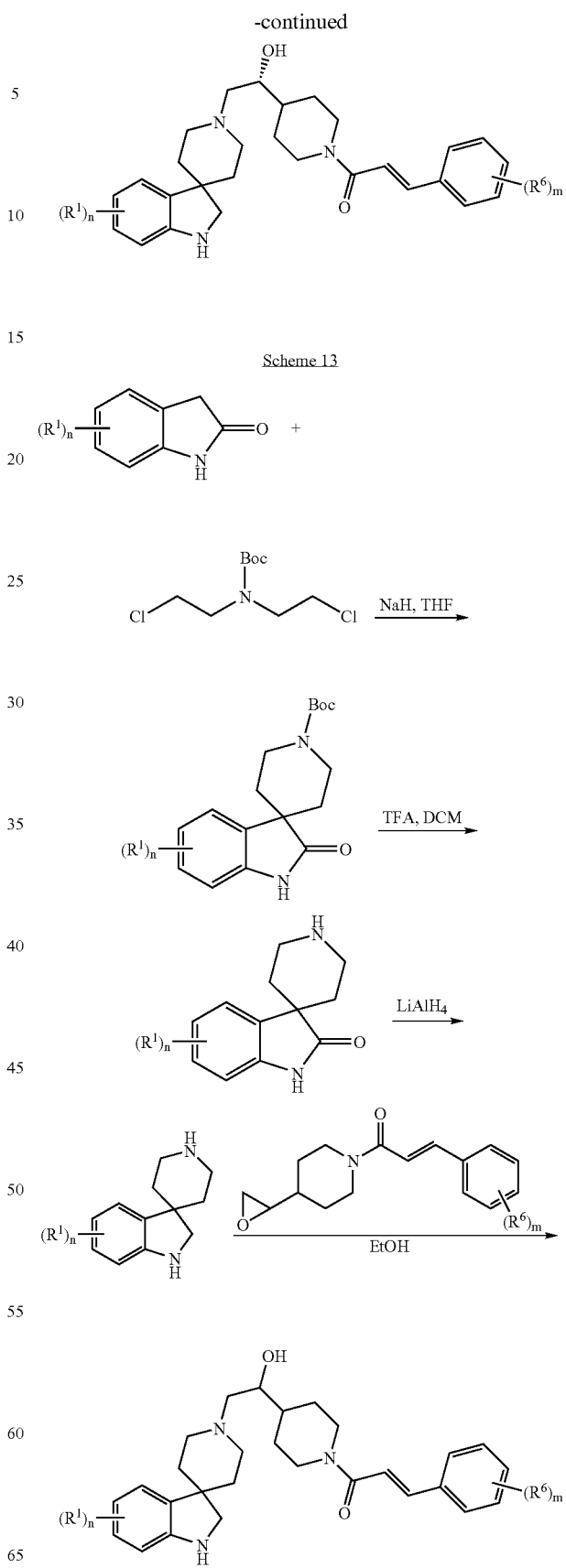

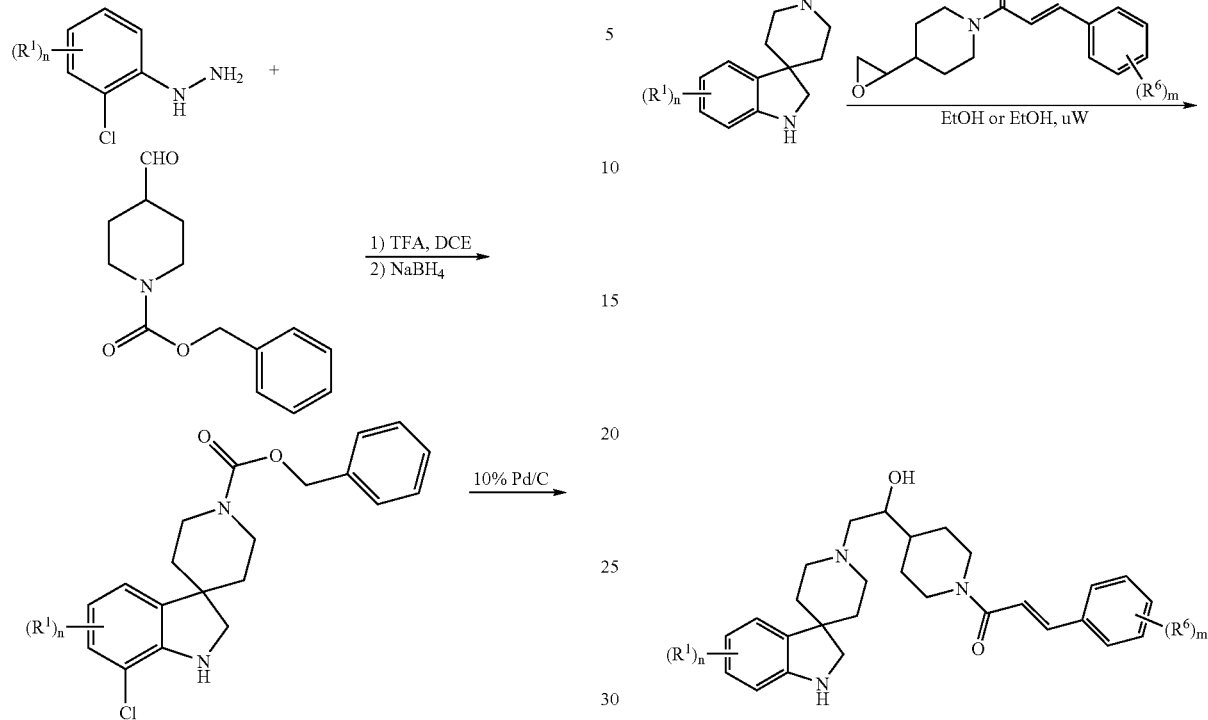
Scheme 14
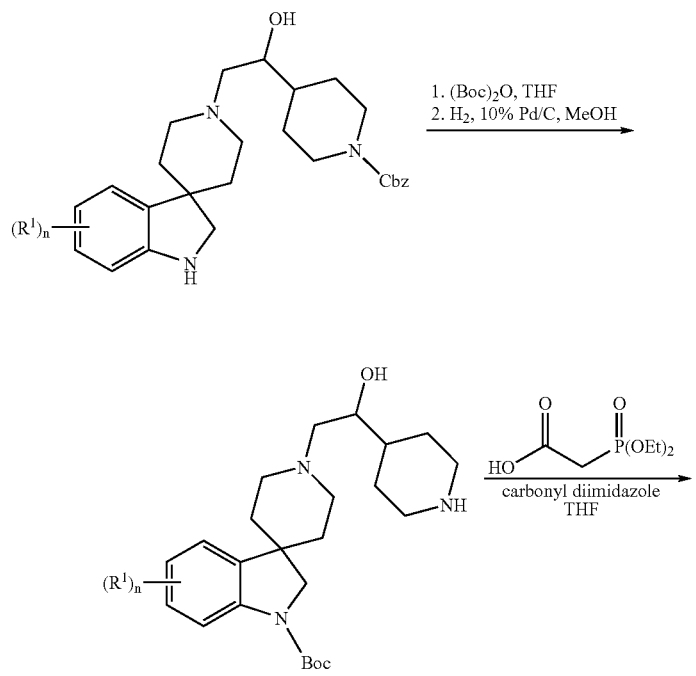
Scheme 15
In the following scheme, DBU refers to 1,8-diazabicyclo[5.4.0.]undec-7ene.

-continued
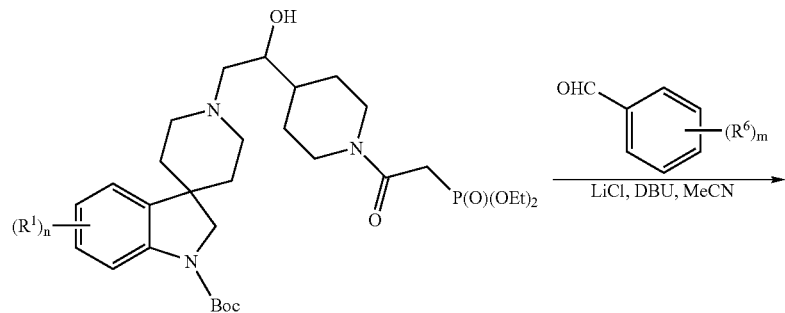
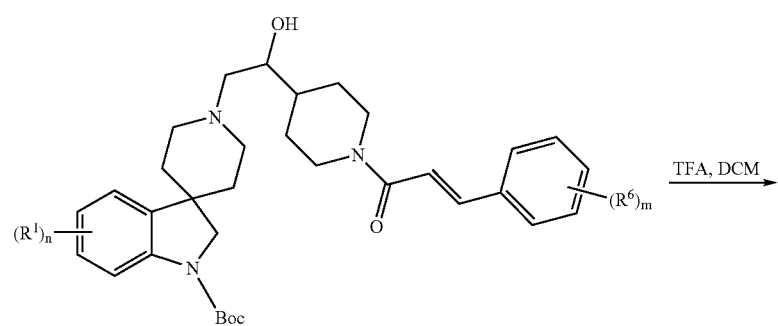
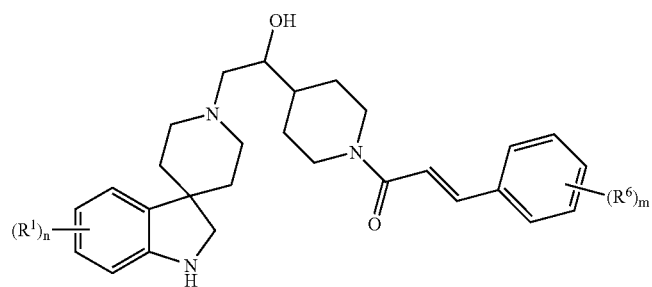
Scheme 16
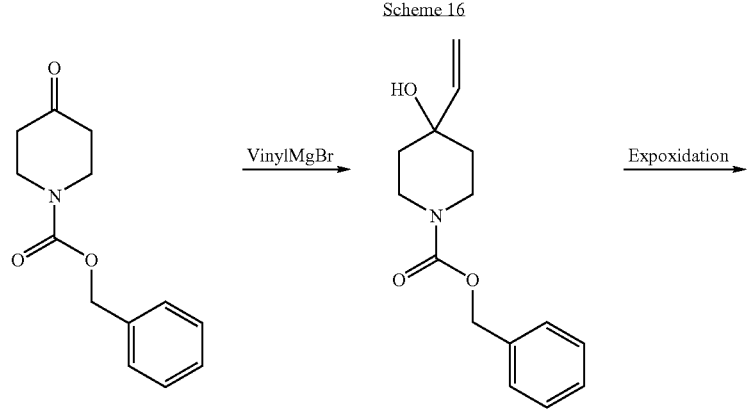

-continued
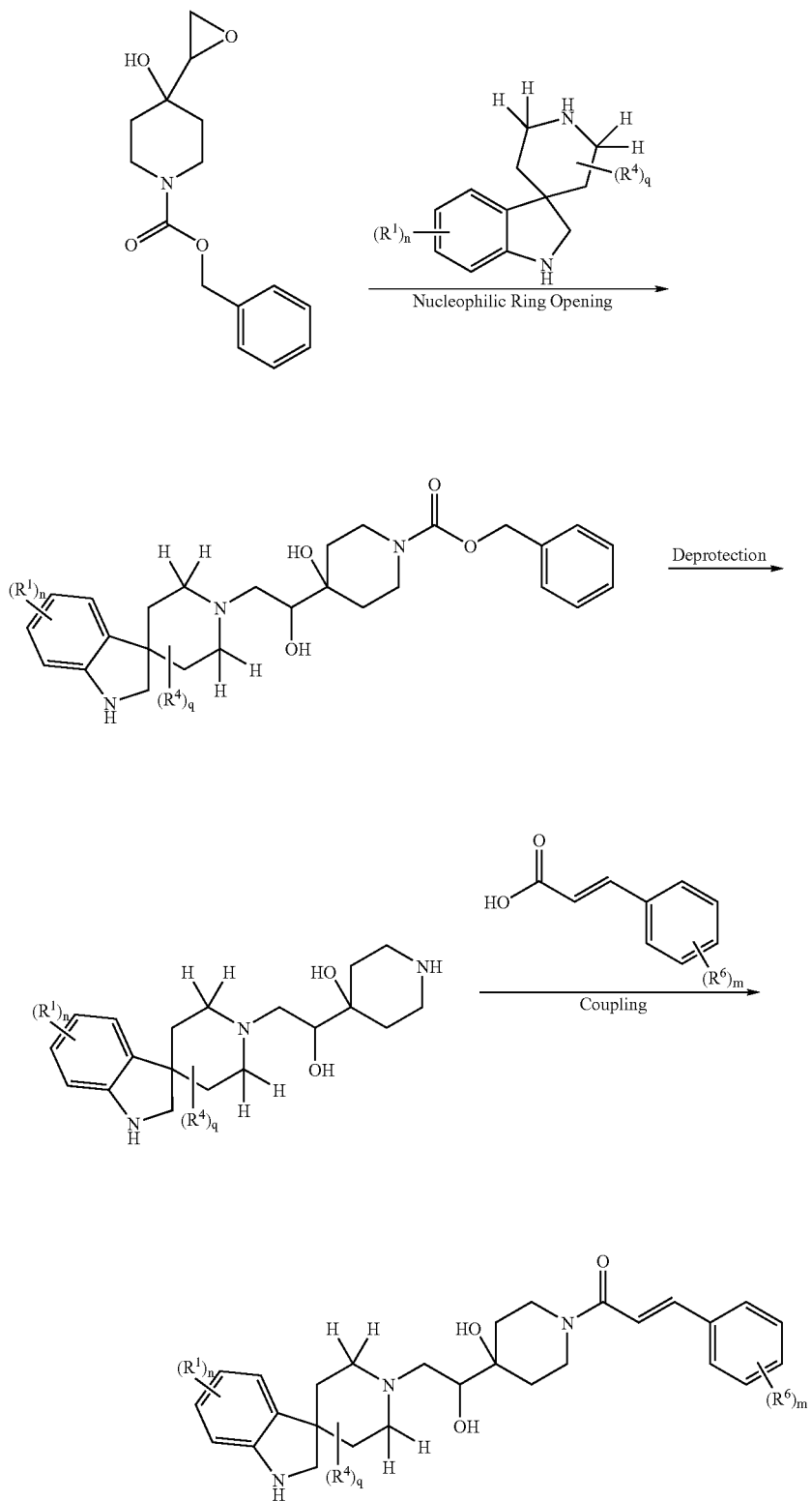

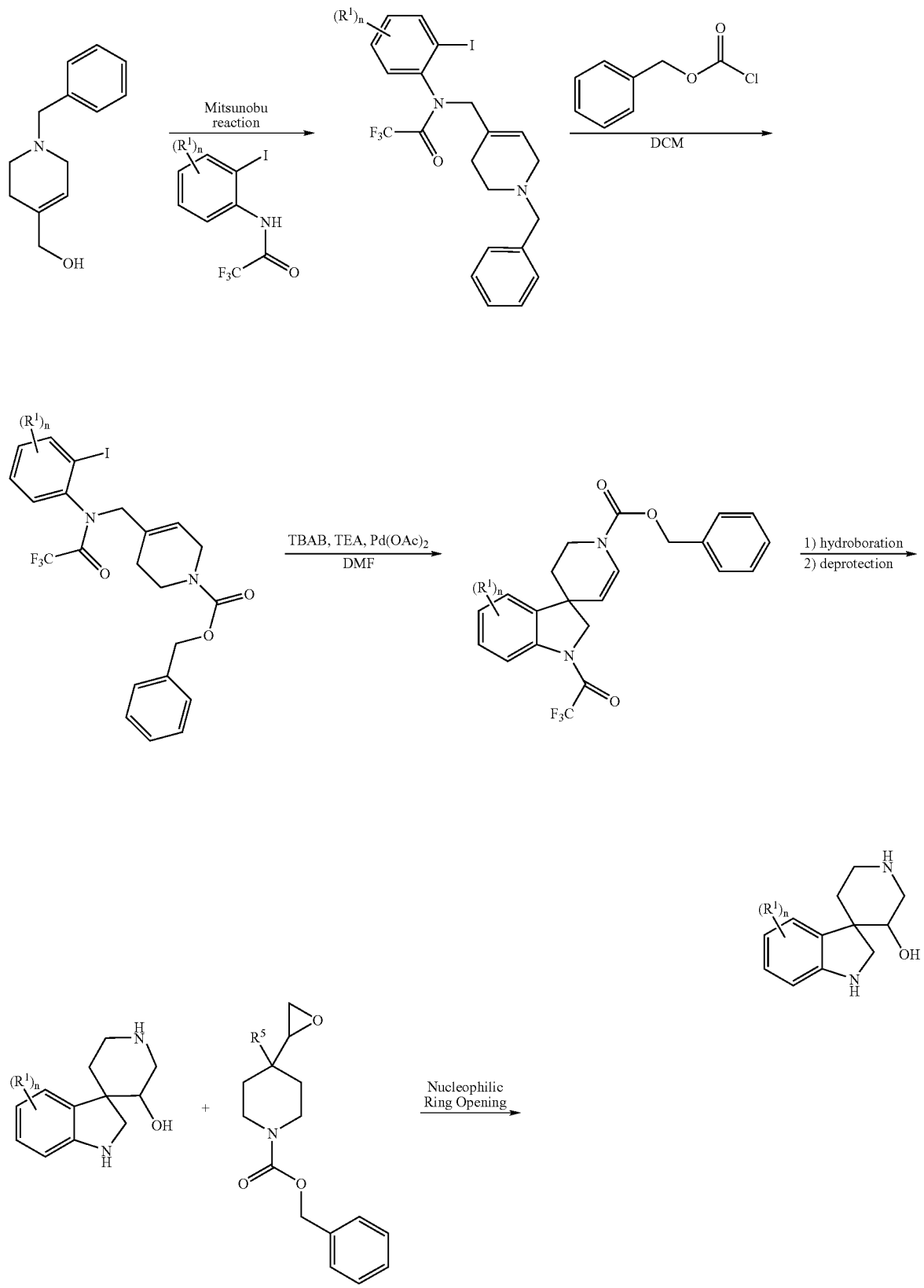
Scheme 17
In the following scheme, TBAB refers to tetra-n-butylammonium bromide.

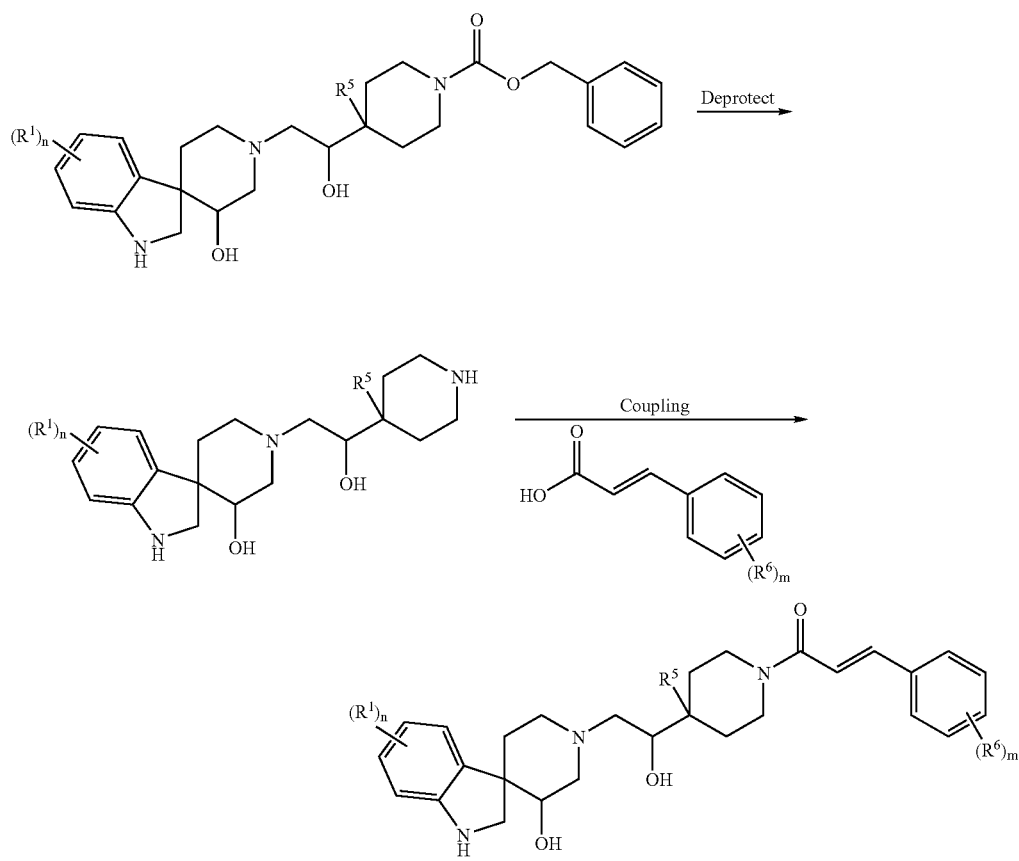
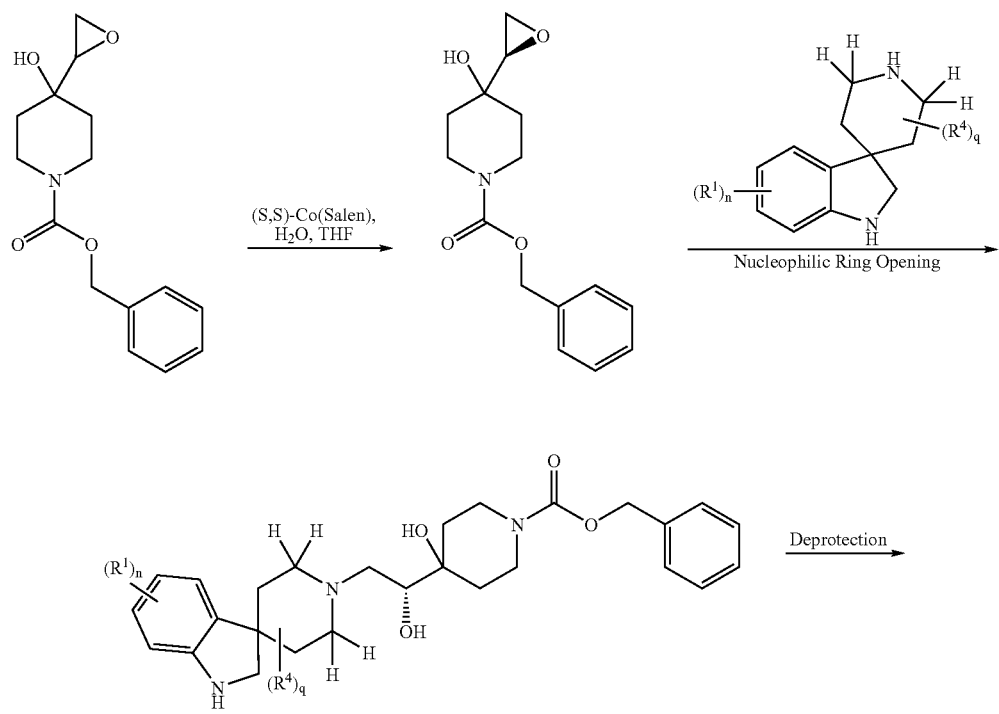
Scheme 18

-continued
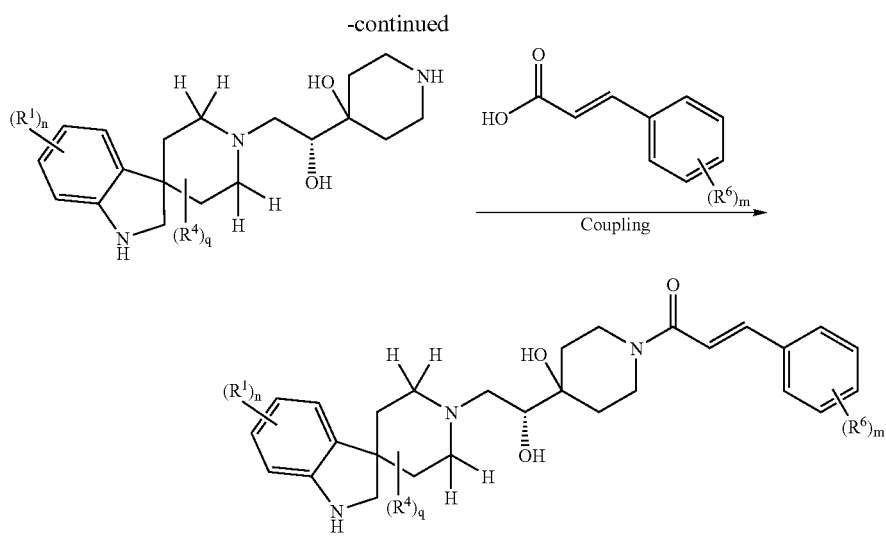
Scheme 19
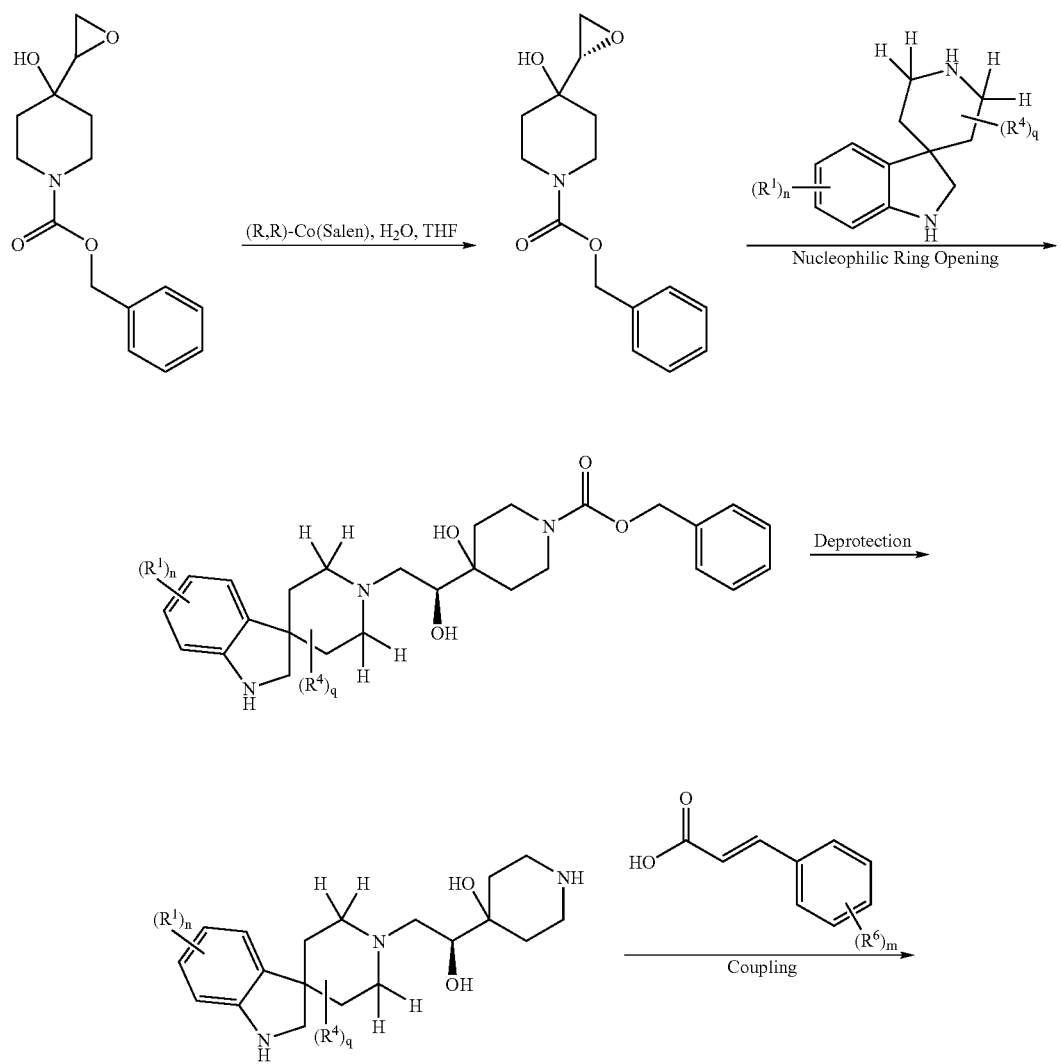

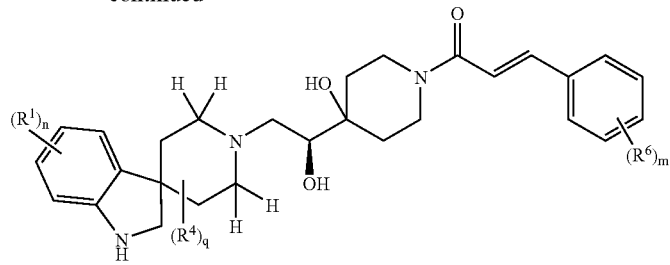
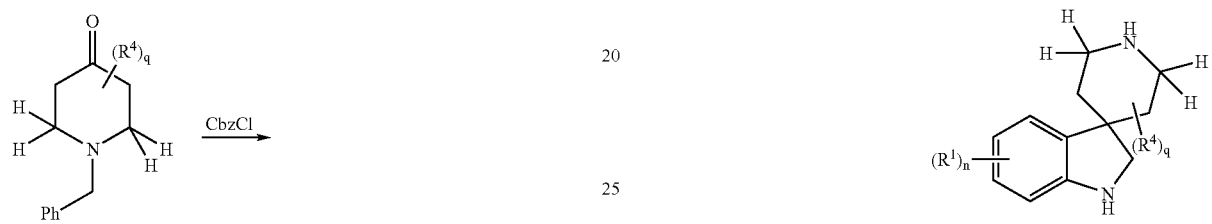
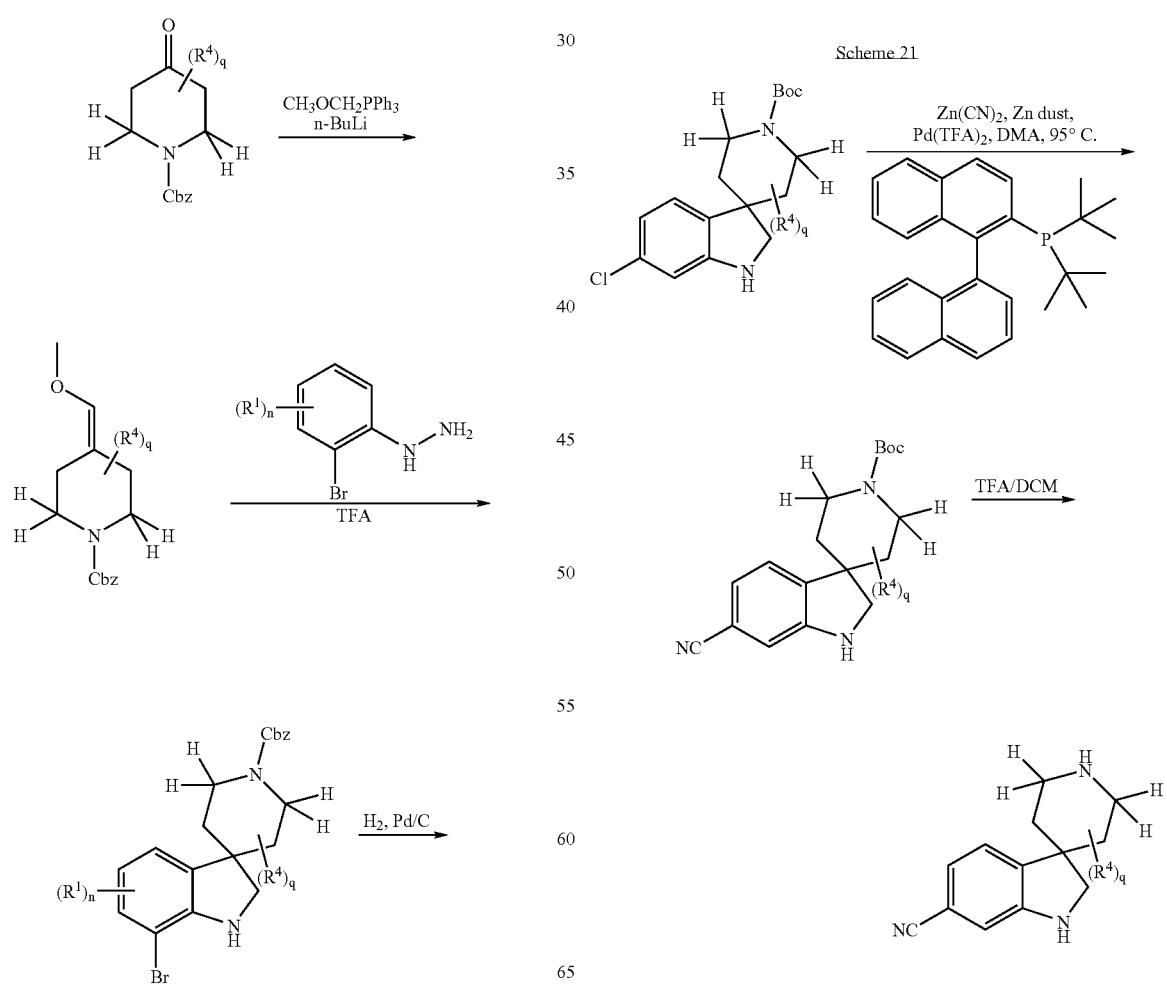

Scheme 22
In the following scheme, HOBt refers to hydroxybenzotriazole and NMO is N-methylmorpholine-N-oxide.
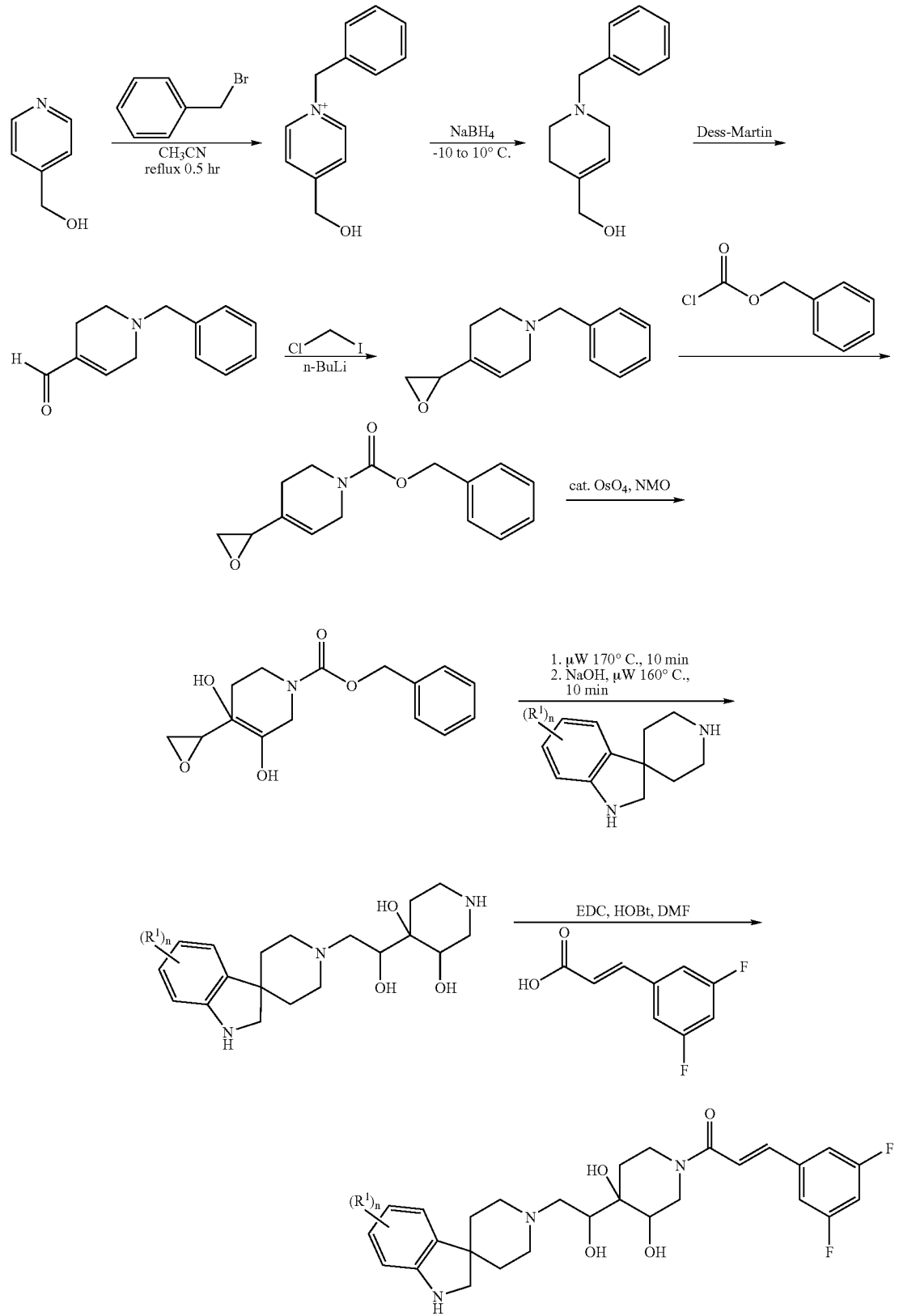

Scheme 23

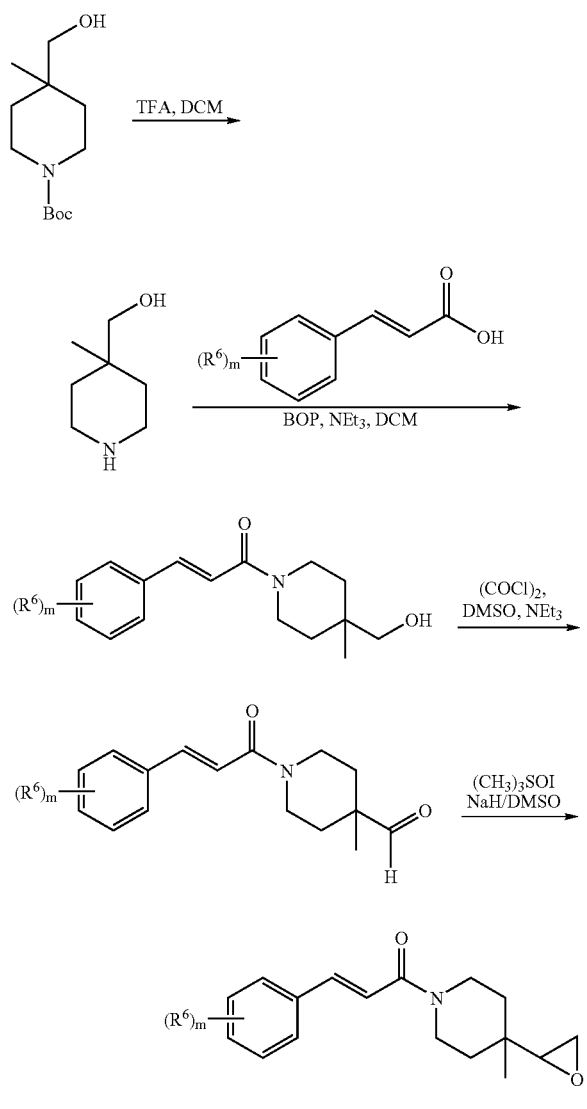

EXAMPLES

The following examples are for illustrative purposes only and are not intended to limit the scope of the invention. The compounds were named using ACD Name Pro 6.02 software (Advanced Chemistry Development).

Mass spectra were obtained using either a Waters ZQ mass spectrometer or Micromass Platform 2 mass spectrometer or Agilent LC/MSD mass spectrometer and electro-spray ionization to observe either MH+ or M−. Proton Nuclear Magnetic Resonance ($^1$H-NMR) spectra were recorded at 400 MHz unless otherwise stated, chemical shifts are reported in ppm downfield from Me$_4$Si, used as internal standard, and are assigned as singlets (s), doublets (d), doublets of doublets (dd), triplets (t), doublet of triplets (dt), quartets (q) multiplets (m) or are otherwise described in full. The prefix "br" refers to a broad peak; for example, a broad singlet may appear as br.s (or br s).

Intermediate 1: {1-[(2E)-3-(3,5-Difluorophenyl)-2-propenoyl]-4-piperidinyl}methanol

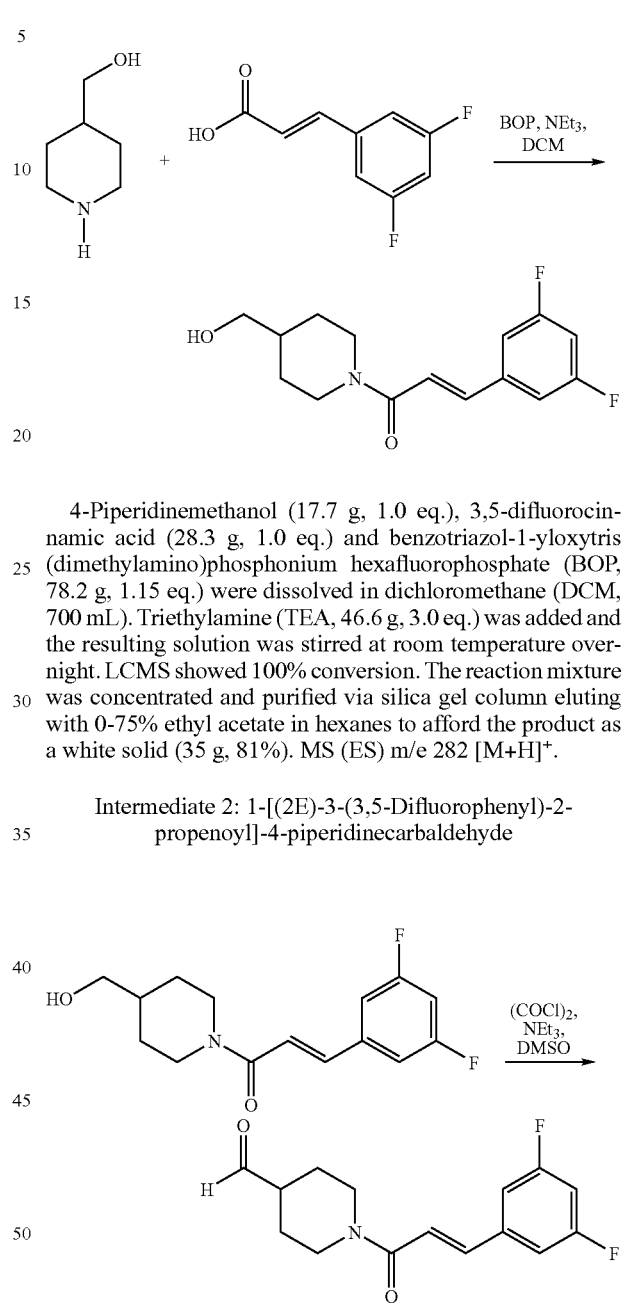

4-Piperidinemethanol (17.7 g, 1.0 eq.), 3,5-difluorocinnamic acid (28.3 g, 1.0 eq.) and benzotriazol-1-yloxytris(dimethylamino)phosphonium hexafluorophosphate (BOP, 78.2 g, 1.15 eq.) were dissolved in dichloromethane (DCM, 700 mL). Triethylamine (TEA, 46.6 g, 3.0 eq.) was added and the resulting solution was stirred at room temperature overnight. LCMS showed 100% conversion. The reaction mixture was concentrated and purified via silica gel column eluting with 0-75% ethyl acetate in hexanes to afford the product as a white solid (35 g, 81%). MS (ES) m/e 282 [M+H]$^+$.

Intermediate 2: 1-[(2E)-3-(3,5-Difluorophenyl)-2-propenoyl]-4-piperidinecarbaldehyde A 2-L round bottom flask was charged with DCM (900 mL) and oxalylchloride (25.36 g, 0.20 mole, 1.3 eq.) and cooled to −78° C. Dimethylsulfoxide (DMSO, 31.22 g, 0.40 mole, 2.6 eq.) was added dropwise and the mixture was stirred at −78° C. for 10 min. Then, {1-[(2E)-3-(3,5-difluorophenyl)-2-propenoyl]-4-piperidinyl}methanol (43.2 g, 0.15 mole, 1.0 eq, dissolved in 100 mL of DCM and a few mL DMSO) was added slowly. After stirring for another 30 min at −78° C., TEA (93.14 g, 0.92 mole, 6.0 eq.) was added slowly. The suspension was then stirred at −78° C. for 30 min, then warmed to room temperature over 2 h. The mixture was diluted with 300 mL DCM and washed with 2×200 mL 2M HCl, 1×100 mL saturated NaHCO$_3$, and then dried over MgSO₄, and concentrated to afford 1-[(2E)-3-(3,5-difluorophenyl)-2-propenoyl]-4-piperidinecarbaldehyde (35.4 g, 82%) as a brown oil. The material was used in the next step without further purification. MS (ES) m/e 280 [M+H]⁺. ¹HNMR (CDCl₃) δ(ppm): 9.72 (s, 1H), 7.56 (d, 1H), 7.04 (m, 2H), 6.90 (d, 1H), 6.82 (m, 1H), 4.40 (m, 1H), 4.00 (m, 1H), 3.36 (m, 1H), 3.22 (m, 1H), 2.56-2.64 (m, 1H), 2.02 (m, 2H), 1.67 (m, 2H).

Intermediate 3: 1-[(2E)-3-(3,5-Difluorophenyl)-2-propenoyl]-4-(2-oxiranyl)piperidine

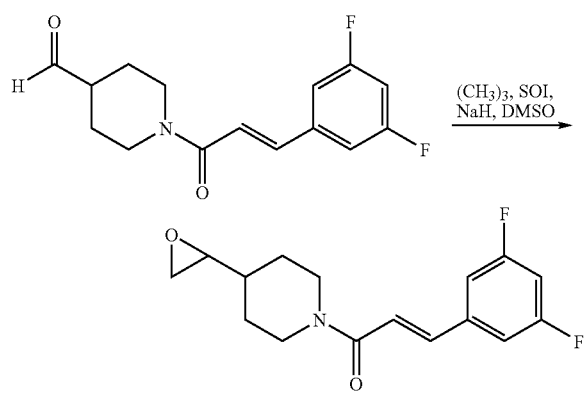

An oven dried 500-mL flask was charged with (CH₃)₃SOI (46.14 g, 210 mmol, 1.3 eq) and 250 mL dry DMSO. NaH (95%, 5.30 g, 210 mmol, 1.3 eq) was added in around 10 batches and solution was then cooled to 0° C. The resulting mixture was stirred at 0° C. for 30 min. The aldehyde (Intermediate 2, 45 g, 161 mmol, 1.0 eq) in 150 mL dry DMSO solution was added dropwise and the resulting solution was stirred at 0° C. for 30 min. LCMS showed completed reaction. The reaction was then quenched with 800 mL water and poured into 1200 mL diethyl ether. The organic layer was separated and washed with 2×150 mL water and dried over MgSO₄ and concentrated. Crude LCMS showed >90% purity for the desired product in 58% yield as a light yellow oil which solidified to a yellow solid overnight. MS (ES) m/e 294 [M+H]⁺. ¹HNMR (CDCl₃) δ(ppm): 7.56 (d, 1H), 7.04 (dd, 2H), 6.91 (d, 1H), 6.80 (m, 1H), 4.74 (m, 1H), 4.11 (m, 1H), 3.05 (m, 1H), 2.77 (s, 2H), 2.61 (m, 1H), 1.95 (m, 1H), 1.70-1.80 (m, 1H), 1.30-1.60 (m, 4H).

Intermediate 4: Phenylmethyl 4-(2-oxiranyl)-1-piperidinecarboxylate

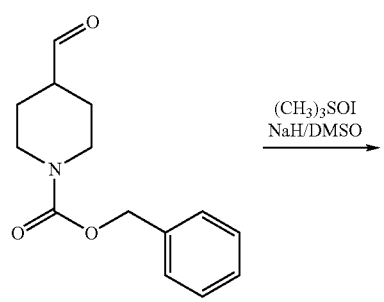

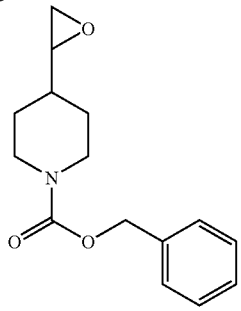

Trimethylsulfoxonium iodide (1.65 g, 7.5 mmol) was added in two portions to a solution of NaH (300 mg, 7.5 mmol) in anhydrous DMSO (10 mL) at room temperature. The resulting mixture was stirred for 1 hour, whereupon a solution of phenylmethyl 4-formyl-1-piperidinecarboxylate (1.24 g, 5.0 mmol) in anhydrous DMSO (10 mL) was added. The reaction mixture was stirred at room temperature for 2 hours, then poured into cold water (100 mL), and extracted with Et₂O (2×100 mL). The extracts were combined, washed with water, brine, and dried (Na₂SO₄). The solvent was removed in vacuo to give the title compound (0.95 g, 73%) as a colorless oil. MS (ES) m/e 262 [M+H]⁺.

Intermediate 5: Phenylmethyl 6-chloro-1,2-dihydro-1'H-spiro[indole-3,4'-piperidine]-1'-carboxylate (3-Chlorophenyl)hydrazine (1.3 g, 7.3 mmol, 1 eq.) was mixed with phenylmethyl 4-formyl-1-piperidinecarboxylate (1.8 g, 7.3 mmol, 1 eq.) in DCM with trifluoroacetic acid (TFA, 8.3 g, 73 mmol, 10 eq.) and refluxed with stirring for ½ h. Sodium borohydride (0.831 g, 21.8 mmol, 3 eq.) was then added to the mixture and after 10 min the mixture was transferred to an ice water bath. Excess 28-30% ammonium hydroxide was then added portionwise followed by water. The mixture was shaken and the organic layer separated and dried over sodium sulfate followed by evaporation. The residue was loaded onto silica and purified by normal phase chromatography, eluting with 15, 20, 25% EtOAc/hexanes, eluting first the desired 6-Cl isomer followed by the 4-Cl isomer. The 6-Cl isomer was isolated for further use. MS (ES) m/e 357 [M+H]+.

Intermediate 6: 1,1-Dimethylethyl 4-(4-chloro-2-fluorophenyl)-4-cyano-1-piperidinecarboxylate

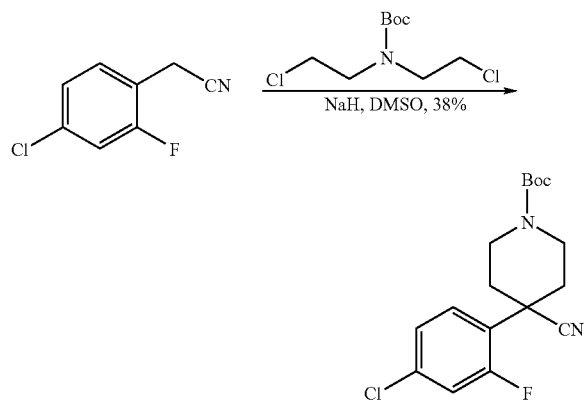

(4-Chloro-2-fluorophenyl)acetonitrile (2.3 g, 13.7 mmol, 1.0 equiv) was added to a suspension of NaH (2.1 g, 52.5 mmol, 3.8 equiv) in DMSO (20 mL) at 23° C. The resulting yellow suspension was stirred for 10 min and the color turned red-brown. Boc-N(CH₂CH₂Cl) (N,N-bis(2-chloroethyl)-t-butylcarbamate) (3.7 g, 15.3 mmol, 1.1 equiv) in DMSO (20 mL) was added to the reaction mixture (bubbling observed) and the resulting suspension was heated to 85° C. with stirring for an additional 1.5 hours. The reaction mixture was cooled to 23° C. then poured onto a 1:1 mixture of ethyl acetate and hexanes (300 mL). The organic fraction was washed with water (100 mL) and a saturated aqueous solution of NaCl (100 mL). The organic layer was dried over anhydrous sodium sulfate. The dried solution was then filtered and the filtrate was concentrated. The residue was purified by flash silica chromatography (0%-30% ethyl acetate in hexanes) to afford the bis-alkylation product 1,1-dimethylethyl 4-(4-chloro-2-fluorophenyl)-4-cyano-1-piperidinecarboxylate (1.9 g, 5.6 mmol, 38%) as a yellow crystalline solid. MS (ES) m/e 239 [M−Boc+H]+.

Intermediate 7: 6-Chloro-1,2-dihydrospiro[indole-3,4'-piperidine]

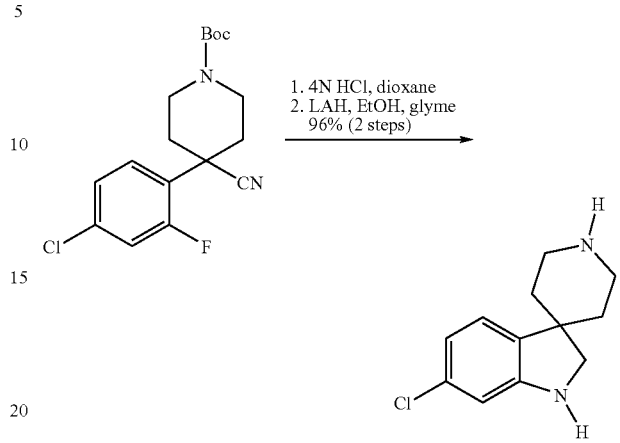

HCl (4.0 N in dioxane, 10 mL, 40 mmol, 7.1 equiv) was added to a solution of 1,1-dimethylethyl 4-(4-chloro-2-fluorophenyl)-4-cyano-1-piperidinecarboxylate (1.9 g, 5.6 mmol, 1 equiv) in 1,4-dioxane (25 mL) at 23° C. The resulting solution was warmed to 45° C. and stirred for 1 hour (white precipitation formed). The suspension was concentrated to afford 4-(4-chloro-2-fluorophenyl)-4-piperidinecarbonitrile as a pale-yellow solid. EtOH (1.6 mL, 38.1 mmol, 6.8 equiv) was slowly added to a suspension of lithium aluminium hydride (LAH) (1.15 g, 30.3 mmol, 5.4 equiv) in glyme (16 mL) at 0° C. The resulting suspension was heated to reflux and stirred for 5 min. A suspension of the newly prepared 4-(4-chloro-2-fluorophenyl)-4-piperidinecarbonitrile in glyme (10 mL) was added in portions. The resulting brown suspension was refluxed for 1 h, then cooled to 0° C. Water (8 mL) was added slowly at 0° C. and the resulting suspension was warmed to room temperature and stirred for 30 min. The suspension was filtered through Celite pad and the solid was rinsed with CH₂Cl₂ (200 mL). The filtrate was dried over anhydrous potassium carbonate. The dried solution was concentrated. The residue was purified by reverse phase C18 column to afford 6-chloro-1,2-dihydrospiro[indole-3,4'-piperidine] as a white powder (1.2 g, 5.4 mmol, 96%). MS (ES) m/e 223 [M+H]+.

Intermediate 7A: 6-Chloro-1,2-dihydrospiro[indole-3,4'-piperidine]—Alternative Synthesis

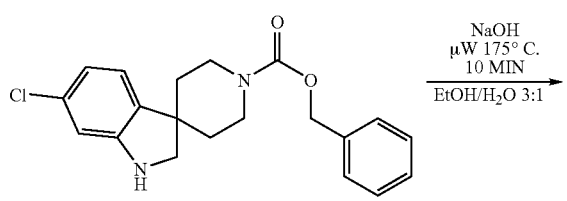

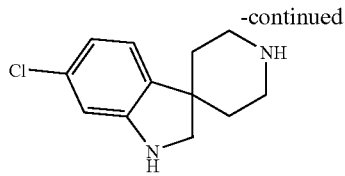

Phenylmethyl 6-chloro-1,2-dihydro-1'H-spiro[indole-3,4'-piperidine]-1'-carboxylate (220 mg, 0.62 mmol, 1 eq.) was mixed with NaOH (100 mg, 2.5 mmol, 4 eq.) in 3 mL EtOH/H$_2$O 3:1 and heated in a microwave reactor at 175° C. for 10 min. The mixture was then added to 1N NaOH (10 mL) and DCM (20 mL). The layers were separated and the aqueous layer was extracted with DCM (4×10 mL). The DCM layers were combined and dried over sodium sulfate followed by evaporation to yield 6-chloro-1,2-dihydrospiro[indole-3,4'-piperidine]. MS (ES) m/e 223 [M+H]$^+$

Example 1

2-(6-Chloro-1,2-dihydro-1'H-spiro[indole-3,4'-piperidin]-1'-yl)-1-{1-[(2E)-3-(3,5-difluorophenyl)-2-propenoyl]-4-piperidinyl}ethanol

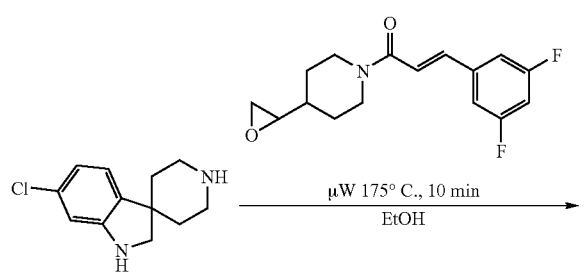

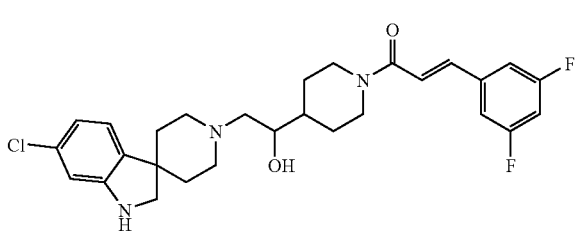

6-Chloro-1,2-dihydrospiro[indole-3,4'-piperidine] (1 eq) was mixed with 1-[(2E)-3-(3,5-difluorophenyl)-2-propenoyl]-4-(2-oxiranyl)piperidine (1 eq) in EtOH (0.5 mL) and heated to 175° C. for 10 min in a microwave reactor. The mixture was then directly purified by HPLC under acidic conditions to yield the product as a trifluoroacetate salt. MS (ES) m/e 516 [M+H]$^+$. $^1$H NMR (DMSO-d$_6$) δ 9.14 (br s, 1H), 7.57 (m, 2H), 7.45 (m, 2H), 7.26 (m, 1H), 6.87 (d, J=8 Hz, 1H), 6.59 (m, 1H), 6.50 (m, 1H), 5.60 (v br s, 1H), 4.55 (m, 1H), 4.40 (m, 1H), 3.76 (m, 1H), 3.45 (m, 4H), 3.10 (m, 6H), 2.63 (m, 1H), 2.19 (m, 1H), 1.99 (m, 1H), 1.80 (m, 3H), 1.64 (m, 2H), 1.20 (m, 2H).

Intermediate 8: Phenylmethyl 4-(2-oxiranyl)-1-piperidinecarboxylate

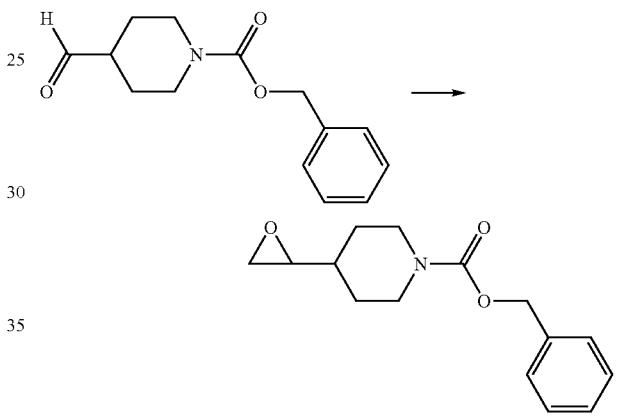

To a solution of NaH (10.4 g, 60% dispersion in mineral oil) in DMSO was added (CH$_3$)$_3$SOI (57 g). The reaction mixture was stirred for 30 min at room temperature followed by the dropwise addition at 0° C. of phenylmethyl 4-formyl-1-piperidinecarboxylate (43 g, which can be purchased from AstaTech, Inc., Bristol, Pa.). The mixture was allowed to stir at room temperature for 1 hour and then quenched with water and extracted with Et$_2$O. The organic layer was washed with H$_2$O, brine, dried over MgSO$_4$, filtered and concentrated to yield a white solid.

Intermediate 9: Phenylmethyl 4-[(2R)-2-oxiranyl]-1-piperidinecarboxylate

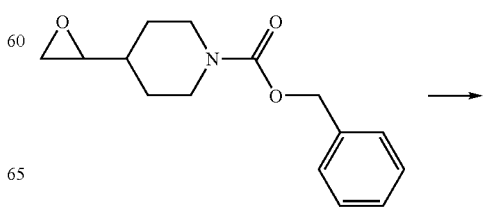

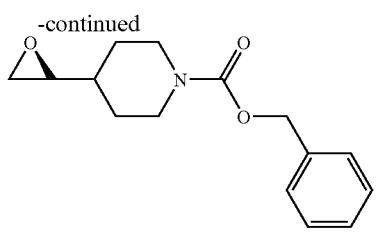

(S,S)-(+)-N,N'-Bis(3,5-di-tert-butylsalicylidene)-1,2-cyclohexanediamino cobalt (II) (1.15 g, 1.9 mmol, 0.025 equiv, CAS 188264-84-8) was dissolved in toluene (20 mL) in an open air flask. Glacial AcOH (219 µL, 3.8 mmol, 0.05 equiv) was added and the reaction was stirred at room temperature for 1 h. The reaction was then concentrated to a solid which was placed under high vacuum until dry. 1-[(2E)-3-(3,5-difluorophenyl)-2-propenoyl]-4-(2-oxiranyl)piperidine (20 g, 76.6 mmol, 1.0 equiv) was dissolved in THF (20 mL). The above catalyst was dissolved in a minimal amount of THF (2 mL) and added to the solution of the racemic epoxide in an open air flask. The mixture was cooled to 0° C. and $H_2O$ (772 uL, 43 mmol, 0.56 equiv) was added dropwise over 5 min. The reaction was warmed to room temperature and allowed to stir overnight. The reaction was then concentrated and purified by flash chromatography on a 120 g silica gel column (0 to 70% EtOAc/hexanes over 60 min.) to yield a white solid (8 g, 40% yield). HPLC m/z [MH]$^+$=294.1; $^1$H NMR (400 MHz, DMSO-d$_6$) d ppm 7.55 (d, J=16 Hz, 1H), 7.03 (m, 2H), 6.91 (m, 1H), 6.81 (m, 1H), 4.74 (m, 1H), 4.13 (m, 1H), 3.15 (m, 1H), 2.79 (m, 4H), 1.90 (m, 1H), 1.47 (m, 4H). A sample of 1-[(2E)-3-(3,5-difluorophenyl)-2-propenoyl]-4-(2-oxiranyl)piperidine from the above reaction was checked on a Chiralpac AD column with a 100% methanol mobile phase (0.9 mL/min) and found to have a retention time of 8.3 min, when compared to a racemic mixture (retention time 8.1 and 8.3 min) and the sample was found to be >99% ee.

Intermediate 10: Phenylmethyl 4-[(1S)-2-(6-chloro-1,2-dihydro-1'H-spiro[indole-3,4'-piperidin]-1'-yl)-1-hydroxyethyl]-1-piperidinecarboxylate

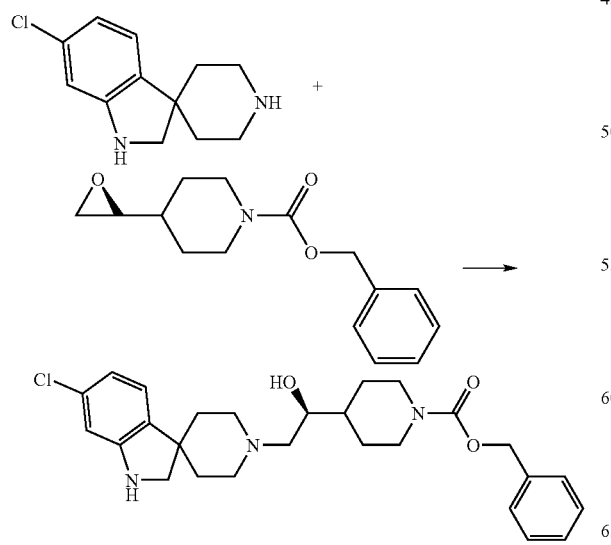

6-Chloro-1,2-dihydrospiro[indole-3,4'-piperidine] (9.68 g, 43.6 mmol, 1.0 equiv) was added to a solution of phenylmethyl 4-[(2S)-2-oxiranyl]-1-piperidinecarboxylate (11.38 g, 43.6 mmol, 1.0 equiv) in EtOH (430 mL) and heated to 80° C. The reaction mixture was allowed to stir at 80° C. overnight followed by concentration. The crude reaction mixture was dissolved in DCE (200 mL) and PL-NCO resin (20 g) was added. The solution was heated to 60° C. for 0.1 h to get rid of residual 6-chloro-1,2-dihydrospiro[indole-3,4'-piperidine]. The mixture was allowed to cool to room temperature and filtered (washed with MeOH, DCM, and Et$_2$O in order). The solution was concentrated to yield product as an off white solid (18.2 g).

Intermediate 11: (1S)-2-(6-Chloro-1,2-dihydro-1'H-spiro[indole-3,4'-piperidin]-1'-yl)-1-(4-piperidinyl)ethanol

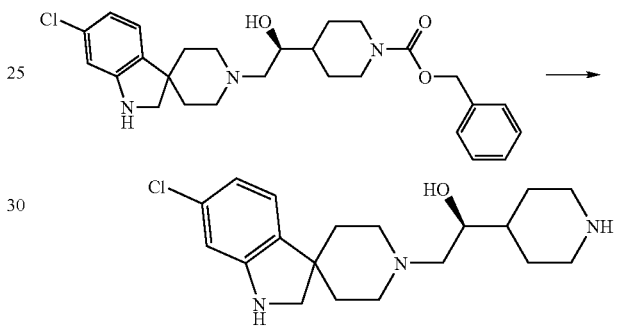

To a 1-L round bottomed flask was added phenylmethyl 4-[(1S)-2-(6-chloro-1,2-dihydro-1'H-spiro[indole-3,4'-piperidin]-1'-yl)-1-hydroxyethyl]-1-piperidinecarboxylate (16.6 g) followed by 6N HCl (345 mL). The solution was heated to 100° C. for ~1 h, and then cooled to room temperature before being transferred to a separatory funnel. The acidic solution was washed with diethyl ether, and then the pH was raised to ~11 with aqueous NH4OH. The basic solution was extracted three times with DCM. The combined organic extracts were dried over Na$_2$SO$_4$, filtered and concentrated under reduced pressure to give the product (9.8 g, 82%) as an off white solid.

Example 2

(1S)-2-(6-Chloro-1,2-dihydro-1'H-spiro[indole-3,4'-piperidin]-1'-yl)-1-{1-[(2E)-3-(3,5-difluorophenyl)-2-propenoyl]-4-piperidinyl}ethanol

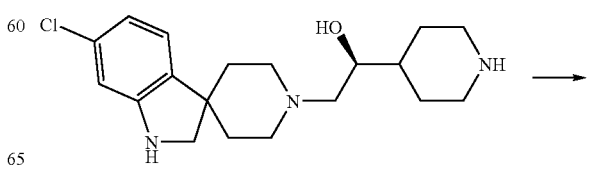

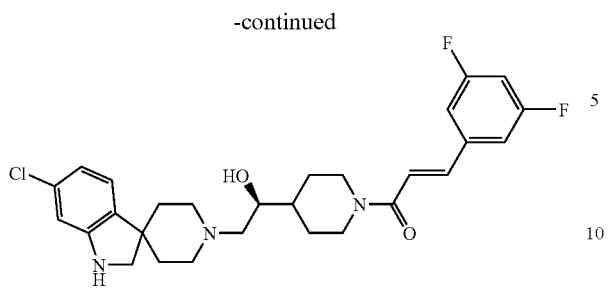

To a 2-L round bottomed flask was added (1S)-2-(6-chloro-1,2-dihydro-1'H-spiro[indole-3,4'-piperidin]-1'-yl)-1-(4-piperidinyl)ethanol (9.45 g, 27.1 mmol), (2E)-3-(3,5-difluorophenyl)-2-propenoic acid (5.23 g, 28.4 mmol) and HOBT (3.84 g, 28.4 mmol). DCE (450 mL) was added and the mixture was stirred. 1-Ethyl-3-(3'-dimethylaminopropyl)carbodiimide (EDCl, 5.45 g, 28.4 mmol) was added to the reaction mixture at room temperature and the reaction became cloudy with a thick precipitate. After 5 min, DMF (225 mL) was added and stirring was continued for 2.5 h whereupon saturated aqueous Na$_2$CO$_3$ (250 mL) and water (250 mL) were added to the reaction mixture. Stirring was continued for 30 min and the two layers were separated and the aqueous layer washed twice with DCM (500 mL). The combined organic washes were dried over Na$_2$SO$_4$, filtered, and concentrated to give a dark yellow oil. The crude oil was purified by Biotage SP4 reverse phase 65i C18 column using ACN: Water 0.1% TFA. The fractions containing product were combined in a separatory funnel along with DCM and aqueous NaHCO$_3$. The aqueous layer was washed three times with DCM and the combined DCM extracts were dried over Na$_2$SO$_4$, and then concentrated to afford the product (12.64 g, 91% yield) as an off-white solid. Product from the above reaction was checked on a Chiralpac IB column with a 40/60 ethanol/hexane mobile phase (1.3 mL/min) and when compared to a racemic mixture the sample was found to be >99% ee. MS (ES) m/e 516 [M+H]$^+$. $^1$H NMR (DMSO-d$_6$) δ 7.56 (m, 2H), 7.43 (s, 2H), 7.24 (m, 1H), 6.96 (d, J=7.8 Hz, 1H), 6.50 (m, 1H), 6.44 (d, J=2.0 Hz, 1H), 5.82 (v br s, 1H), 4.52 (br s, 1H), 4.35 (t, J=5.0 Hz, 1H), 4.28 (s, 1H), 3.45 (m, 1H), 3.03 (m, 1H), 2.81 (m, 2H), 2.62 (m, 2H), 2.32 (m, 2H), 2.08 (m, 2H), 1.75 (m, 3H), 1.57 (m, 4H), 1.25 (m, 2H).

Intermediate 12: Phenylmethyl 1,2-dihydro-1'H-spiro[indole-3,4'-piperidine]-1'-carboxylate

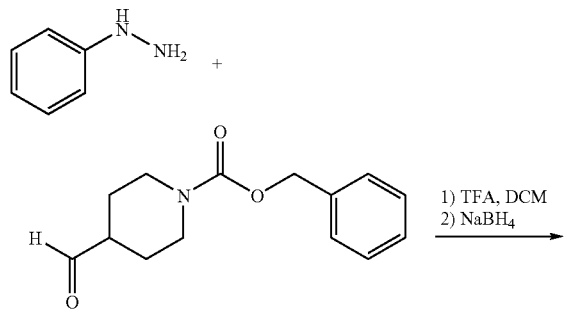

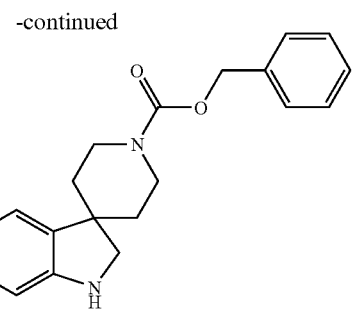

To a solution of phenylmethyl 4-formyl-1-piperidinecarboxylate (81 mmol) in 200 mL of DCM cooled in an ice bath was added phenylhydrazine (81 mmol). After stirring for approximately 15 min, TFA (202.5 mmol) was added over a period of 5 min. The mixture was allowed to slowly warm to room temperature and stir overnight. The mixture was then cooled in and ice bath and NaBH$_4$ (121.5 mmol) was added in small portions over 15 min. The resulting solution was allowed to warm to room temperature and stir for one hour, whereupon a 10% solution of NH$_4$OH (~100 mL) was added. After stirring for 30 min, the mixture was separated, and the aqueous layer extracted with DCM. The combine organic solutions were dried over Na$_2$SO$_4$ and concentrated. The residue was purified by column chromatography eluting with 0-10% MeOH in DCM. 12.72 g (39.4 mmol, 49% yield) of the desired product phenylmethyl 1,2-dihydro-1'H-spiro[indole-3,4'-piperidine]-1'-carboxylate was obtained. MS (ES) m/e 323 [M+H]$^+$.

Intermediate 13: 1,2-Dihydrospiro[indole-3,4'-piperidine]

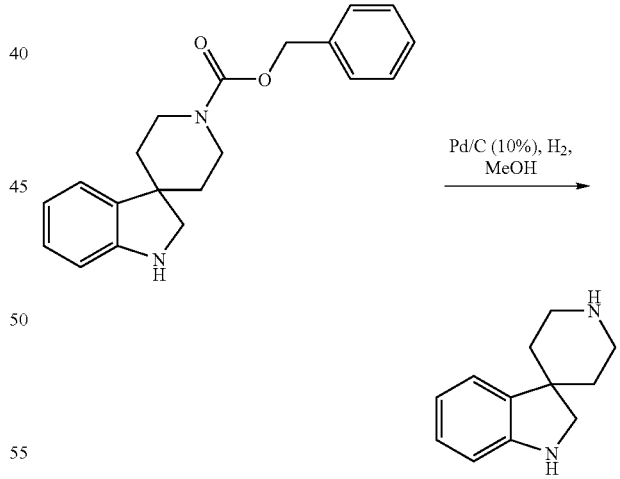

A solution of phenylmethyl 1,2-dihydro-1'H-spiro[indole-3,4'-piperidine]-1'-carboxylate (12.72 g, 39.4 mmol) in 200 mL of MeOH in a 500-mL flask was purged with N$_2$ for 15 min, after which time 10% Pd/C (5 g, approx 50% water) was added. The reaction flask was then purged with H$_2$ and fitted with a balloon charged with H$_2$. The reaction was allowed to stir at room temperature overnight. The mixture was then filtered through celite and the filtrate was concentrated. The celite/Pd/C mixture was stirred in 500 mL of MeOH for 30 min to extract remaining product that may have precipitated out of the reaction. The mixture was filtered through additional celite and the filtrate combined with the previous filtrate and concentrated. 5.05 g (26.7 mmol, 68% yield) of the desired product 1,2-dihydrospiro[indole-3,4'-piperidine] was obtained. MS (ES) m/e 189 [M+H]+.

Intermediate 14: 1-[(2E)-3-(3,5-Difluorophenyl)-2-propenoyl]-4-(2S-oxiranyl)piperidine (S,S)-Co-salen catalyst (206 mg) ((S,S)-(+)-N,N'-Bis(3,5-di-tert-butylsalicylidene)-1,2-cyclohexanediamino cobalt (II)) was dissolved in toluene (2 mL) in an open air flask. Glacial acetic acid (39 uL) was added and the reaction stirred at room temperature for 1 h. The reaction was then concentrated to a brown solid, which was placed under high vacuum overnight. 1-[(2E)-3-(3,5-difluorophenyl)-2-propenoyl]-4-(2-oxiranyl)piperidine (2 g) was dissolved in THF (2 mL). The catalyst was dissolved in THF (0.5 mL) and added to the solution of epoxide in an open air flask. The mixture was cooled to 0° C. and H$_2$O (69 uL) was added dropwise over 5 min. The reaction was warmed to room temperature and allowed to stir for 16 h. The reaction was then concentrated and purified by flash chromatography on a 120 g silica gel column (0 to 70% EtOAc/hexanes over 60 min.) to yield a yellow oil (805 mg, 40% yield). MS (ES) m/e 294 [M+H]+ $^1$H NMR (400 MHz, DMSO-d$_6$) d ppm 7.55 (d, J=16 Hz, 1H), 7.03 (m, 2H), 6.91 (m, 1H), 6.81 (m, 1H), 4.74 (m, 1H), 4.13 (m, 1H), 3.15 (m, 1H), 2.79 (m, 4H), 1.90 (m, 1H), 1.47 (m, 4H). A sample of 1-[(2E)-3-(3,5-difluorophenyl)-2-propenoyl]-4-(2S-oxiranyl)piperidine from the above reaction was checked on a Chiralpac AD column with a 100% methanol mobile phase (0.9 mL/min) and found to have a retention time of 8.3 min, when compared to a racemic mixture (retention time 8.1 and 8.3 min) and found to be 99% ee.

Example 3

(1S)-1-{1-[(2E)-3-(3,5-Difluorophenyl)-2-propenoyl]-4-piperidinyl}-2-(1,2-dihydro-1'H-spiro[indole-3,4'-piperidin]-1'-yl)ethanol

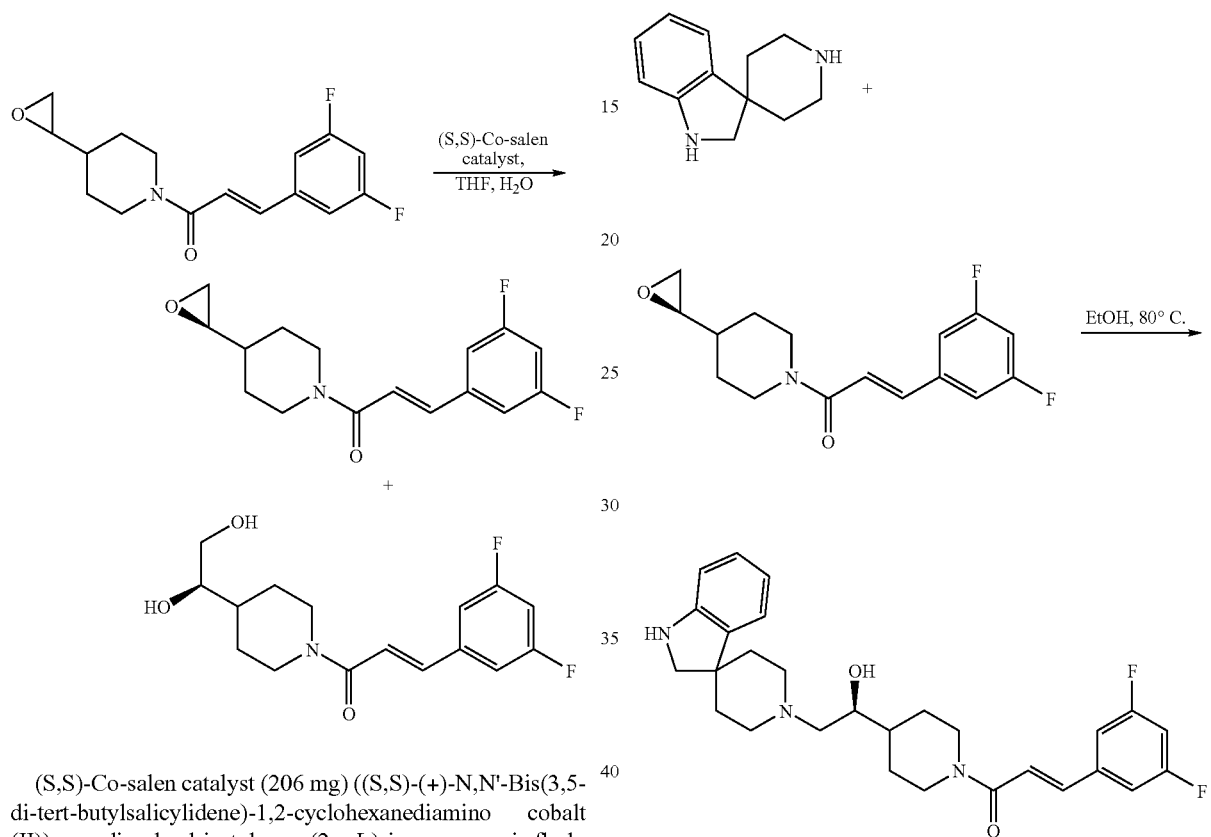

1,2-Dihydrospiro[indole-3,4'-piperidine] (6 mg) was added to a solution of 1-[(2E)-3-(3,5-difluorophenyl)-2-propenoyl]-4-(2S-oxiranyl)piperidine (10 mg) in EtOH (1 mL) and heated to 80° C. with stirring for 16 h, followed by concentration and purification by HPLC (Sunfire C-18 30×150 column; 10-50% CH$_3$CN, H$_2$O, 0.1% TFA over 17 min at 50 mL/min) to yield 10 mg (60% yield) of a white solid; MS (ES) m/e 482 [M+H]+; $^1$H NMR (400 MHz, DMSO-d$_6$) d ppm 7.26-7.52 (m, 8H), 6.99 (m ,1H), 4.71 (m, 1H), 4.37 (m, 1H), 3.75 (m, 2H), 3.33 (m, 6H), 3.20 (m, 2H), 2.75 (m, 1H), 2.33 (m, 2H), 2.06 (m, 3H), 1.78 (m, 2H), 1.45 (m, 2H). A sample of (1S)-1-{1-[(2E)-3-(3,5-difluorophenyl)-2-propenoyl]-4-piperidinyl}-2-(1,2-dihydro-1'H-spiro[indole-3,4'-piperidin]-1'-yl)ethanol from the above reaction was checked on a Chiralpac IB column with a 25/75% ethanol/hexane mobile phase (1.2 mL/min) and found to have a retention time of 7.7 min, when compared to a racemic mixture (retention time 7.7 and 8.5 min), the sample was found to be 99% ee.

Intermediate 15: 3'-Methyl-1'-(phenylmethyl)-1,2-dihydrospiro[indole-3,4'-piperidine]

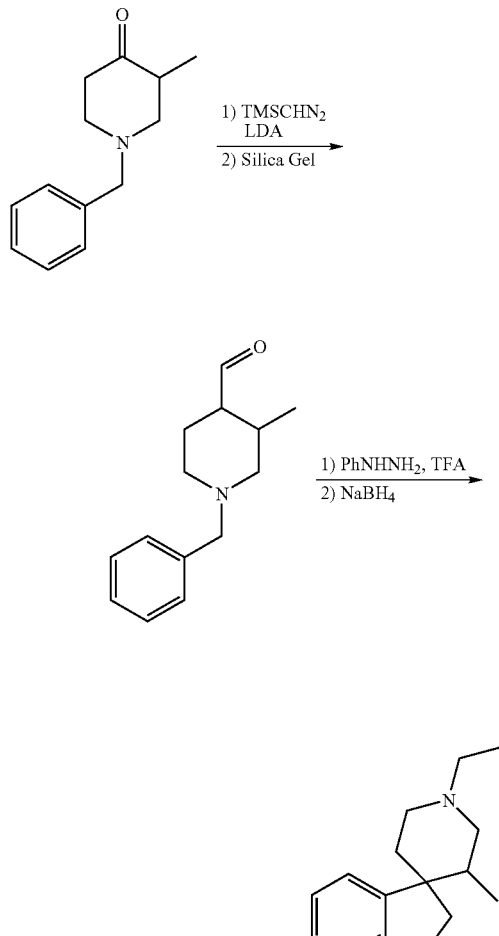

Diisopropylamine (246 mmol, 34.7 mL) was added to 50 mL THF and cooled to −78° C., whereupon n-butyllithium (29.5 mmol, 11. 8 mL, 2.5 M in hexanes) was added to form the lithium salt of diisopropylamine (LDA). The resulting solution was warmed to room temperature, and then cooled back to −78° C. (Trimethylsilyl)diazomethane (TMSCHN$_2$, 30 mmol, 15 mL, 2.0 M in hexanes) was added at −78° C., and stirring was continued for 30 min. 3-Methyl-1-(phenylmethyl)-4-piperidinone (24.6 mmol, 5 g) in 50 mL THF was then added dropwise at −78° C. Stirring was continued for 1 h at −78° C., then 3 h at reflux. After quenching the reaction with cold water, the mixture was extracted with diethyl ether (3×200 mL). The organic extracts were then dried over Na$_2$SO$_4$, filtered and concentrated under vacuum. To the residue was added EtOAc (500 mL), then silica gel (100 g). Stirring was continued for 18 h, then solvents removed and the resulting product on silica was removed by passing MeOH DCM (0 to 1:9) over a small column. After removal of solvents, the resulting residue (3.9 g) was taken directly to the next step.

To toluene (55 mL) was added with stirring phenylhydrazine (19.8 mmol, 2.13 g) and TFA (59.3 mmol, 6.8 g). The solution was warmed to 35° C., and the residue from above (3.9 g) was added in toluene (10 mL) over 2 h. The reaction was stirred overnight at 35° C., then raised to 70° C. for an additional 24 h, then cooled to 0° C. Methanol (4.5 mL) was added, followed by NaBH$_4$ (27 mmol, 1.02 g). After warming to room temperature, the solution was washed with 6% NH$_4$OH and the organics were concentrated in vacuo. The residue was purified by reverse phase chromatography, 10-50% acetonitrile/water (0.1% TFA) over 14 min to give 3'-methyl-1'-(phenylmethyl)-1,2-dihydrospiro[indole-3,4'-piperidine] (2.9 g). MS (ES) m/e 293 [M+H]$^+$. $^1$H NMR (400 MHz, DMSO-d$_6$) δ ppm 0.61 (d, J=6.78 Hz, 3 H) 1.88 (d, J=14.31 Hz, 1 H) 2.07 (td, J=13.99, 3.89 Hz, 1 H) 2.23 (ddd, J=12.30, 6.90, 3.89 Hz, 1 H) 2.84-2.98 (m, 1 H) 3.06 (br. s., 1 H) 3.35 (d, J=10.54 Hz, 2 H) 3.19-3.43 (m, 1 H) 3.57 (d, J=10.54 Hz, 1 H) 4.24-4.47 (m, 2 H) 6.69 (d, J=7.78 Hz, 1 H) 6.77 (t, J=7.40 Hz, 1 H) 6.95 (d, J=7.28 Hz, 1 H) 7.07 (t, J=7.53 Hz, 1 H) 7.36-7.61 (m, 6 H) 10.01 (d, J=2.01 Hz, 1 H).

Intermediate 16: 3'-Methyl-1,2-dihydrospiro[indole-3,4'-piperidine]

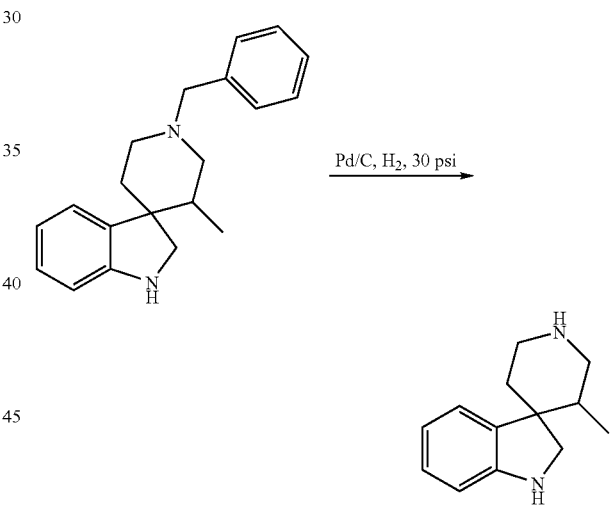

3'-Methyl-1'-(phenylmethyl)-1,2-dihydrospiro[indole-3,4'-piperidine] (10 mmol, 2.9 g), acetic acid (30 mL) and Pd/C (5%, 600 mg) were added to a Parr bottle. The mixture was subjected to hydrogen gas at 30 psi for 20 h, after which time the solution was filtered over celite, concentrated and purified by reverse phase chromatography, 10-50% acetonitrile/water (0.1% TFA) over 14 min to give 3'-methyl-1,2-dihydrospiro[indole-3,4'-piperidine] (750 mg) as the TFA salt as an off white solid. MS (ES) m/e 203 [M+H]$^+$ $^1$H NMR (400 MHz, DMSO-d$_6$) δ ppm 0.62 (d, J=7.03 Hz, 3 H) 1.83 (d, J=14.31 Hz, 1 H) 2.00 (td, J=13.87, 4.14 Hz, 1 H) 2.13 (dd, J=7.15, 4.39 Hz, 1 H) 2.77 (d, J=11.80 Hz, 1 H) 2.94 (d, J=11.54 Hz, 1 H) 3.17 (d, J=1.51 Hz, 1 H) 3.31 (d, J=13.30 Hz, 1 H) 3.40 (d, J=10.79 Hz, 1 H) 3.61 (d, J=11.04 Hz, 1 H) 6.79 (d, J=7.78 Hz, 1 H) 6.88 (t, J=7.28 Hz, 1 H) 7.03 (d, J=7.28 Hz, 1 H) 7.12 (t, J=7.15 Hz, 1H) 8.74 (br. s., 1 H) 8.87 (br. s., 1H).

Example 4

1-{1-[(2E)-3-(3,5-Difluorophenyl)-2-propenoyl]-4-piperidinyl}-2-(3'-methyl-1,2-dihydro-1'H-spiro[indole-3,4'-piperidin]-1'-yl)ethanol

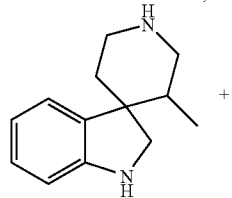

+

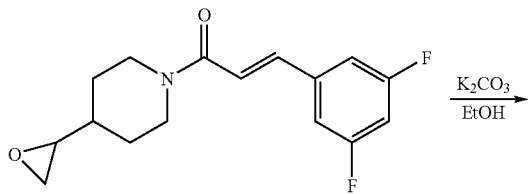

$\xrightarrow{\text{K}_2\text{CO}_3}{\text{EtOH}}$

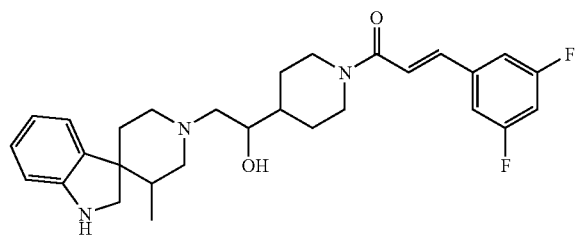

To 3'-methyl-1,2-dihydrospiro[indole-3,4'-piperidine] (0.3 mmol) in ethanol (4 mL) was added K₂CO₃ (1.3 mmol), and 1-[(2E)-3-(3,5-difluorophenyl)-2-propenoyl]-4-(2-oxiranyl)piperidine (0.3 mmol). The mixture was microwaved at 160° C. for 10 min. The crude mixture was concentrated, filtered, and purified by reverse phase chromatography, 10-50% acetonitrile/water (0.1% TFA) over 14 min to give 1-{1-[(2E)-3-(3,5-difluorophenyl)-2-propenoyl]-4-piperidinyl}-2-(3'-methyl-1,2-dihydro-1'H-spiro[indole-3,4'-piperidin]-1'-yl)ethanol as an off white solid. MS (ES) m/e 496 [M+H]⁺ ¹H NMR (400 MHz, DMSO-d₆) δ ppm 0.62 (t, J=7.40 Hz, 3 H) 1.24 (br. s., 4 H) 1.64 (br. s., 2 H) 1.84 (br. s., 2 H) 2.27 (br. s., 1 H) 2.34 (br. s., 1 H) 2.67 (d, J=2.01 Hz, 1 H) 2.92 (br. s., 1 H) 3.06 (br. s., 2 H) 3.17 (br. s., 2 H) 3.32 (t, J=9.91 Hz, 2 H) 3.53 (d, J=8.53 Hz, 1 H) 3.79 (br. s., 1 H) 4.42 (br. s., 1 H) 4.55 (br. s., 1 H) 6.64 (br. s., 1 H) 6.70-6.81 (m, 1 H) 6.95 (d, J=7.28 Hz, 1 H) 7.05 (t, J=7.53 Hz, 1 H) 7.26 (tt, J=9.25, 2.29 Hz, 1 H) 7.45 (s, 2 H) 7.57 (d, J=6.78 Hz, 2 H) 9.28 (br. s., 1 H).

Intermediate 17: 1,1-Dimethylethyl 5-fluoro-1'-[2-hydroxy-2-(1-{[(phenylmethyl)oxy]carbonyl}-4-piperidinyl)ethyl]spiro[indole-3,4'-piperidine]-1(2H)-carboxylate

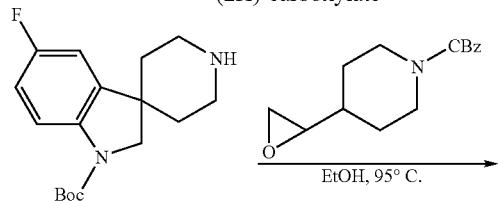

$\xrightarrow{\text{EtOH, 95° C.}}$

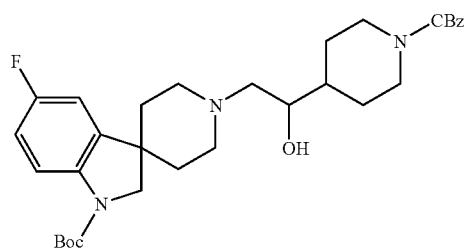

Phenylmethyl 4-(2-oxiranyl)-1-piperidinecarboxylate (990 mg) was added to a solution of 1,1-dimethylethyl 5-fluorospiro[indole-3,4'-piperidine]-1(2H)-carboxylate (1.16 g) in EtOH (20 mL). The reaction was heated to 95° C. for 7 h and then stirred at room temperature overnight. The solvent was removed and the title compound was obtained as crude oil. MS (ES) m/e 568 [M+H]⁺.

Intermediate 18: Phenylmethyl 4-[2-(5-fluoro-1,2-dihydro-1'H-spiro[indole-3,4'-piperidin]-1'-yl)-1-hydroxyethyl]-1-piperidinecarboxylate

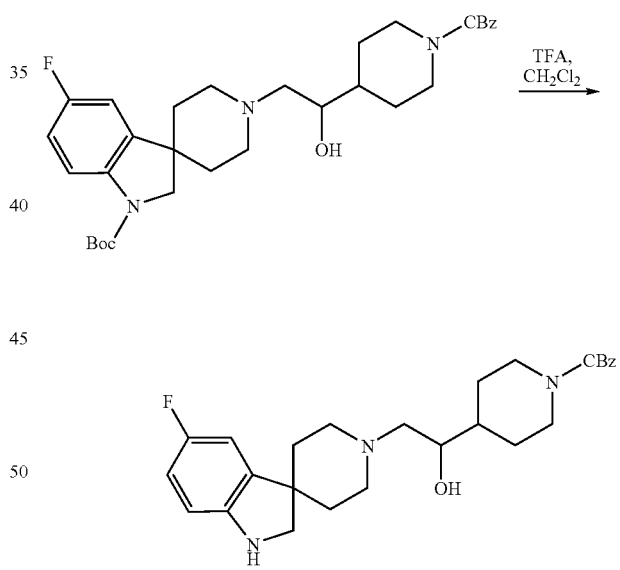

1,1-Dimethylethyl 5-fluoro-1'-[2-hydroxy-2-(1-{[(phenylmethyl)oxy]carbonyl}-4-piperidinyl)ethyl]spiro[indole-3,4'-piperidine]-1(2H)-carboxylate (2.15 g) was dissolved in CH₂Cl₂ (13 mL) and cooled to 0° C. TFA (6 mL) was added, and the reaction was warmed to room temperature and stirred for 1 h. The solution was adjusted to a pH 10 using 2N NaOH. The layers were separated and the aqueous layer was extracted with CH₂Cl₂; the combined extracts were washed with brine, dried over Na₂SO₄, filtered, and concentrated to give the title compound. The crude oil (1.72 g) was used without further purification. MS (ES) m/e 468 [M+H]⁺.

Intermediate 19; 2-(5-Fluoro-1,2-dihydro-1'H-spiro[indole-3,4'-piperidin]-1'-yl)-1-(4-piperidinyl)ethanol

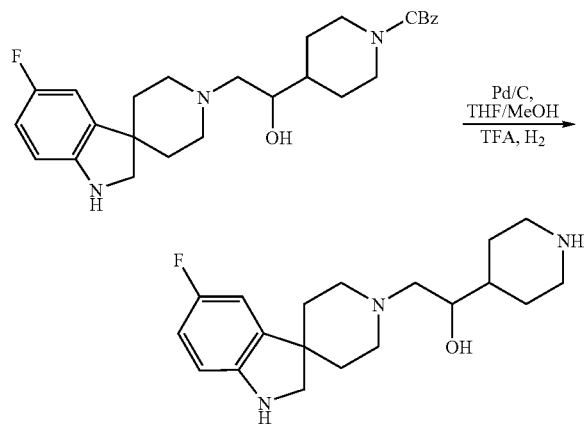

Phenylmethyl 4-[2-(5-fluoro-1,2-dihydro-1'H-spiro[indole-3,4'-piperidin]-1'-yl)-1-hydroxyethyl]-1-piperidinecarboxylate (1.7 g) was suspended in a solution of 1:1 THF/MeOH (18 mL). TFA was added until the solid was completely dissolved and then 10% Pd/C (780 mg) was added. The reaction head space was purged with $H_2$ while the reaction was vigorously stirred for several minutes, then the reaction was stirred under an $H_2$ atmosphere for 30 min. The acid was quenched with saturated aqueous $Na_2CO_3$ and the solvent was removed. The resulting solid was extracted with $CH_2Cl_2$ and the filtrate concentrated to give the title compound (1.0 g).

Example 5

2-(5-Fluoro-1,2-dihydro-1'H-spiro[indole-3,4'-piperidin]-1'-yl)-1-(1-{(2E)-3-[4-(trifluoromethyl)phenyl]-2-propenoyl}-4-piperidinyl)ethanol

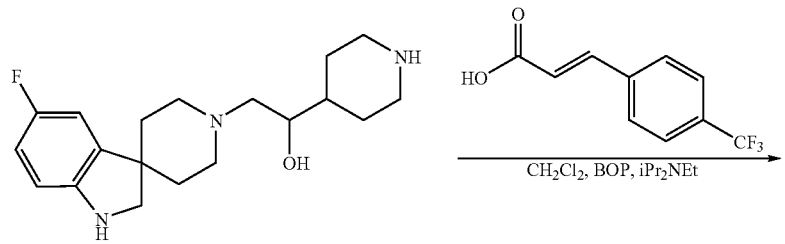

To a solution of 2-(5-fluoro-1,2-dihydro-1'H-spiro[indole-3,4'-piperidin]-1'-yl)-1-(4-piperidinyl)ethanol (50 mg) in 0.5 mL $CH_2Cl_2$ was added 4-trifluoromethylcinnamic acid (27 mg) followed by diisopropylethylamine (iPr$_2$NEt, 38 μL) and BOP (86 mg). The reaction was stirred for 1 h, then diluted with MeOH and filtered. The title compound was isolated via preparative HPLC as the corresponding TFA salt. HPLC Rt=1.5 min; MS (ES), m/e 532 [M+H]$^+$; 1H NMR (400 MHz, DMSO-d6) δ ppm 1.10-1.36 (m, 2 H) 1.57-1.74 (m, 2 H) 1.76-1.93 (m, 3 H) 1.97-2.12 (m, 1 H) 2.14-2.28 (m, 1 H) 2.58-2.71 (m, 1 H) 2.93-3.24 (m, 4 H) 3.24-3.65 (m, 4 H) 3.71-3.84 (m, 1 H) 4.33-4.47 (m, 1 H) 4.50-4.64 (m, 1 H) 6.61-6.72 (m, 1 H) 6.76-6.84 (m, 1 H) 6.84-6.94 (m, 1 H) 7.53 (s, 2 H) 7.77 (d, J=8.28 Hz, 2 H) 7.97 (d, J=8.03 Hz, 2 H).

Example 6

N-(3,4-Dichlorophenyl)-4-[2-(5-fluoro-1,2-dihydro-1'H-spiro[indole-3,4'-piperidin]-1'-yl)-1-hydroxyethyl]-1-piperidinecarboxamide

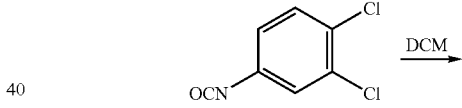

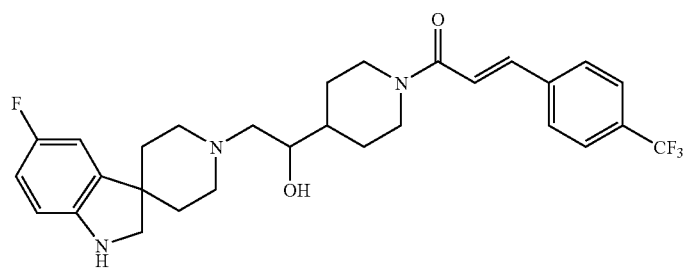

-continued

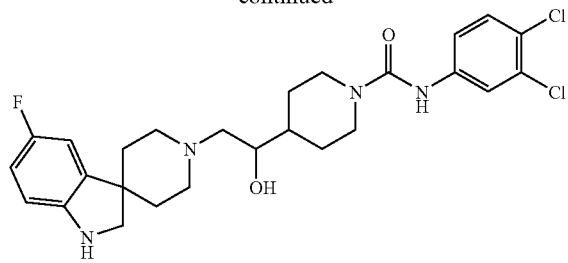

A solution of 2-(5-fluoro-1,2-dihydro-1'H-spiro[indole-3,4'-piperidin]-1'-yl)-1-(4-piperidinyl)ethanol (0.12 mmol) and (3,4-dichlorophenyl)isocyanate (0.12 mmol) in 1 mL of DCM was allowed to stir at room temperature overnight. The mixture was then washed with NaHCO₃. The organic layer was concentrated and purified by HPLC to obtain 13.7 mg (0.022 mmol, 18% yield) of the desired product. MS (ES) m/e 521 (M+H)⁺. ¹H NMR (500 MHz, DMSO-d₆) δ ppm 1.13-1.31 (m, 2 H) 1.50-1.61 (m, 2 H) 1.71-1.91 (m, 2 H) 2.01 (t, 1 H) 2.18 (t, 1 H) 2.48 (s, 2 H) 2.75 (t, J=12.70 Hz, 2 H) 2.93-3.22 (m, 4 H) 3.35 (d, J=5.37 Hz, 1 H) 3.39-3.49 (m, 2 H) 3.51 (br. s., 1 H) 4.17 br. s., 2 H) 6.53-6.60 (m, 1 H) 6.74 (dd, J=8.55, 2.69 Hz, 1 H) 6.81 (t, J=9.03 Hz, 1 H) 7.45 (s, 2 H) 7.83 (s, 1 H) 8.72-8.81 (m, 2 H) 9.02-9.22 (m, 1 H).

Example 7

N-(4-Bromo-3-chlorophenyl)-4-[2-(5-fluoro-1,2-dihydro-1'H-spiro[indole-3,4'-piperidin]-1'-yl)-1-hydroxyethyl]-1-piperidinecarboxamide To a mixture of 4-bromo-3-chloroaniline (0.12 mmol) and N-methylmorpholine (NMM, 0.12 mmol) in 1 mL of DCM was added isopropenyl chloroformate (0.12 mmol). The mixture was allowed to stir overnight at room temperature. The mixture was then washed with NaHCO₃ and the organic layer was separated and concentrated to dryness. The residue was dissolved in DMF (1 mL) and 2-(5-fluoro-1,2-dihydro-1'H-spiro[indole-3,4'-piperidin]-1'-yl)-1-(4-piperidinyl)ethanol (0.11 mol) was added. The resulting solution was heated to 60° C. for 3 h. The solution was then cooled to room temperature and purified by HPLC to obtain 35 mg (47% yield) of the desired product. MS (ES) m/e 565, 567. ¹H NMR (500 MHz, DMSO-d₆) δ ppm 1.10-1.31 (m, 2 H) 1.49-1.60 (m, 2 H) 1.72-1.86 (m, 2 H) 2.01 (t, 1 H) 2.18 (t, 1 H) 2.48 (s, 2 H) 2.75 (t, J=12.70 Hz, 2 H) 2.94-3.22 (m, 4 H) 3.29-3.36 (m, 1 H) 3.40-3.48 (m, 2 H) 3.53 (d, 1 H) 4.15 (d, J=12.21 Hz, 2 H) 6.51-6.58 (m, 1 H) 6.74 (dd, J=8.55, 2.69 Hz, 1 H) 6.81 (t, 1 H) 7.38 (dd, J=8.79, 2.44 Hz, 1 H) 7.57 (d, J=8.79 Hz, 1 H) 7.84 (s, 1 H) 8.76 (s, 2 H) 9.00-9.27 (m, 2 H).

Intermediate 20: Bis(1,1-dimethylethyl) 2-oxo-1'H-spiro[indole-3,4'-piperidine]-1,1'(2H)-dicarboxylate

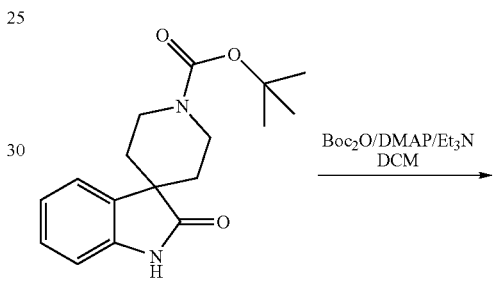

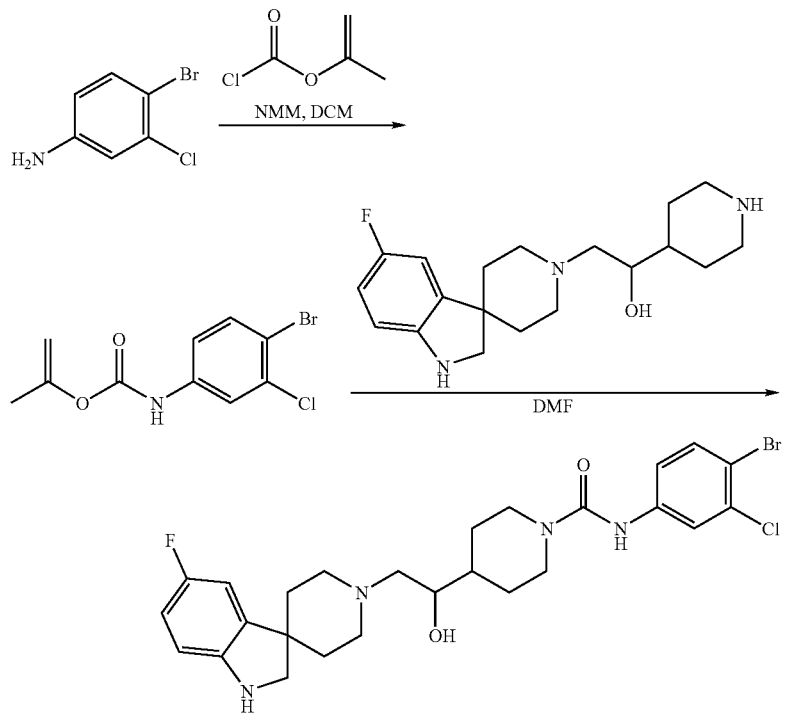

-continued

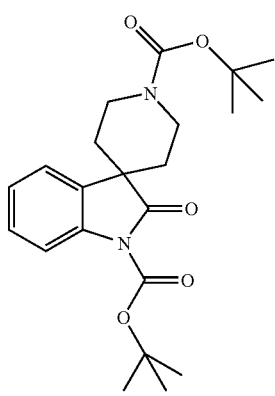

1,1-Dimethylethyl 2-oxo-1,2-dihydro-1'H-spiro[indole-3,4'-piperidine]-1'-carboxylate (500 mg, 1.7 mmol) was treated with a solution of di-t-butyldicarbonate (Boc$_2$O, 432 mg, 2.0 mmol) in DCM (10 mL). The resulting solution was treated with Et$_3$N (0.23 mL, 1.65 mol) and stirred at 25° C. for ~3 h. The reaction mixture was concentrated on SiO$_2$ (2 g) and purified via flash column chromatography (FCC) 0-15% EtOAc/Hexanes to afford the product (628 mg, 95%) as an oil.

Intermediate 21: Bis(1,1-dimethylethyl) 2-hydroxy-2-methyl-1'H-spiro[indole-3,4'-piperidine]-1,1'(2H)-dicarboxylate

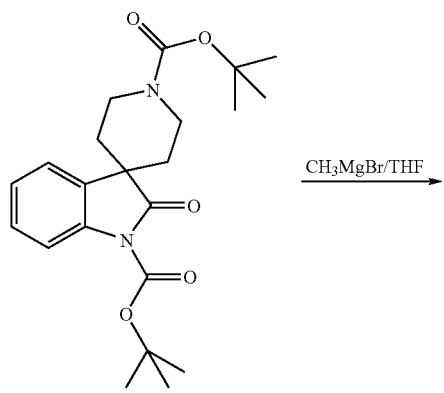

A 0° C. solution of bis(1,1-dimethylethyl) 2-oxo-1'H-spiro[indole-3,4'-piperidine]-1,1'(2H)-dicarboxylate (200 mg, 0.5 mmol) in THF (5 mL) was treated with CH$_3$MgBr (3M in THF, 0.17 mL, 0.5 mmol) and stirred at 0° C. for 1 h. The reaction was then quenched with H$_2$O (10 mL), extracted with EtOAc (3×10 mL), dried over Na$_2$SO$_4$, and concentrated. The residue was dissolved in hexanes and purified via flash column chromatography (FCC) (0-15% EtOAc/hexanes) to give the product (88 mg, 42%). MS (ES) m/e 441 [M+Na]$^+$ Intermediate 22: 2-Methyl-1,2-dihydrospiro[indole-3,4'-piperidine]

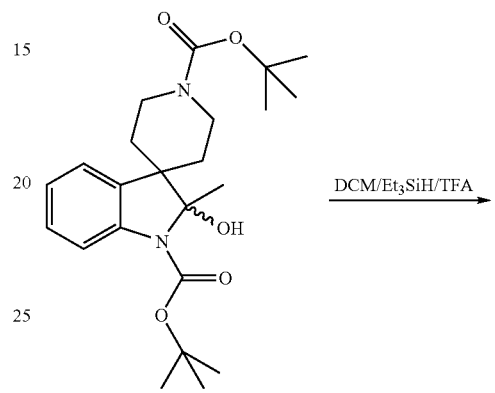

Bis(1,1-dimethylethyl)2-hydroxy-2-methyl-1'H-spiro[indole-3,4'-piperidine]-1,1'(2H)-dicarboxylate (80 mg, 0.19 mmol) in DCM (1.5 mL) was treated with TFA (0.5 mL) and stirred at room temperature for 3 h. The solvent was removed in vacuo, and the residue was dissolved in MeOH and purified via an SCX column (elution with 2M NH$_3$ in MeOH) to afford the product (43 mg, 100%). MS (ES) m/e 203 [M+H]$^+$.

Intermediate 23: Phenylmethyl 1-methyl-1,2-dihydro-1'H-spiro[indole-3,4'-piperidine]-1'-carboxylate

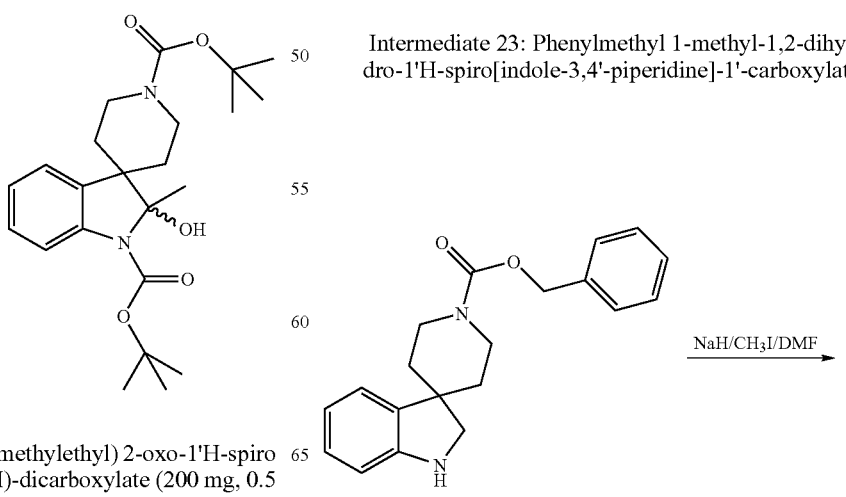

-continued

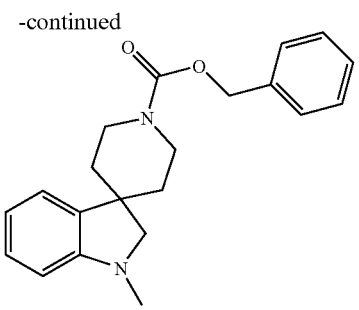

A 0° C. solution of phenylmethyl 1,2-dihydro-1'H-spiro[indole-3,4'-piperidine]-1'-carboxylate (100 mg, 0.3 mmol) in DMF (3 mL) was treated with NaH (95%, 10 mg, 0.4 mmol) and stirred at room temperature for 30 min. The solution was cooled to 0° C. and treated with $CH_3I$ (0.019 mL, 0.31 mmol) and stirred at room temperature overnight. The reaction was quenched with saturated aqueous $NH_4Cl$ and extracted with EtOAc. The organic layers were combined, concentrated and purified by FCC (0-25% EtOAc/hexanes) to afford the product (40 mg, 40%), MS (ES) m/e 337 [M+H]$^+$.

Example 8

1-{1-[(2E)-3-(3,5-Difluorophenyl)-2-propenoyl]-4-piperidinyl}-2-(1-methyl-1,2-dihydro-1'H-spiro[indole-3,4'-piperidin]-1'-yl)ethanol

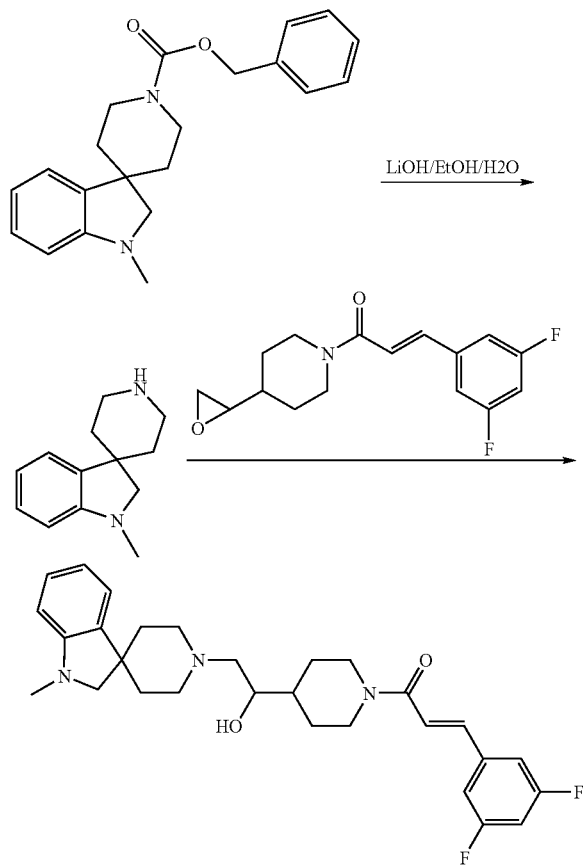

Phenylmethyl 1-methyl-1,2-dihydro-1'H-spiro[indole-3,4'-piperidine]-1'-carboxylate (40 mg, 0.12 mmol) was treated with LiOH hydrate (15 mg, 0.36 mmol), EtOH/$H_2O$(1:1, 0.5 mL) and THF (0.5 mL) and microwaved at 160° C. for 30 min. The reaction mixture was diluted with $H_2O$ and extracted with EtOAc. The combined organic layers were then concentrated. The residue was dissolved in EtOH (0.5 mL), treated with 1-[(2E)-3-(3,5-difluorophenyl)-2-propenoyl]-4-(2-oxiranyl)piperidine (35 mg, 0.12 mmol) and microwaved at 170° C. for 15 min. The reaction mixture was purified by reverse phase HPLC to afford the product (27 mg, 50%), MS (ES), m/e 496 [M+H]$^+$.

Intermediate 24: 1,1-Dimethylethyl 6-cyano-1,2-dihydro-1'H-spiro[indole-3,4'-piperidine]-1'-carboxylate

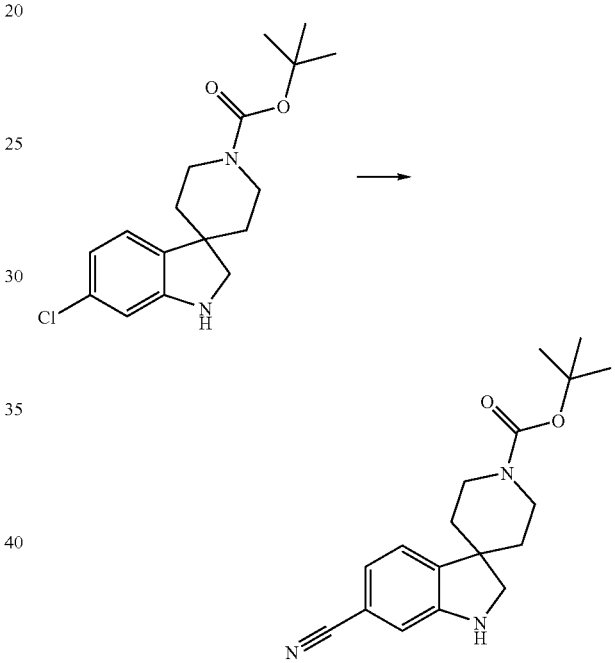

1,1-Dimethylethyl 6-chloro-1,2-dihydro-1'H-spiro[indole-3,4'-piperidine]-1'-carboxylate (1 g, 3.10 mmol), palladium triflate (44 mg, 0.133 mmol), zinc flake (38 mg, 0.589 mmol), zinc cyanide (0.204 g, 1.735 mmol) and 1,1'-binaphthalen-2-yl[bis(1,1-dimethylethyl)]phosphane (0.109 g, 0.273 mmol) were weighed into a vial and sealed. The vial was connected to vacuum and $N_2$ lines through needles and the system was evacuated under high vacuum for 2 mins, then backfilled with $N_2$. Then, 5 mL dry dimethylacetamide was added and the system was evacuated and refilled with $N_2$ three times, and the vial placed in a 95° C. oil bath overnight. The reaction mixture was cooled down and diluted with 15 mL water. The resulting mixture was extracted with ethyl acetate (3×25 mL). The combined organics were dried over $MgSO_4$ and concentrated. The residue was purified via ISCO silica gel chromatography eluting with 0-10% EtOAc in hexanes to give the final product as a white solid, 0.96 g, 99% yield, MS (ES) m/e 336 (M+Na)$^+$.

The following table illustrates compounds that were prepared in substantial accordance with the indicated Schemes.

| Ex # | Chemical Structure | Schm. | m/z | Name |
|---|---|---|---|---|
| 9 | 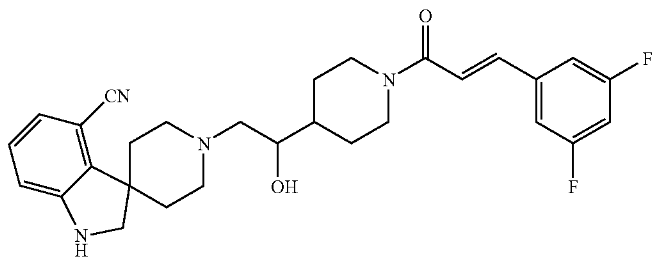 | 2 | 507 | 1'-(2-{1-[(2E)-3-(3,5-difluorophenyl)-2-propenoyl]-4-piperidinyl}-2-hydroxyethyl)-1,2-dihydrospiro[indole-3,4'-piperidine]-4-carbonitrile trifluoroacetate |
| 10 | 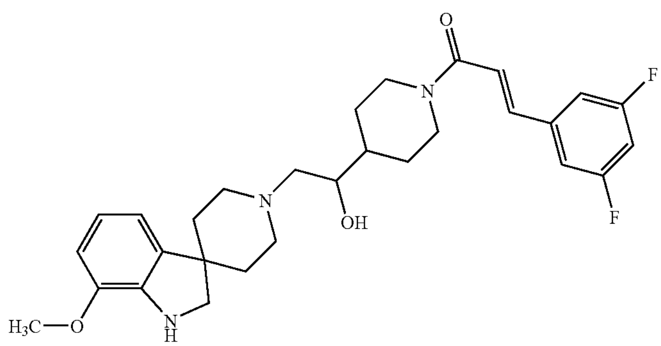 | 2 | 512 | 1-{1-[(2E)-3-(3,5-difluorophenyl)-2-propenoyl]-4-piperidinyl}-2-[7-(methyloxy)-1,2-dihydro-1'H-spiro[indole-3,4'-piperidin]-1'-yl]ethanol |
| 11 | 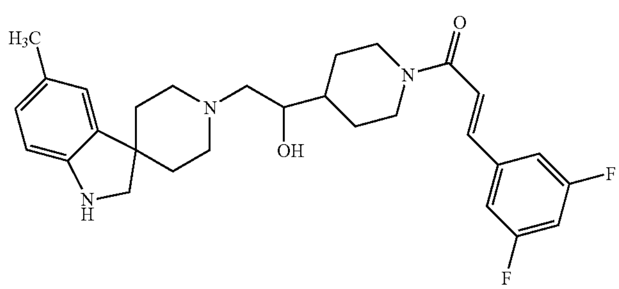 | 2 | 496 | 1-{1-[(2E)-3-(3,5-difluorophenyl)-2-propenoyl]-4-piperidinyl}-2-(5-methyl-1,2-dihydro-1'H-spiro[indole-3,4'-piperidin]-1'-yl)ethanol |
| 12 | 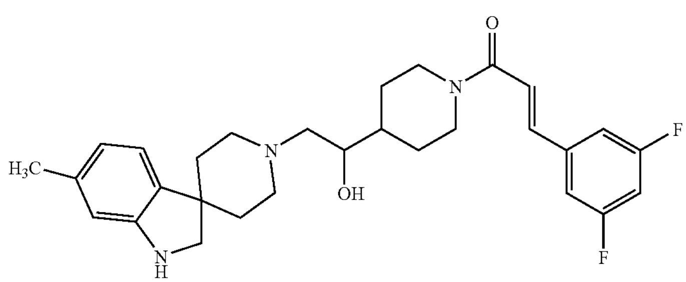 | 2 | 496 | 1-{1-[(2E)-3-(3,5-difluorophenyl)-2-propenoyl]-4-piperidinyl}-2-(6-methyl-1,2-dihydro-1'H-spiro[indole-3,4'-piperidin]-1'-yl)ethanol |
| 13 | 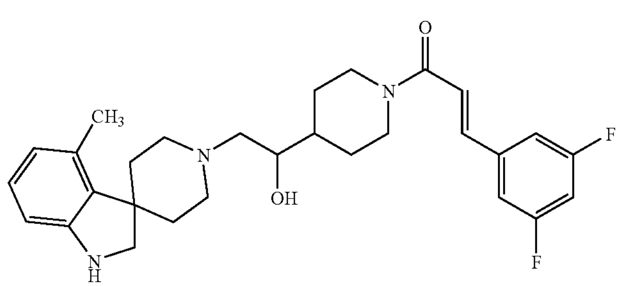 | 2 | 496 | 1-{1-[(2E)-3-(3,5-difluorophenyl)-2-propenoyl]-4-piperidinyl}-2-(4-methyl-1,2-dihydro-1'H-spiro[indole-3,4'-piperidin]-1'-yl)ethanol |

-continued

| Ex # | Chemical Structure | Schm. | m/z | Name |
|---|---|---|---|---|
| 14 | 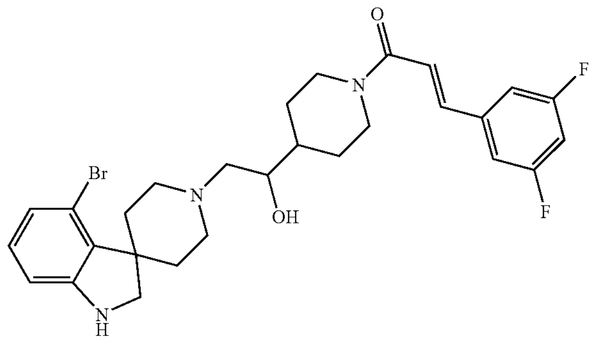 | 2 | 559, 561 | 2-(4-bromo-1,2-dihydro-1'H-spiro[indole-3,4'-piperidin]-1'-yl)-1-{1-[(2E)-3-(3,5-difluorophenyl)-2-propenoyl]-4-piperidinyl}ethanol |
| 15 | 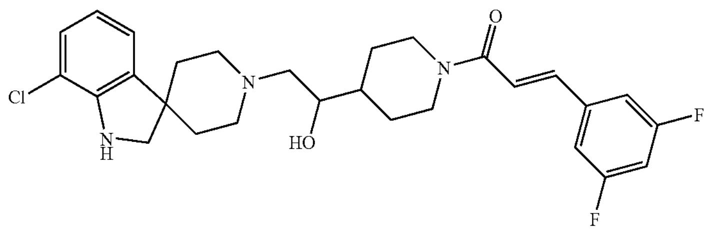 | 2 | 516 | 2-(7-chloro-1,2-dihydro-1'H-spiro[indole-3,4'-piperidin]-1'-yl)-1-{1-[(2E)-3-(3,5-difluorophenyl)-2-propenoyl]-4-piperidinyl}ethanol |
| 16 | 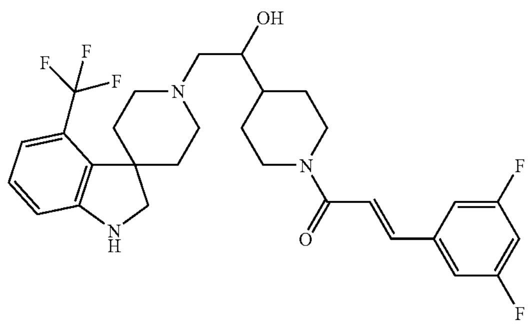 | 2 | 550 | 1-{1-[(2E)-3-(3,5-difluorophenyl)-2-propenoyl]-4-piperidinyl}-2-[4-(trifluoromethyl)-1,2-dihydro-1'H-spiro[indole-3,4'-piperidin]-1'-yl]ethanol |
| 17 | 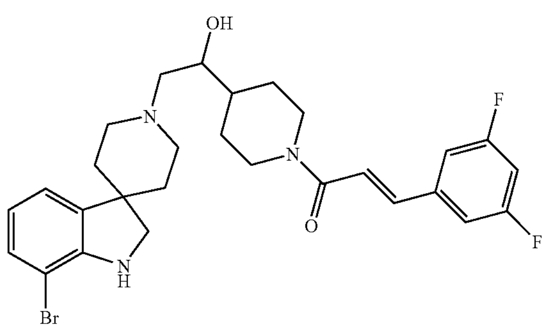 | 2 | 559, 561 | 2-(7-bromo-1,2-dihydro-1'H-spiro[indole-3,4'-piperidin]-1'-yl)-1-{1-[(2E)-3-(3,5-difluorophenyl)-2-propenoyl]-4-piperidinyl}ethanol |
| 18 | 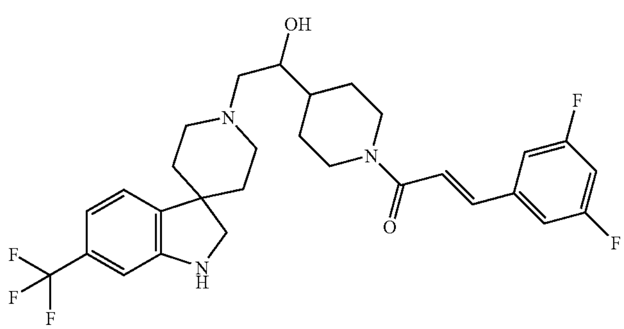 | 2 | 550 | 1-{1-[(2E)-3-(3,5-difluorophenyl)-2-propenoyl]-4-piperidinyl}-2-[6-(trifluoromethyl)-1,2-dihydro-1'H-spiro[indole-3,4'-piperidin]-1'-yl]ethanol |

-continued

| Ex # | Chemical Structure | Schm. | m/z | Name |
|---|---|---|---|---|
| 19 | 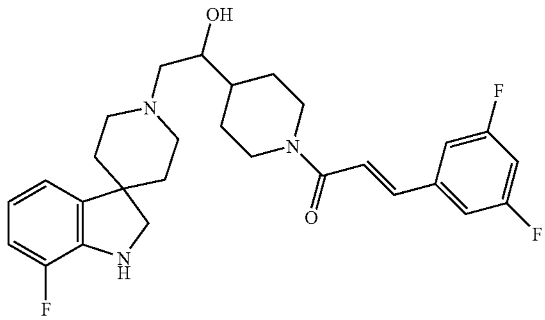 | 2 | 500 | 1-{1-[(2E)-3-(3,5-difluorophenyl)-2-propenoyl]-4-piperidinyl}-2-(7-fluoro-1,2-dihydro-1'H-spiro[indole-3,4'-piperidin]-1'-yl)ethanol |
| 20 | 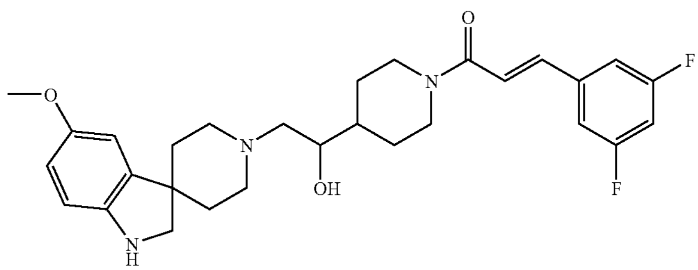 | 2 | 512 | 1-{1-[(2E)-3-(3,5-difluorophenyl)-2-propenoyl]-4-piperidinyl}-2-[5-(methyloxy)-1,2-dihydro-1'H-spiro[indole-3,4'-piperidin]-1'-yl]ethanol |
| 21 | 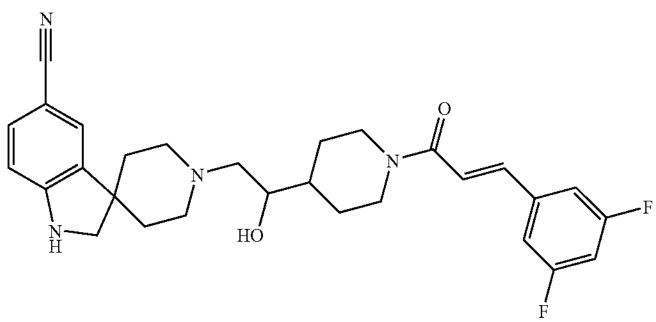 | 2 | 507 | 1'-(2-{1-[(2E)-3-(3,5-difluorophenyl)-2-propenoyl]-4-piperidinyl}-2-hydroxyethyl)-1,2-dihydrospiro[indole-3,4'-piperidine]-5-carbonitrile |
| 22 | 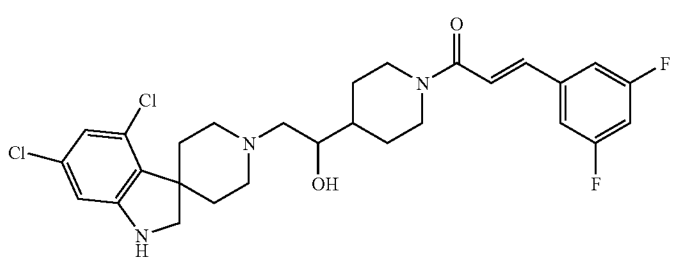 | 2 | 550 | 2-(4,6-dichloro-1,2-dihydro-1'H-spiro[indole-3,4'-piperidin]-1'-yl)-1-{1-[(2E)-3-(3,5-difluorophenyl)-2-propenoyl]-4-piperidinyl}ethanol trifluoroacetate |
| 23 | 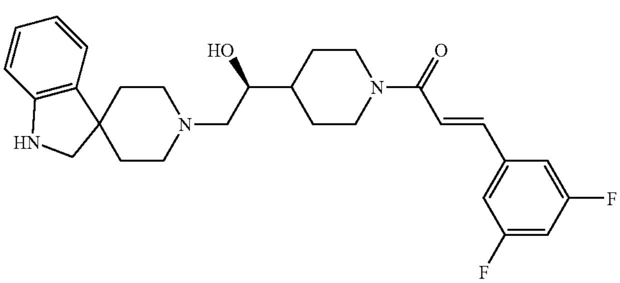 | 10 | 482 | (1S)-1-{1-[(2E)-3-(3,5-difluorophenyl)-2-propenoyl]-4-piperidinyl}-2-(1,2-dihydro-1'H-spiro[indole-3,4'-piperidin]-1'-yl)ethanol |

| Ex # | Schm. | m/z | Name |
|---|---|---|---|
| 24 | 2 | 516 | 2-(4-chloro-1,2-dihydro-1'H-spiro[indole-3,4'-piperidin]-1'-yl)-1-{1-[(2E)-3-(3,5-difluorophenyl)-2-propenoyl]-4-piperidinyl}ethanol |
| 25 | 5 | 460 | 2-(1,2-dihydro-1'H-spiro[indole-3,4'-piperidin]-1'-yl)-1-{1-[(2E)-3-(4-methylphenyl)-2-propenoyl]-4-piperidinyl}ethanol |
| 26 | 5 | 542 | 1-{1-[(2E)-3-(3-bromo-4-fluorophenyl)-2-propenoyl]-4-piperidinyl}-2-(1,2-dihydro-1'H-spiro[indole-3,4'-piperidin]-1'-yl)ethanol |
| 27 | 5 | 530 | 2-(1,2-dihydro-1'H-spiro[indole-3,4'-piperidin]-1'-yl)-1-[1-((2E)-3-{4-[(trifluoromethyl)oxy]phenyl}-2-propenoyl)-4-piperidinyl]ethanol |
| 28 | 5 | 482 | 1-{1-[(2E)-3-(3,4-difluorophenyl)-2-propenoyl]-4-piperidinyl}-2-(1,2-dihydro-1'H-spiro[indole-3,4'-piperidin]- 1'-yl)ethanol |
| 29 | 5 | 480 | 1-{1-[(2E)-3-(3-chlorophenyl)-2-propenoyl]-4-piperidinyl}-2-(1,2-dihydro-1'H-spiro[indole-3,4'-piperidin]-1'-yl)ethanol |

| Ex # | Chemical Structure | Schm. | m/z | Name |
|---|---|---|---|---|
| 30 | 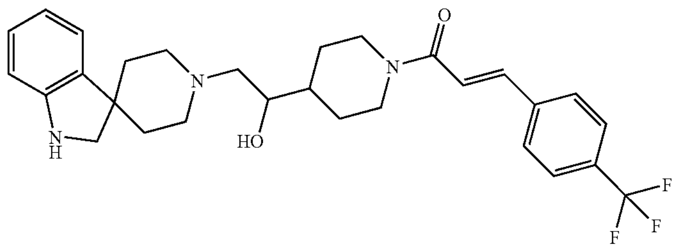 | 5 | 514 | 2-(1,2-dihydro-1'H-spiro[indole-3,4'-piperidin]-1'-yl)-1-(1-{(2E)-3-[4-(trifluoromethyl)phenyl]-2-propenoyl}-4-piperidinyl)ethanol |
| 31 | 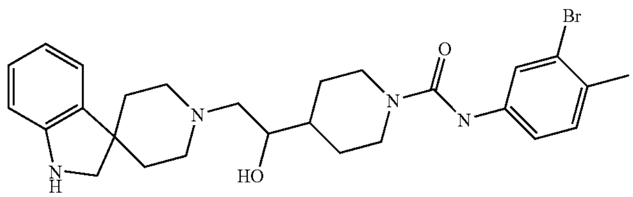 | 7 | 529 | N-(3-bromo-4-methylphenyl)-4-[2-(1,2-dihydro-1'H-spiro[indole-3,4'-piperidin]-1'-yl)-1-hydroxyethyl]-1-piperidinecarboxamide |
| 32 | 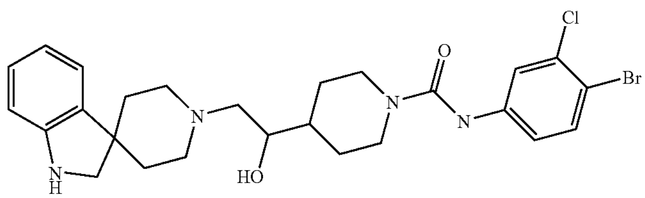 | 7 | 549 | N-(4-bromo-3-chlorophenyl)-4-[2-(1,2-dihydro-1'H-spiro[indole-3,4'-piperidin]-1'-yl)-1-hydroxyethyl]-1-piperidinecarboxamide |
| 33 | 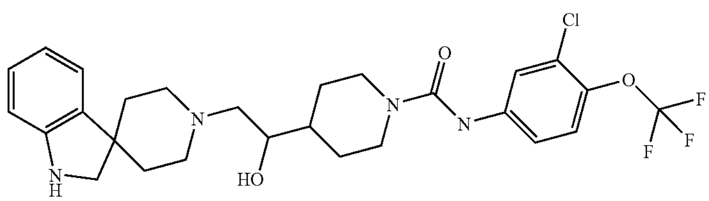 | 7 | 553 | N-{3-chloro-4-[(trifluoromethyl)oxy]phenyl}-4-[2-(1,2-dihydro-1'H-spiro[indole-3,4'-piperidin]-1'-yl)-1-hydroxyethyl]-1-piperidinecarboxamide |
| 34 | 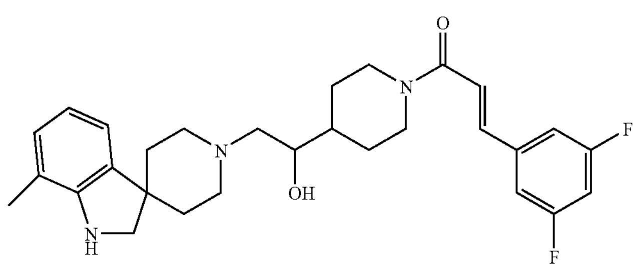 | 2 | 496 | 1-{1-[(2E)-3-(3,5-difluorophenyl)-2-propenoyl]-4-piperidinyl}-2-(7-methyl-1,2-dihydro-1'H-spiro[indole-3,4'-piperidin]-1'-yl)ethanol |
| 35 | 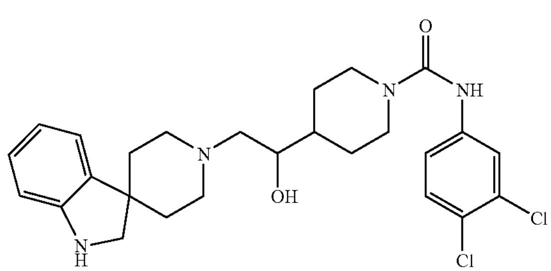 | 6 | 503 | N-(3,4-dichlorophenyl)-4-[2-(1,2-dihydro-1'H-spiro[indole-3,4'-piperidin]-1'-yl)-1-hydroxyethyl]-1-piperidinecarboxamide |

-continued

| Ex # | Chemical Structure | Schm. | m/z | Name |
|---|---|---|---|---|
| 36 | 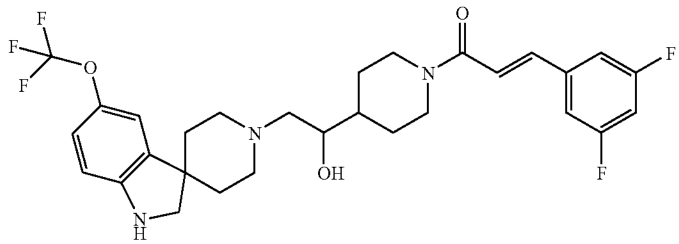 | 2 | 566 | 1-{1-[(2E)-3-(3,5-difluorophenyl)-2-propenoyl]-4-piperidinyl}-2-{5-[(trifluoromethyl)oxy]-1,2-dihydro-1'H-spiro[indole-3,4'-piperidin]-1'-yl}ethanol |
| 37 | 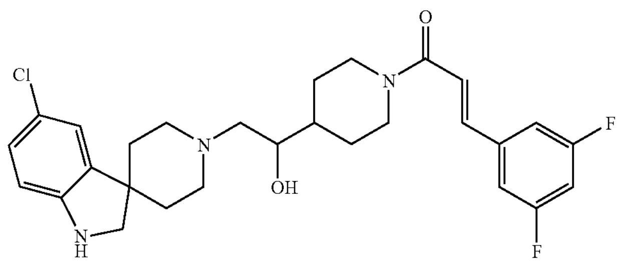 | 2 | 516 | 2-(5-chloro-1,2-dihydro-1'H-spiro[indole-3,4'-piperidin]-1'-yl)-1-{1-[(2E)-3-(3,5-difluorophenyl)-2-propenoyl]-4-piperidinyl}ethanol |
| 38 | 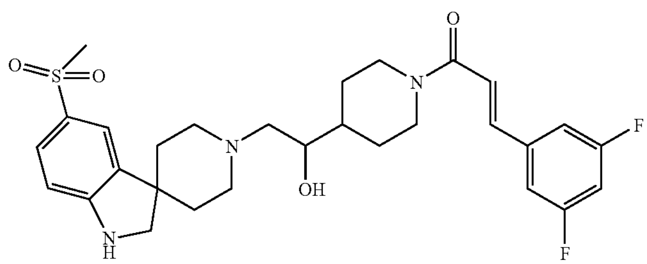 | 2 | 560 | 1-{1-[(2E)-3-(3,5-difluorophenyl)-2-propenoyl]-4-piperidinyl}-2-[5-(methylsulfonyl)-1,2-dihydro-1'H-spiro[indole-3,4'-piperidin]-1'-yl]ethanol |
| 39 | 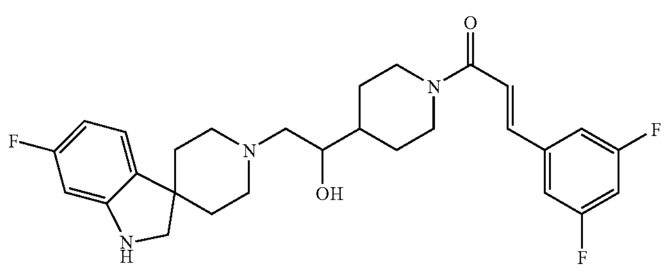 | 2 | 500 | 1-{1-[(2E)-3-(3,5-difluorophenyl)-2-propenoyl]-4-piperidinyl}-2-(6-fluoro-1,2-dihydro-1'H-spiro[indole-3,4'-piperidin]-1'-yl)ethanol |
| 40 | 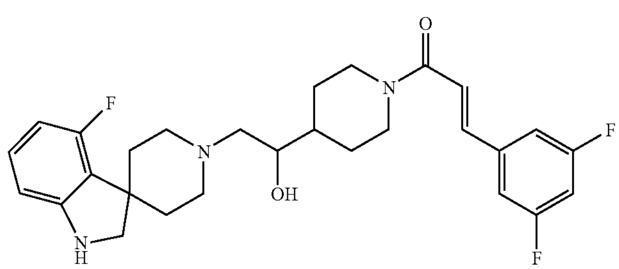 | 2 | 500 | 1-{1-[(2E)-3-(3,5-difluorophenyl)-2-propenoyl]-4-piperidinyl}-2-(4-fluoro-1,2-dihydro-1'H-spiro[indole-3,4'-piperidin]-1'-yl)ethanol |

-continued

| Ex # | Chemical Structure | Schm. | m/z | Name |
|---|---|---|---|---|
| 41 | 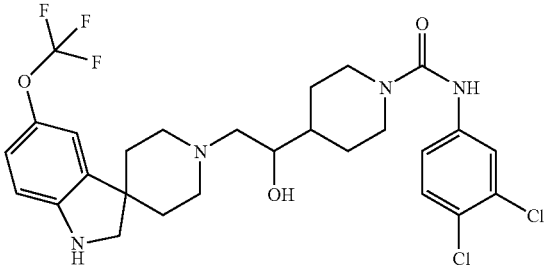 | 2 | 587 | N-(3,4-dichlorophenyl)-4-(1-hydroxy-2-{5-[(trifluoromethyl)oxy]-1,2-dihydro-1'H-spiro[indole-3,4'-piperidin]-1'-yl}ethyl)-1-piperidine-carboxamide |
| 42 | 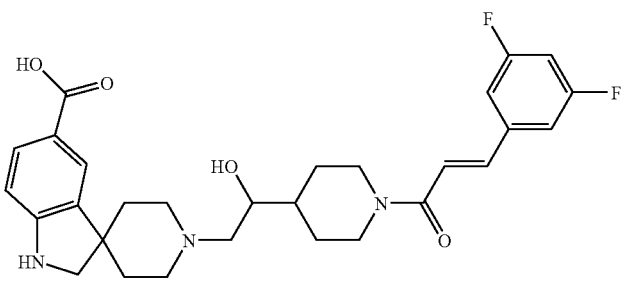 | 2 | 526 | 1'-(2-{1-[(2E)-3-(3,5-difluorophenyl)-2-propenoyl]-4-piperidinyl}-2-hydroxyethyl)-1,2-dihydrospiro[indole-3,4'-piperidine]-5-carboxylic acid |
| 43 | 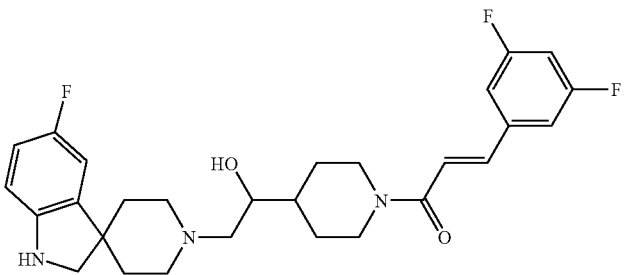 | 2 | 500 | 1-{1-[(2E)-3-(3,5-difluorophenyl)-2-propenoyl]-4-piperidinyl}-2-(5-fluoro-1,2-dihydro-1'H-spiro[indole-3,4'-piperidin]-1'-yl)ethanol |
| 44 | 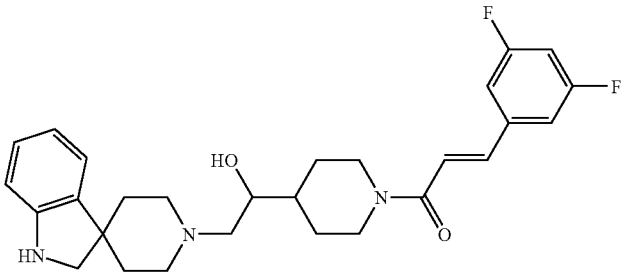 | 2 | 482 | 1-{1-[(2E)-3-(3,5-difluorophenyl)-2-propenoyl]-4-piperidinyl}-2-(1,2-dihydro-1'H-spiro[indole-3,4'-piperidin]-1'-yl)ethanol |
| 45 | 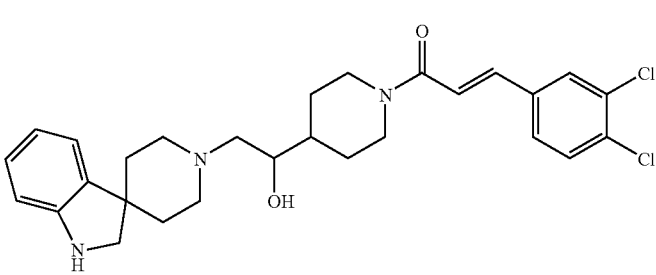 | 5 | 514 | 1-{1-[(2E)-3-(3,4-dichlorophenyl)-2-propenoyl]-4-piperidinyl}-2-(1,2-dihydro-1'H-spiro[indole-3,4'-piperidin]-1'-yl)ethanol |

-continued

| Ex # | Chemical Structure | Schm. | m/z | Name |
|---|---|---|---|---|
| 46 | 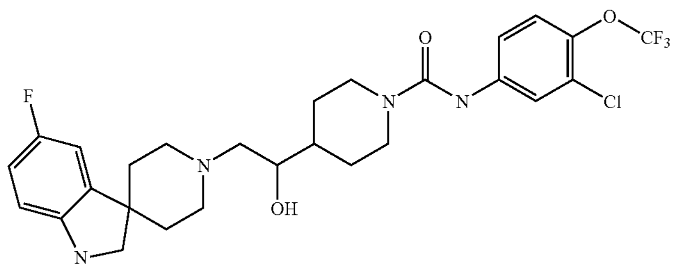 | 7 | 571 | N-{3-chloro-4-[(trifluoromethyl)oxy]phenyl}-4-[2-(5-fluoro-1,2-dihydro-1'H-spiro[indole-3,4'-piperidin]-1'-yl)-1-hydroxyethyl]-1-piperidine-carboxamide |
| 47 | 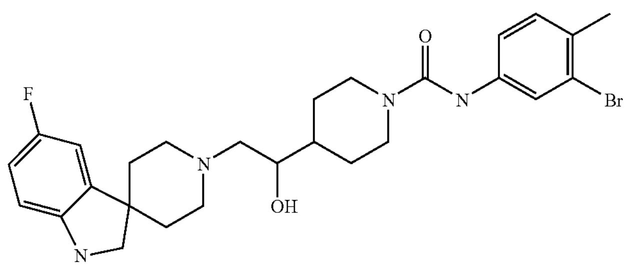 | 7 | 545 | N-(3-bromo-4-methylphenyl)-4-[2-(5-fluoro-1,2-dihydro-1'H-spiro[indole-3,4'-piperidin]-1'-yl)-1-hydroxyethyl]-1-piperidine-carboxamide |
| 48 | 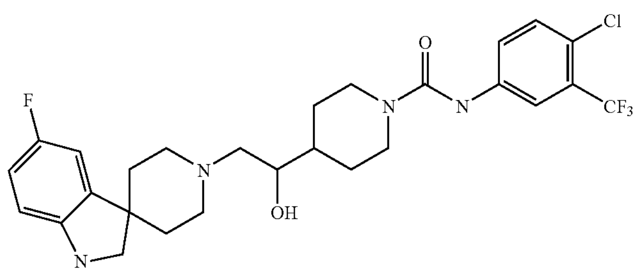 | 7 | 555 | N-[4-chloro-3-(trifluoromethyl)phenyl]-4-[2-(5-fluoro-1,2-dihydro-1'H-spiro[indole-3,4'-piperidin]-1'-yl)-1-hydroxyethyl]-1-piperidinecarboxamide |
| 49 | 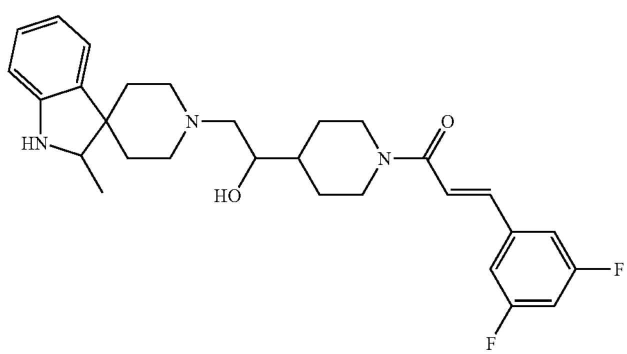 | 8 | 496 | 1-{1-[(2E)-3-(3,5-difluorophenyl)-2-propenoyl]-4-piperidinyl}-2-(2-methyl-1,2-dihydro-1'H-spiro[indole-3,4'-piperidin]-1'-yl)ethanol |
| 50 | 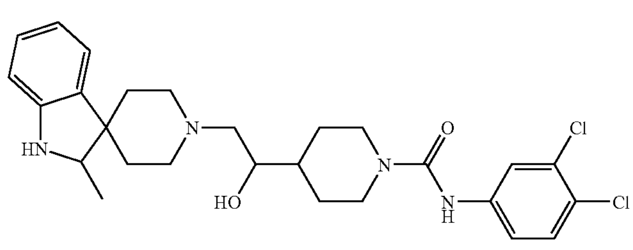 | 11 | 517 | N-(3,4-dichlorophenyl)-4-[1-hydroxy-2-(2-methyl-1,2-dihydro-1'H-spiro[indole-3,4'-piperidin]-1'-yl)ethyl]-1-piperidinecarboxamide |

| Ex # | Chemical Structure | Schm. | m/z | Name |
|---|---|---|---|---|
| 51 | 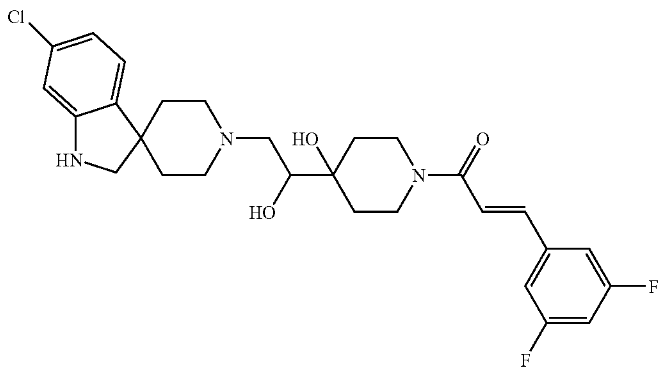 | 16 | 532 | 4-[2-(6-Chloro-1,2-dihydro-1'H-spiro[indole-3,4'-piperidin]-1'-yl)-1-hydroxyethyl]-1-[(2E)-3-(3,5-difluorophenyl)-2-propenoyl]-4-piperidinol |
| 52 | 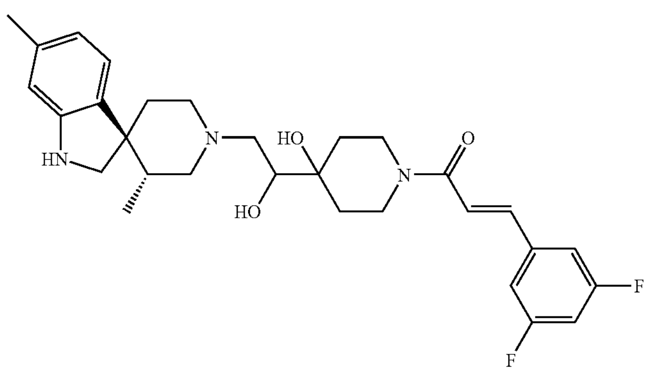 | 16, 20 | 526 | 1-[(2E)-3-(3,5-difluorophenyl)-2-propenoyl]-4-{2-[(3R,3'R)-3',6-dimethyl-1,2-dihydro-1'H-spiro[indole-3,4'-piperidin]-1'-yl]-1-hydroxyethyl}-4-piperidinol |
| 53 | 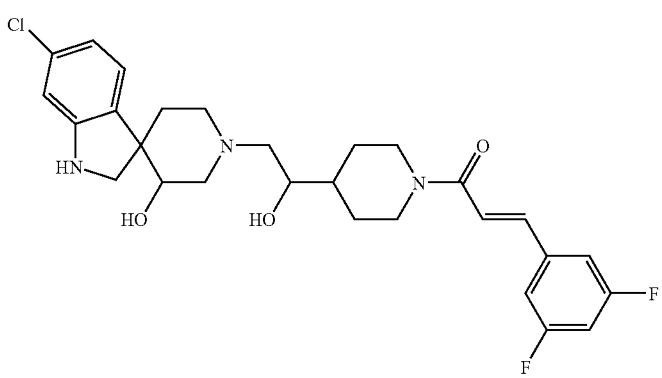 | 17 | 532 | 6-Chloro-1'-(2-{1-[(2E)-3-(3,5-difluorophenyl)-2-propenoyl]-4-piperidinyl}-2-hydroxyethyl)-1,2-dihydrospiro[indole-3,4'-piperidin]-3'-ol |
| 54 | 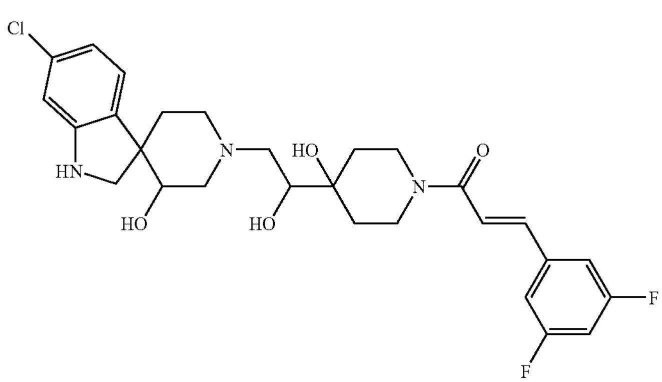 | 17 | 548 | 6-Chloro-1'-(2-{1-[(2E)-3-(3,5-difluorophenyl)-2-propenoyl]-4-hydroxy-4-piperidinyl}-2-hydroxyethyl)-1,2-dihydrospiro[indole-3,4'-piperidin]-3'-ol |

-continued

| Ex # | Chemical Structure | Schm. | m/z | Name |
|---|---|---|---|---|
| 55 | 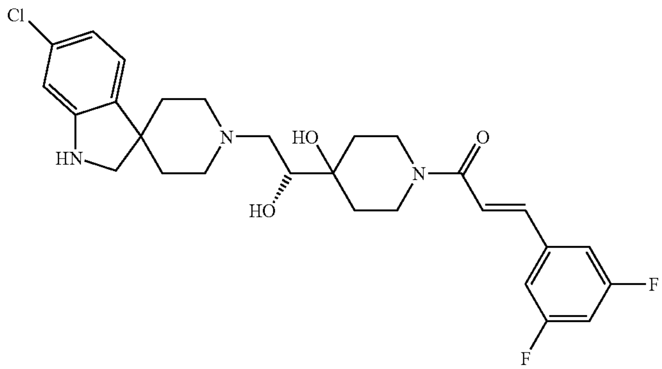 | 18 | 532 | 4-[(1R)-2-(6-chloro-1,2-dihydro-1'H-spiro[indole-3,4'-piperidin]-1'-yl)-1-hydroxyethyl]-1-[(2E)-3-(3,5-difluorophenyl)-2-propenoyl]-4-piperidinol |
| 56 | 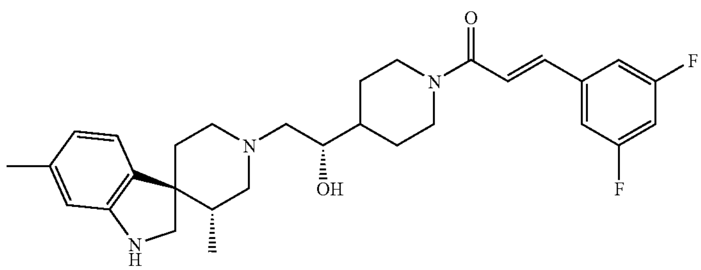 | 10, 20 | 510 | (1S)-1-{1-[(2E)-3-(3,5-difluorophenyl)-2-propenoyl]-4-piperidinyl}-2-[(3R,3'R)-3',6-dimethyl-1,2-dihydro-1'H-spiro[indole-3,4'-piperidin]-1'-yl]ethanol |
| 57 | 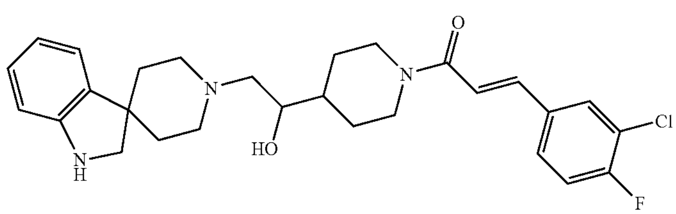 | 5 | 498 | 1-{1-[(2E)-3-(3-chloro-4-fluorophenyl)-2-propenoyl]-4-piperidinyl}-2-(1,2-dihydro-1'H-spiro[indole-3,4'-piperidin]-1'-yl)ethanol |
| 58 | 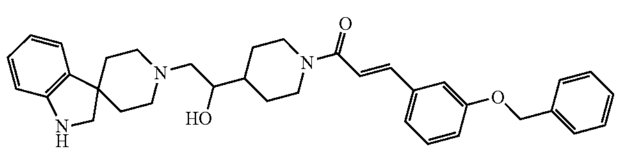 | 5 | 552 | 2-(1,2-dihydro-1'H-spiro[indole-3,4'-piperidin]-1'-yl)-1-[(2E)-3-{3-[(phenylmethyl)oxy]phenyl}-2-propenoyl)-4-piperidinyl]ethanol |
| 59 | 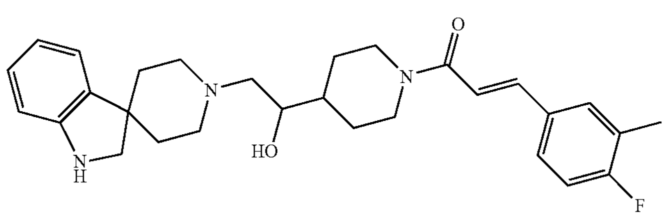 | 5 | 478 | 2-(1,2-dihydro-1'H-spiro[indole-3,4'-piperidin]-1'-yl)-1-{1-[(2E)-3-(4-fluoro-3-methylphenyl)-2-propenoyl]-4-piperidinyl}ethanol |
| 60 | 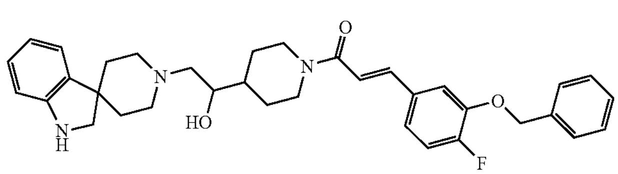 | 5 | 570 | 2-(1,2-dihydro-1'H-spiro[indole-3,4'-piperidin]-1'-yl)-1-[1-((2E)-3-{4-fluoro-3-[(phenylmethyl)oxy]phenyl}-2-propenoyl)-4-piperidinyl]ethanol |

-continued

| Ex # | Chemical Structure | Schm. | m/z | Name |
|---|---|---|---|---|
| 61 | 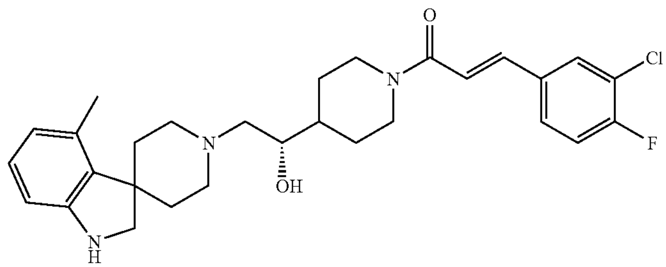 | 5 | 512 | (1S)-1-{1-[(2E)-3-(3-chloro-4-fluorophenyl)-2-propenoyl]-4-piperidinyl}-2-(4-methyl-1,2-dihydro-1'H-spiro[indole-3,4'-piperidin]-1'-yl)ethanol |
| 62 | 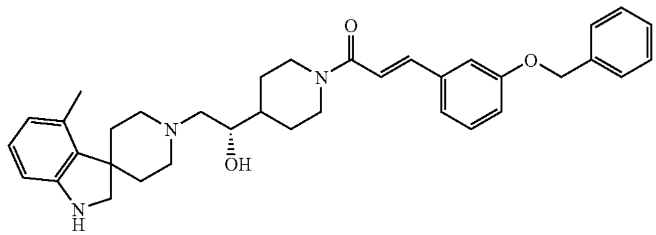 | 5 | 566 | (1S)-2-(4-methyl-1,2-dihydro-1'H-spiro[indole-3,4'-piperidin]-1'-yl)-1-[1-((2E)-3-{3-[(phenylmethyl)oxy]phenyl}-2-propenoyl)-4-piperidinyl]ethanol |
| 63 | 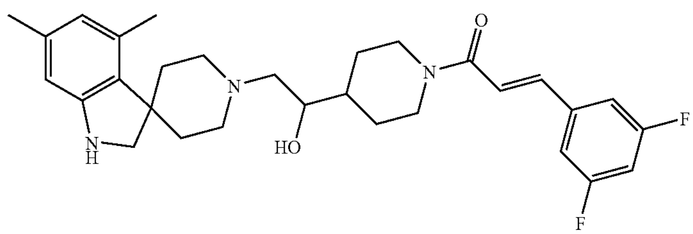 | 2 | 510 | 1-{1-[(2E)-3-(3,5-difluorophenyl)-2-propenoyl]-4-piperidinyl}-2-(4,6-dimethyl-1,2-dihydro-1'H-spiro[indole-3,4'-piperidin]-1'-yl)ethanol |
| 64 | 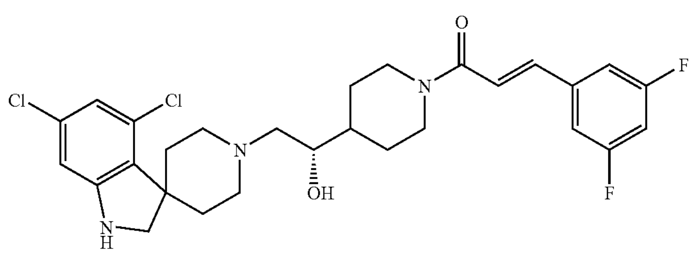 | 2 | 550 | (1S)-2-(4,6-dichloro-1,2-dihydro-1'H-spiro[indole-3,4'-piperidin]-1'-yl)-1-{1-[(2E)-3-(3,5-difluorophenyl)-2-propenoyl]-4-piperidinyl}ethanol |
| 65 | 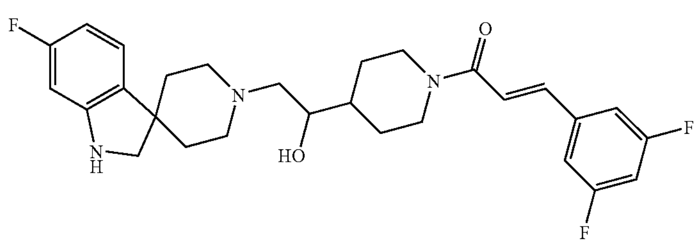 | 2 | 500 | 1-{1-[(2E)-3-(3,5-difluorophenyl)-2-propenoyl]-4-piperidinyl}-2-(6-fluoro-1,2-dihydro-1'H-spiro[indole-3,4'-piperidin]-1'-yl)ethanol |
| 66 | 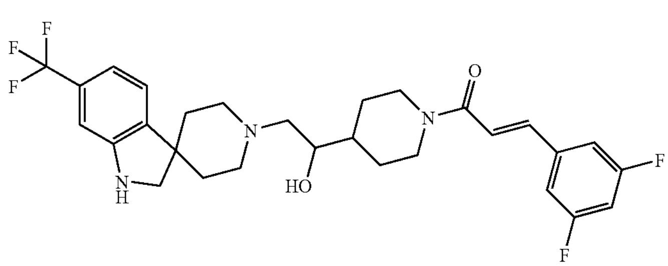 | 2 | 550 | 1-{1-[(2E)-3-(3,5-difluorophenyl)-2-propenoyl]-4-piperidinyl}-2-[6-(trifluoromethyl)-1,2-dihydro-1'H-spiro[indole-3,4'-piperidin]-1'-yl]ethanol |

| Ex # | Chemical Structure | Schm. | m/z | Name |
|---|---|---|---|---|
| 67 | 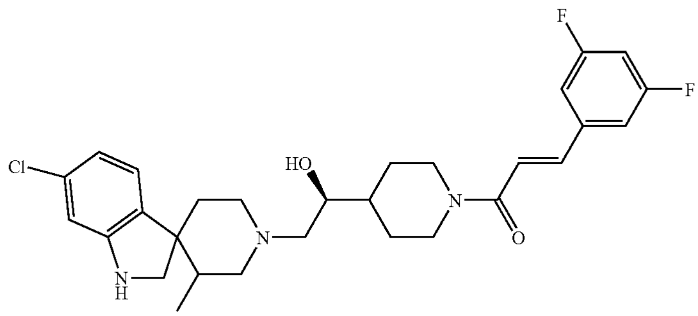 | 10, 20 | 530 | (1S)-2-(6-chloro-3'-methyl-1,2-dihydro-1'H-spiro[indole-3,4'-piperidin]-1'-yl)-1-{1-[(2E)-3-(3,5-difluorophenyl)-2-propenoyl]-4-piperidinyl}ethanol |
| 68 | 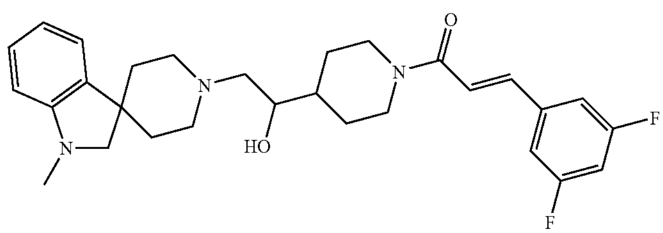 | 9 | 496 | 1-{1-[(2E)-3-(3,5-difluorophenyl)-2-propenoyl]-4-piperidinyl}-2-(1-methyl-1,2-dihydro-1'H-spiro[indole-3,4'-piperidin]-1'-yl)ethanol |
| 69 | 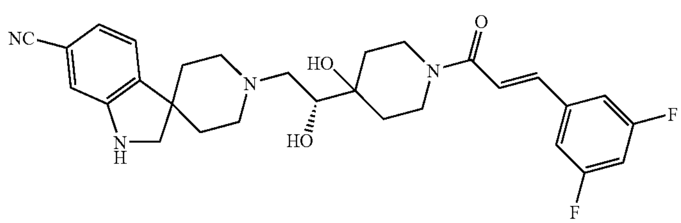 | 21, 18 | 523 | 1'-((2R)-2-{1-[(2E)-3-(3,5-difluorophenyl)-2-propenoyl]-4-hydroxy-4-piperidinyl}-2-hydroxyethyl)-1,2-dihydrospiro[indole-3,4'-piperidine]-6-carbonitrile |
| 70 | 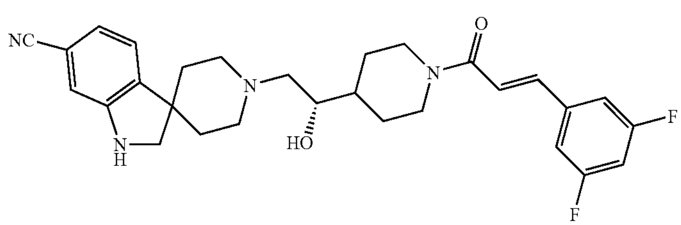 | 21, 2 | 507 | 1'-((2S)-2-{1-[(2E)-3-(3,5-difluorophenyl)-2-propenoyl]-4-piperidinyl}-2-hydroxyethyl)-1,2-dihydrospiro[indole-3,4'-piperidine]-6-carbonitrile |
| 71 | 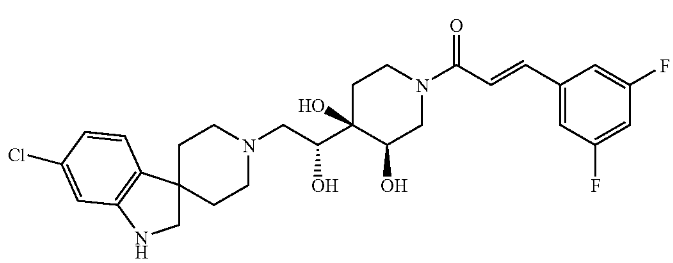 | 22 | 548 | (3R,4R)-4-[(1R)-2-(6-chloro-1,2-dihydro-1'H-spiro[indole-3,4'-piperidin]-1'-yl)-1-hydroxyethyl]-1-[(2E)-3-(3,5-difluorophenyl)-2-propenoyl]-3,4-piperidinediol |
| 72 | 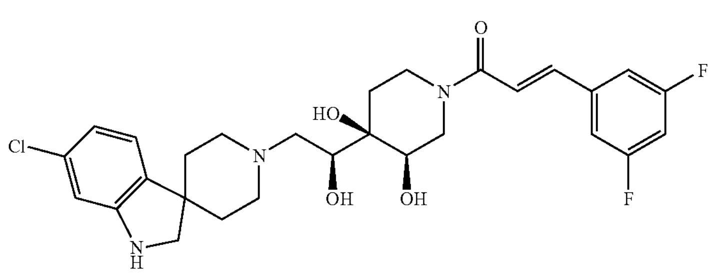 | 22 | 548 | (3R,4R)-4-[(1S)-2-(6-chloro-1,2-dihydro-1'H-spiro[indole-3,4'-piperidin]-1'-yl)-1-hydroxyethyl]-1-[(2E)-3-(3,5-difluorophenyl)-2-propenoyl]-3,4-piperidinediol |

-continued

| Ex # | Chemical Structure | Schm. | m/z | Name |
|---|---|---|---|---|
| 73 | 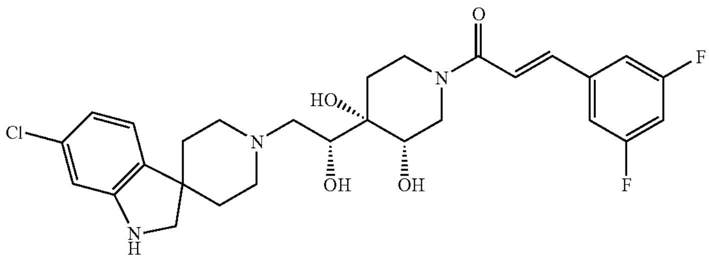 | 22 | 548 | (3S,4S)-4-[(1R)-2-(6-chloro-1,2-dihydro-1'H-spiro[indole-3,4'-piperidin]-1'-yl)-1-hydroxyethyl]-1-[(2E)-3-(3,5-difluorophenyl)-2-propenoyl]-3,4-piperidinediol |
| 74 | 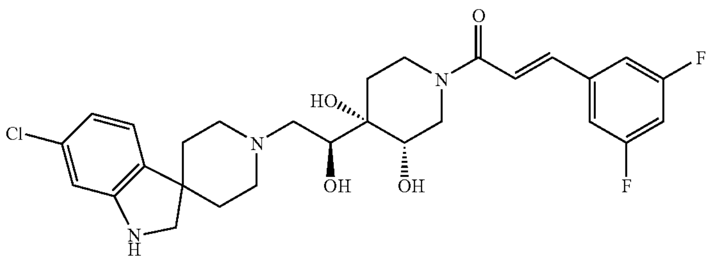 | 22 | 548 | (3S,4S)-4-[(1S)-2-(6-chloro-1,2-dihydro-1'H-spiro[indole-3,4'-piperidin]-1'-yl)-1-hydroxyethyl]-1-[(2E)-3-(3,5-difluorophenyl)-2-propenoyl]-3,4-piperidinediol |

The invention claimed is:

1. A compound which is (1S)-2-(6-chloro-1,2-dihydro-1'H-spiro[indole-3,4'-piperidin]-1'-yl)-1-{1-[(2E)-3-(3,5-difluorophenyl)-2-propenoyl]-4-piperidinyl}ethanol or a pharmaceutically acceptable salt thereof.

2. A pharmaceutically acceptable salt of the compound of claim 1, wherein the salt is a benzoate salt.

3. A composition that comprises a) the compound of claim 1 or a pharmaceutically acceptable salt thereof; and b) a pharmaceutically acceptable excipient.

4. A compound which is 2-(6-chloro-1,2-dihydro-1'H-spiro[indole-3,4'-piperidin]-1'-yl)-1-{1-[(2E)-3-(3,5-difluorophenyl)-2-propenoyl]-4-piperidinyl}ethanol or a pharmaceutically acceptable salt thereof.

5. A composition that comprises a) (1S)-2-(6-chloro-1,2-dihydro-1'H-spiro[indole-3,4'-piperidin]-1'-yl)-1-{1-[(2E)-3-(3,5-difluorophenyl)-2-propenoyl]-4-piperidinyl}ethanol benzoate salt; and b) a pharmaceutically acceptable excipient.

\* \* \* \* \*